(12) United States Patent
Bufe et al.

(10) Patent No.: US 8,709,737 B2
(45) Date of Patent: Apr. 29, 2014

(54) BITTER TASTE RECEPTORS

(75) Inventors: Bernd Bufe, Ferch (DE); Thomas Hofmann, Münster-Roxel (DE); Dietmar Krautwurst, Bergholz-Rehbrücke (DE); Christina Kuhn, Bergholz-Rehbrücke (DE); Wolfgang Meyerhof, Norderstedt (DE)

(73) Assignee: Deutsches Institut für Ernährungsforschung, Stiftung des öffentlichen Rechts, Vertreten durch den Stiftungsvorstand, Nethetal (DE)

( * ) Notice: Subject to any disclaimer, the term of this patent is extended or adjusted under 35 U.S.C. 154(b) by 0 days.

(21) Appl. No.: 13/071,924

(22) Filed: Mar. 25, 2011

(65) Prior Publication Data

US 2011/0177085 A1 Jul. 21, 2011

Related U.S. Application Data

(60) Continuation of application No. 12/168,551, filed on Jul. 7, 2008, now Pat. No. 7,955,808, which is a division of application No. 10/528,630, filed as application No. PCT/EP03/10691 on Sep. 25, 2003, now Pat. No. 7,413,867.

(60) Provisional application No. 60/413,298, filed on Sep. 25, 2002.

(51) Int. Cl.
*G01N 33/567* (2006.01)
(52) U.S. Cl.
USPC .......................................... 435/7.21

(58) Field of Classification Search
None
See application file for complete search history.

(56) References Cited

U.S. PATENT DOCUMENTS

| 7,105,650 B2 | 9/2006 | Adler |
| 2002/0094551 A1 | 7/2002 | Adler |
| 2004/0248123 A1 | 12/2004 | Drayna et al. |

FOREIGN PATENT DOCUMENTS

| WO | WO 01/18050 A2 * | 3/2001 | ............ C07K 14/47 |
| WO | WO 01/77676 A1 | 10/2001 | |

OTHER PUBLICATIONS

Bufe, B. et al., "The human TAS2R16 receptor mediates bitter taste in response to β-glucopyranosides," *Nature Genetics*, Nov. 2002, vol. 32, pp. 397-401.
Bufe, B. et al., "*Homo sapiens* candidate receptor TAS2R38 gene," Database EMBL (Online), Apr. 29, 2002, Database accession No. AF494231.
Chandrashekar, J. et al., "T2Rs Function as Bitter Taste Receptors," *Cell*, Mar. 17, 2000, vol. 100, pp. 703-711.
Margolskee, R.F., "Molecular Mechanisms of Bitter and Sweet Taste Transduction," *J. Biol. Chem.*, Jan. 4, 2002, vol. 277, No. 1, pp. 1-4.

* cited by examiner

*Primary Examiner* — John Ulm
(74) *Attorney, Agent, or Firm* — Saliwanchik, Lloyd & Eisenschenk

(57) ABSTRACT

The present invention relates to bitter-taste receptors and their role in bitter taste transduction. The invention also relates to assays for screening molecules that modulate, e.g. suppress or block, bitter taste transduction, or enhance bitter taste response.

4 Claims, No Drawings

SEQUENCE LISTING

<160> NUMBER OF SEQ ID NOS: 52

<210> SEQ ID NO 1
<211> LENGTH: 333
<212> TYPE: PRT

<213> ORGANISM: Homo sapiens

<400> SEQUENCE: 1

Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
            20                  25                  30

Asn Ala Phe Val Phe Leu Val Asn Phe Trp Asp Val Val Lys Arg Gln
        35                  40                  45

Ala Leu Ser Asn Ser Asp Cys Val Leu Leu Cys Leu Ser Ile Ser Arg
    50                  55                  60

Leu Phe Leu His Gly Leu Leu Phe Leu Ser Ala Ile Gln Leu Thr His
65                  70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
            100                 105                 110

Leu Ser Leu Leu Tyr Cys Ser Lys Leu Ile Arg Phe Ser His Thr Phe
        115                 120                 125

Leu Ile Cys Leu Ala Ser Trp Val Ser Arg Lys Ile Ser Gln Met Leu
    130                 135                 140

Leu Gly Ile Ile Leu Cys Ser Cys Ile Cys Thr Val Leu Cys Val Trp
145                 150                 155                 160

Cys Phe Phe Ser Arg Pro His Phe Thr Val Thr Thr Val Leu Phe Met
                165                 170                 175

Asn Asn Asn Thr Arg Leu Asn Trp Gln Asn Lys Asp Leu Asn Leu Phe
            180                 185                 190

Tyr Ser Phe Leu Phe Cys Tyr Leu Trp Ser Val Pro Pro Phe Leu Leu
        195                 200                 205

Phe Leu Val Ser Ser Gly Met Leu Thr Val Ser Leu Gly Arg His Met
    210                 215                 220

Arg Thr Met Lys Val Tyr Thr Arg Asn Ser Arg Asp Pro Ser Leu Glu
225                 230                 235                 240

Ala His Ile Lys Ala Leu Lys Ser Leu Val Ser Phe Phe Cys Phe Phe
                245                 250                 255

Val Ile Ser Ser Cys Val Ala Phe Ile Ser Val Pro Leu Leu Ile Leu
            260                 265                 270

Trp Arg Asp Lys Ile Gly Val Met Val Cys Val Gly Ile Met Ala Ala
        275                 280                 285

Cys Pro Ser Gly His Ala Ala Ile Leu Ile Ser Gly Asn Ala Lys Leu
    290                 295                 300

Arg Arg Ala Val Met Thr Ile Leu Leu Trp Ala Gln Ser Ser Leu Lys
305                 310                 315                 320

Val Arg Ala Asp His Lys Ala Asp Ser Arg Thr Leu Cys
                325                 330

<210> SEQ ID NO 2
<211> LENGTH: 999
<212> TYPE: DNA
<213> ORGANISM: Homo sapiens

<400> SEQUENCE: 2
atgttgactc taactcgcat ccgcactgtg tcctatgaag tcaggagtac atttctgttc       60
atttcagtcc tggagtttgc agtggggttt ctgaccaatg ccttcgtttt cttggtgaat      120
ttttgggatg tagtgaagag gcaggcactg agcaacagtg attgtgtgct gctgtgtctc      180

-continued

```
agcatcagcc ggcttttcct gcatggactg ctgttcctga gtgctatcca gcttacccac      240
ttccagaagt tgagtgaacc actgaaccac agctaccaag ccatcatcat gctatggatg      300
attgcaaacc aagccaacct ctggcttgct gcctgcctca gcctgcttta ctgctccaag      360
ctcatccgtt tctctcacac cttcctgatc tgcttggcaa gctgggtctc caggaagatc      420
tcccagatgc tcctgggtat tattctttgc tcctgcatct gcactgtcct ctgtgtttgg      480 tgcttttta gcagacctca cttcacagtc acaactgtgc tattcatgaa taacaataca      540
aggctcaact ggcagaataa agatctcaat ttattttatt cctttctctt ctgctatctg      600
tggtctgtgc ctcctttcct attgtttctg gtttcttctg ggatgctgac tgtctccctg      660
ggaaggcaca tgaggacaat gaaggtctat accagaaact ctcgtgaccc cagcctggag      720
gcccacatta aagccctcaa gtctcttgtc tccttttct gcttctttgt gatatcatcc      780
tgtgttgcct tcatctctgt gcccctactg attctgtggc gcgacaaaat aggggtgatg      840
gtttgtgttg ggataatggc agcttgtccc tctgggcatg cagccatcct gatctcaggc      900
aatgccaagt tgaggagagc tgtgatgacc attctgctct gggctcagag cagcctgaag      960
gtaagagccg accacaaggc agattcccgg acactgtgc                               999
```

```
<210> SEQ ID NO 3
<211> LENGTH: 337
<212> TYPE: PRT
<213> ORGANISM: Homo sapiens

<400> SEQUENCE: 3

Met Leu Gly Arg Cys Phe Pro Pro Asp Thr Lys Glu Lys Gln Gln Leu
1               5                   10                  15

Arg Met Thr Lys Leu Cys Asp Pro Ala Glu Ser Glu Leu Ser Pro Phe
            20                  25                  30

Leu Ile Thr Leu Ile Leu Ala Val Leu Ala Glu Tyr Leu Ile Gly
        35                  40                  45

Ile Ile Ala Asn Gly Phe Ile Met Ala Ile His Ala Ala Glu Trp Val
    50                  55                  60

Gln Asn Lys Ala Val Ser Thr Ser Gly Arg Ile Leu Val Phe Leu Ser
65                  70                  75                  80

Val Ser Arg Ile Ala Leu Gln Ser Leu Met Met Leu Glu Ile Thr Ile
                85                  90                  95

Ser Ser Thr Ser Leu Ser Phe Tyr Ser Glu Asp Ala Val Tyr Tyr Ala
            100                 105                 110

Phe Lys Ile Ser Phe Ile Phe Leu Asn Phe Cys Ser Leu Trp Phe Ala
        115                 120                 125

Ala Trp Leu Ser Phe Phe Tyr Phe Val Lys Ile Ala Asn Phe Ser Tyr
    130                 135                 140

Pro Leu Phe Leu Lys Leu Arg Trp Arg Ile Thr Gly Leu Ile Pro Trp
145                 150                 155                 160

Leu Leu Trp Leu Ser Val Phe Ile Ser Phe Ser His Ser Met Phe Cys
                165                 170                 175

Ile Asn Ile Cys Thr Val Tyr Cys Asn Asn Ser Phe Pro Ile His Ser
            180                 185                 190

Ser Asn Ser Thr Lys Lys Thr Tyr Leu Ser Glu Ile Asn Val Val Gly
        195                 200                 205

Leu Ala Phe Phe Phe Asn Leu Gly Ile Val Thr Pro Leu Ile Met Phe
    210                 215                 220

Ile Leu Thr Ala Thr Leu Leu Ile Leu Ser Leu Lys Arg His Thr Leu
```

```
                225                 230                 235                 240
His Met Gly Ser Asn Ala Thr Gly Ser Asn Asp Pro Ser Met Glu Ala
                    245                 250                 255

His Met Gly Ala Ile Lys Ala Ile Ser Tyr Phe Leu Ile Leu Tyr Ile
                    260                 265                 270

Phe Asn Ala Val Ala Leu Phe Ile Tyr Leu Ser Asn Met Phe Asp Ile
                    275                 280                 285

Asn Ser Leu Trp Asn Asn Leu Cys Gln Ile Ile Met Ala Ala Tyr Pro
                    290                 295                 300

Ala Ser His Ser Ile Leu Leu Ile Gln Asp Asn Pro Gly Leu Arg Arg
305                 310                 315                 320

Ala Trp Ser Gly Phe Ser Phe Asp Phe Ile Phe Thr Gln Lys Ser Gly
                    325                 330                 335

Leu

<210> SEQ ID NO 4
<211> LENGTH: 1013
<212> TYPE: DNA
<213> ORGANISM: Homo sapiens

<400> SEQUENCE: 4
atgctaggga gatgttttcc tccagacacc aaagagaagc aacagctcag aatgactaaa      60
ctctgcgatc ctgcagaaag tgaattgtcg ccatttctca tcaccttaat tttagcagtt     120
ttacttgctg aatacctcat tggtatcatt gcaaatggtt tcatcatggc tatacatgca     180
gctgaatggg ttcaaaataa ggcagtttcc acaagtggca ggatcctggt tttcctgagt     240
gtatccagaa tagctctcca aagcctcatg atgttagaaa ttaccatcag ctcaacctcc     300
ctaagttttt attctgaaga cgctgtatat tatgcattca aaataagttt tatattctta     360
aattttgtag cctgtggtt tgctgcctgg ctcagtttct tctactttgt gaagattgcc      420
aatttctcct accccttttt cctcaaactg aggtggagaa ttactggatt gatacctgg     480
cttctgtggc tgtccgtgtt tatttccttc agtcacagca tgttctgcat caacatctgc    540
actgtgtatt gtaacaattc tttccctatc cactcctcca actccactaa gaaaacatac     600
ttgtctgaga tcaatgtggt cggtctggct tttttctta acctggggat tgtgactcct      660
ctgatcatgt tcatcctgac agccaccctg ctgatcctct ctctcaagag acacacccta     720
cacatgggaa gcaatgccac agggtccaac gaccccagca tggaggctca catggggcc      780
atcaaagcta tcagctactt tctcattctc tacattttca tgcagttgc tctgtttatc       840
tacctgtcca acatgtttga catcaacagt ctgtggaata attttgtgcca gatcatcatg    900
gctgcctacc ctgccagcca ctcaattcta ctgattcaag ataaccctgg gctgagaaga     960
gcctggagcg gcttcagctt cgacttcatc tttacccaaa agagtggact ctg           1013

<210> SEQ ID NO 5
<211> LENGTH: 323
<212> TYPE: PRT
<213> ORGANISM: Homo sapiens

<400> SEQUENCE: 5

Met Ala Thr Val Asn Thr Asp Ala Thr Asp Lys Asp Ile Ser Lys Phe
1               5                   10                  15

Lys Val Thr Phe Thr Leu Val Val Ser Gly Ile Glu Cys Ile Thr Gly
                20                  25                  30

Ile Leu Gly Ser Gly Phe Ile Thr Ala Ile Tyr Gly Ala Glu Trp Ala
                35                  40                  45
```

Arg Gly Lys Thr Leu Pro Thr Gly Asp Arg Ile Met Leu Met Leu Ser
    50                  55                  60

Phe Ser Arg Leu Leu Leu Gln Ile Trp Met Met Leu Glu Asn Ile Phe
65                  70                  75                  80

Ser Leu Leu Phe Arg Ile Val Tyr Asn Gln Asn Ser Val Tyr Ile Leu
                85                  90                  95

Phe Lys Val Ile Thr Val Phe Leu Asn His Ser Asn Leu Trp Phe Ala
            100                 105                 110

Ala Trp Leu Lys Val Phe Tyr Cys Leu Arg Ile Ala Asn Phe Asn His
        115                 120                 125

Pro Leu Phe Phe Leu Met Lys Arg Lys Ile Ile Val Leu Met Pro Trp
    130                 135                 140

Leu Leu Arg Leu Ser Val Leu Val Ser Leu Ser Phe Ser Phe Pro Leu
145                 150                 155                 160

Ser Arg Asp Val Phe Asn Val Tyr Val Asn Ser Ser Ile Pro Ile Pro
                165                 170                 175

Ser Ser Asn Ser Thr Glu Lys Lys Tyr Phe Ser Glu Thr Asn Met Val
            180                 185                 190

Asn Leu Val Phe Phe Tyr Asn Met Gly Ile Phe Val Pro Leu Ile Met
        195                 200                 205

Phe Ile Leu Ala Ala Thr Leu Leu Ile Leu Ser Leu Lys Arg His Thr
    210                 215                 220

Leu His Met Gly Ser Asn Ala Thr Gly Ser Arg Asp Pro Ser Met Lys
225                 230                 235                 240

Ala His Ile Gly Ala Ile Lys Ala Thr Ser Tyr Phe Leu Ile Leu Tyr
                245                 250                 255

Ile Phe Asn Ala Ile Ala Leu Phe Leu Ser Thr Ser Asn Ile Phe Asp
            260                 265                 270

Thr Tyr Ser Ser Trp Asn Ile Leu Cys Lys Ile Ile Met Ala Ala Tyr
        275                 280                 285

Pro Ala Gly His Ser Val Gln Leu Ile Leu Gly Asn Pro Gly Leu Arg
    290                 295                 300

Arg Ala Trp Lys Arg Phe Gln His Gln Val Pro Leu Tyr Leu Lys Gly
305                 310                 315                 320

Gln Thr Leu

<210> SEQ ID NO 6
<211> LENGTH: 969
<212> TYPE: DNA
<213> ORGANISM: Homo sapiens

<400> SEQUENCE: 6
atggcaacgg tgaacacaga tgccacagat aaagacatat ccaagttcaa ggtcaccttc      60
actttggtgg tctccggaat agagtgcatc actggcatcc ttgggagtgg cttcatcacg     120
gccatctatg gggctgagtg gccagggggc aaaacactcc ccactggtga ccgcattatg     180
ttgatgctga gcttttccag gctcttgcta cagatttgga tgatgctgga gaacattttc     240
agtctgctat tccgaattgt ttataaccaa aactcagtgt atatcctctt caaagtcatc     300
actgtctttc tgaaccattc aatctctggt tttgctgcct ggctcaaagt cttctattgt     360
cttagaattg caaacttcaa tcatcctttg ttcttcctga tgaagaggaa aatcatagtg     420
ctgatgcctt ggcttctcag gctgtcagtg ttggtttcct taagcttcag ctttcctctc     480
tcgagagatg tcttcaatgt gtatgtgaat agctccattc ctatcccctc ctccaactcc     540

```
acggagaaga agtacttctc tgagaccaat atggtcaacc tggtattttt ctataacatg    600
gggatcttcg ttcctctgat catgttcatc ctggcagcca ccctgctgat cctctctctc    660
aagagacaca ccctacacat gggaagcaat gccacagggt ccagggaccc cagcatgaag    720
gctcacatag gggccatcaa agccaccagc tactttctca tcctctacat tttcaatgca    780
attgctctat ttcttttccac gtccaacatc tttgacactt acagttcctg gaatattttg    840
tgcaagatca tcatggctgc ctaccctgcc ggccactcag tacaactgat cttgggcaac    900
cctgggctga aagagccctg aagcggtttt cagcaccaag ttcctctttta cctaaaaggg    960 cagactctg                                                            969
```

<210> SEQ ID NO 7
<211> LENGTH: 307
<212> TYPE: PRT
<213> ORGANISM: Homo sapiens

<400> SEQUENCE: 7

```
Met Gln Ala Ala Leu Thr Ala Phe Phe Val Leu Leu Phe Ser Leu Leu
1               5                   10                  15

Ser Leu Leu Gly Ile Ala Ala Asn Gly Phe Ile Val Leu Val Leu Gly
            20                  25                  30

Arg Glu Trp Leu Arg Tyr Gly Arg Leu Leu Pro Leu Asp Met Ile Leu
        35                  40                  45

Ile Ser Leu Gly Ala Ser Arg Phe Cys Leu Gln Leu Val Gly Thr Val
    50                  55                  60

His Asn Phe Tyr Tyr Ser Ala Gln Lys Val Glu Tyr Ser Gly Gly Leu
65                  70                  75                  80

Gly Arg Gln Phe Phe His Leu His Trp His Phe Leu Asn Ser Ala Thr
                85                  90                  95

Phe Trp Phe Cys Ser Trp Leu Ser Val Leu Phe Cys Val Lys Ile Ala
            100                 105                 110

Asn Ile Thr His Ser Thr Phe Leu Trp Leu Lys Trp Arg Phe Leu Gly
        115                 120                 125

Trp Val Pro Trp Leu Leu Leu Gly Ser Val Leu Ile Ser Phe Ile Ile
    130                 135                 140

Thr Leu Leu Phe Phe Trp Val Asn Tyr Pro Val Tyr Gln Glu Phe Leu
145                 150                 155                 160

Ile Arg Lys Phe Ser Gly Asn Met Thr Tyr Lys Trp Asn Thr Arg Ile
                165                 170                 175

Glu Thr Tyr Tyr Phe Pro Ser Leu Lys Leu Val Ile Trp Ser Ile Pro
            180                 185                 190

Phe Ser Val Phe Leu Val Ser Ile Met Leu Leu Ile Asn Ser Leu Arg
        195                 200                 205

Arg His Thr Gln Arg Met Gln His Asn Gly His Ser Leu Gln Asp Pro
    210                 215                 220

Ser Thr Gln Ala His Thr Arg Ala Leu Lys Ser Leu Ile Ser Phe Leu
225                 230                 235                 240

Ile Leu Tyr Ala Leu Ser Phe Leu Ser Leu Ile Asp Ala Ala Lys
                245                 250                 255

Phe Ile Ser Met Gln Asn Asp Phe Tyr Trp Pro Trp Gln Ile Ala Val
            260                 265                 270

Tyr Leu Cys Ile Ser Val His Pro Phe Ile Leu Ile Phe Ser Asn Leu
        275                 280                 285

Lys Leu Arg Ser Val Phe Ser Gln Leu Leu Leu Leu Ala Arg Gly Phe
    290                 295                 300
```

Trp Val Ala
305

<210> SEQ ID NO 8
<211> LENGTH: 921
<212> TYPE: DNA
<213> ORGANISM: Homo sapiens

<400> SEQUENCE: 8

```
atgcaagcag cactgacggc cttcttcgtg ttgctctttta gcctgctgag tcttctgggg      60
attgcagcga atggcttcat tgtgctggtc ctgggcaggg agtggctgcg atatggcagg     120
ttgctgccct tggatatgat cctcattagc ttgggtgcct cccgcttctg cctgcagttg     180
gttgggacag tgcacaactt ctactactct gcccagaagg tcgagtactc tgggggtctc     240
ggccgacagt tcttccatct acactggcac ttcctgaact cagccacctt ctggttttgc     300
agctggctca gtgtcctgtt ctgtgtgaag attgctaaca tcacacactc caccttcctg     360
tggctgaagt ggaggttcct agggtgggtg ccctggctcc tgttgggctc tgtcctgatc     420
tccttcatca taaccctgct gttttttttgg gtgaactacc ctgtatatca agaatttttta     480
attagaaaat tttctgggaa catgacctac aagtggaata caaggataga acatactat      540
ttcccatccc tgaaactggt catctggtca attcctttttt ctgttttttct ggtctcaatt     600
atgctgttaa ttaattctct gaggaggcat actcagagaa tgcagcacaa cgggcacagc     660
ctgcaggacc ccagcaccca ggctcacacc agagctctga agtccctcat ctccttcctc     720
attctttatg ctctgtcctt tctgtccctg atcattgatg ccgcaaaatt tatctccatg     780
cagaacgact tttactggcc atggcaaatt gcagtctacc tgtgcatatc tgtccatccc     840
ttcatcctca tcttcagcaa cctcaagctt cgaagcgtgt tctcacagct cctgttgttg     900
gcaagggggct tctgggtggc c                                              921
```

<210> SEQ ID NO 9
<211> LENGTH: 309
<212> TYPE: PRT
<213> ORGANISM: Homo sapiens

<400> SEQUENCE: 9

Met Ile Thr Phe Leu Pro Ile Ile Phe Ser Ser Leu Val Val Thr
1               5                   10                  15

Phe Val Ile Gly Asn Phe Ala Asn Gly Phe Ile Ala Leu Val Asn Ser
            20                  25                  30

Ile Glu Ser Phe Lys Arg Gln Lys Ile Ser Phe Ala Asp Gln Ile Leu
        35                  40                  45

Thr Ala Leu Ala Val Ser Arg Val Gly Leu Leu Trp Val Leu Leu Leu
    50                  55                  60

Asn Trp Tyr Ser Thr Val Leu Asn Pro Ala Phe Asn Ser Val Glu Val
65                  70                  75                  80

Arg Thr Thr Ala Tyr Asn Ile Trp Ala Val Ile Asn His Phe Ser Asn
                85                  90                  95

Trp Leu Ala Thr Thr Leu Ser Ile Phe Tyr Leu Leu Lys Ile Ala Asn
            100                 105                 110

Phe Ser Asn Phe Ile Phe Leu His Leu Lys Arg Val Lys Ser Val
        115                 120                 125

Ile Leu Val Met Leu Leu Gly Pro Leu Leu Phe Leu Ala Cys His Leu
    130                 135                 140

Phe Val Ile Asn Met Asn Glu Ile Val Arg Thr Lys Glu Phe Glu Gly

```
                145                 150                 155                 160
Asn Met Thr Trp Lys Ile Lys Leu Lys Ser Ala Met Tyr Phe Ser Asn
                    165                 170                 175
Met Thr Val Thr Met Val Ala Asn Leu Val Pro Phe Thr Leu Thr Leu
                    180                 185                 190
Leu Ser Phe Met Leu Leu Ile Cys Ser Leu Cys Lys His Leu Lys Lys
                    195                 200                 205
Met Gln Leu Arg Gly Lys Gly Ser Gln Asp Pro Ser Thr Lys Val His
                    210                 215                 220
Ile Lys Ala Leu Gln Thr Val Ile Ser Phe Leu Leu Cys Ala Ile
225                 230                 235                 240
Tyr Phe Leu Ser Ile Met Ile Ser Val Trp Ser Phe Gly Ser Leu Glu
                    245                 250                 255
Asn Lys Pro Val Phe Met Phe Cys Lys Ala Ile Arg Phe Ser Tyr Pro
                    260                 265                 270
Ser Ile His Pro Phe Ile Leu Ile Trp Gly Asn Lys Lys Leu Lys Gln
                    275                 280                 285
Thr Phe Leu Ser Val Phe Trp Gln Met Arg Tyr Trp Val Lys Gly Glu
                    290                 295                 300
Lys Thr Ser Ser Pro
305
```

```
<210> SEQ ID NO 10
<211> LENGTH: 927
<212> TYPE: DNA
<213> ORGANISM: Homo sapiens

<400> SEQUENCE: 10
atgataactt ttctacccat cattttttcc agtctggtag tggttacatt tgttattgga      60
aattttgcta atggcttcat agcactggta aattccattg agtcgttcaa gagacaaaag     120
atctcctttg ctgaccaaat tctcactgct ctggcggtct ccagagttgg tttgctctgg     180
gtattattat taaactggta ttcaactgtg ttgaatccag cttttaatag tgtagaagta     240
agaactactg cttataatat ctgggcagtg atcaaccatt tcagcaactg gcttgctact     300
accctcagca tattttattt gctcaagatt gccaatttct ccaactttat ttttcttcac     360
ttaaagagga gagttaagag tgtcattctg gtgatgttgt ggggcctttt gctatttttg     420
gcttgtcatc tttttgtgat aaacatgaat gagattgtgc ggacaaaaga atttgaagga     480
aacatgactt ggaagatcaa attgaagagt gcaatgtact ttcaaatat gactgtaacc     540
atggtagcaa acttagtacc cttcactctg accctactat cttttatgct gttaatctgt     600
tctttgtgta acatctcaa gaagatgcag ctccgtggta aaggatctca agatcccagc     660
acgaaggtcc acataaaagc tttgcaaact gtgatctcct tcctcttgtt atgtgccatt     720
tactttctgt ccataatgat atcagtttgg agttttggaa gtctggaaaa caaacctgtc     780
ttcatgttct gcaaagctat tagattcagc tatccttcaa tccacccatt catcctgatt     840
tggggaaaca agaagctaaa gcagactttt ctttcagttt tttggcaaat gaggtactgg     900
gtgaaaggag agaagacttc atctcca                                         927
```

```
<210> SEQ ID NO 11
<211> LENGTH: 309
<212> TYPE: PRT
<213> ORGANISM: Homo sapiens

<400> SEQUENCE: 11
```

```
Met Thr Thr Phe Ile Pro Ile Ile Phe Ser Ser Val Val Val Leu
1               5                   10                  15

Phe Val Ile Gly Asn Phe Ala Asn Gly Phe Ile Ala Leu Val Asn Ser
            20                  25                  30

Ile Glu Arg Val Lys Arg Gln Lys Ile Ser Phe Ala Asp Gln Ile Leu
                35                  40                  45

Thr Ala Leu Ala Val Ser Arg Val Gly Leu Leu Trp Val Leu Leu Leu
    50                  55                  60

Asn Trp Tyr Ser Thr Val Phe Asn Pro Ala Phe Tyr Ser Val Glu Val
65                  70                  75                  80

Arg Thr Thr Ala Tyr Asn Val Trp Ala Val Thr Gly His Phe Ser Asn
                85                  90                  95

Trp Leu Ala Thr Ser Leu Ser Ile Phe Tyr Leu Leu Lys Ile Ala Asn
                100                 105                 110

Phe Ser Asn Leu Ile Phe Leu His Leu Lys Arg Arg Val Lys Ser Val
            115                 120                 125

Ile Leu Val Met Leu Leu Gly Pro Leu Leu Phe Leu Ala Cys Gln Leu
    130                 135                 140

Phe Val Ile Asn Met Lys Glu Ile Val Arg Thr Lys Glu Tyr Glu Gly
145                 150                 155                 160

Asn Met Thr Trp Lys Ile Lys Leu Arg Ser Ala Val Tyr Leu Ser Asp
                165                 170                 175

Ala Thr Val Thr Thr Leu Gly Asn Leu Val Pro Phe Thr Leu Thr Leu
            180                 185                 190

Leu Cys Phe Leu Leu Leu Ile Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Ala Leu Gln Thr Val Ile Phe Phe Leu Leu Leu Cys Ala Val
225                 230                 235                 240

Tyr Phe Leu Ser Ile Met Ile Ser Val Trp Ser Phe Gly Ser Leu Glu
                245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
            275                 280                 285

Thr Phe Leu Ser Val Leu Arg Gln Val Arg Tyr Trp Val Lys Gly Glu
    290                 295                 300

Lys Pro Ser Ser Pro
305

<210> SEQ ID NO 12
<211> LENGTH: 927
<212> TYPE: DNA
<213> ORGANISM: Homo sapiens

<400> SEQUENCE: 12
atgacaactt ttatacccat cattttttcc agtgtggtag tggttctatt tgttattgga      60
aattttgcta atggcttcat agcattggta aattccattg agcgggtcaa gagacaaaag     120 atctctttg ctgaccagat tctcactgct ctggcggtct ccagagttgg tttgctctgg     180
gtattattat taaattggta ttcaactgtg tttaatccag cttttatag tgtagaagta     240 agaactactg cttataatgt ctgggcagta accggccatt tcagcaactg gcttgctact     300
agcctcagca tattttattt gctcaagatt gccaatttct ccaaccttat ttttcttcac     360
```

```
ttaaagagga gagttaagag tgtcattctg gtgatgctgt tggggccttt actattttttg    420 gcttgtcaac ttttttgtgat aaacatgaaa gagattgtac ggacaaaaga atatgaagga    480
aacatgactt ggaagatcaa attgaggagt gcagtgtacc tttcagatgc gactgtaacc    540
acgctaggaa acttagtgcc cttcactctg accctgctat gttttttgct gttaatctgt    600
tctctgtgta aacatctcaa gaagatgcag ctccatggta aaggatctca agatcccagc    660
accaaggtcc acataaaagc tttgcaaact gtgatctttt tcctcttgtt atgtgccgtt    720
tactttctgt ccataatgat atcagtttgg agttttggga gtctggaaaa caaacctgtc    780
ttcatgttct gcaaagctat tagattcagc tatccttcaa tccacccatt catcctgatt    840
tggggaaaca agaagctaaa gcagactttt ctttcagttt tgcggcaagt gaggtactgg    900
gtgaaaggag agaagccttc atctcca                                        927
```

```
<210> SEQ ID NO 13
<211> LENGTH: 299
<212> TYPE: PRT
<213> ORGANISM: Homo sapiens

<400> SEQUENCE: 13

Met Ile Thr Phe Leu Pro Ile Ile Phe Ser Ile Leu Val Val Val Thr
1               5                   10                  15

Phe Val Ile Gly Asn Phe Ala Asn Gly Phe Ile Ala Leu Val Asn Ser
            20                  25                  30

Thr Glu Trp Val Lys Arg Gln Lys Ile Ser Phe Ala Asp Gln Ile Val
        35                  40                  45

Thr Ala Leu Ala Val Ser Arg Val Gly Leu Leu Trp Val Leu Leu Leu
    50                  55                  60

Asn Trp Tyr Ser Thr Val Leu Asn Pro Ala Phe Cys Ser Val Glu Leu
65                  70                  75                  80

Arg Thr Thr Ala Tyr Asn Ile Trp Ala Val Thr Gly His Phe Ser Asn
                85                  90                  95

Trp Pro Ala Thr Ser Leu Ser Ile Phe Tyr Leu Leu Lys Ile Ala Asn
            100                 105                 110

Phe Ser Asn Leu Ile Phe Leu Arg Leu Lys Arg Arg Val Lys Ser Val
        115                 120                 125

Ile Leu Val Val Leu Leu Gly Pro Leu Leu Phe Leu Ala Cys His Leu
    130                 135                 140

Phe Val Val Asn Met Asn Gln Ile Val Trp Thr Lys Glu Tyr Glu Gly
145                 150                 155                 160

Asn Met Thr Trp Lys Ile Lys Leu Arg Arg Ala Met Tyr Leu Ser Asp
                165                 170                 175

Thr Thr Val Thr Met Leu Ala Asn Leu Val Pro Phe Thr Val Thr Leu
            180                 185                 190

Ile Ser Phe Leu Leu Leu Val Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Val Leu Gln Thr Val Ile Ser Phe Phe Leu Leu Arg Ala Ile
225                 230                 235                 240

Tyr Phe Val Ser Val Ile Ile Ser Val Trp Ser Phe Lys Asn Leu Glu
                245                 250                 255

Asn Lys Pro Val Phe Met Phe Cys Gln Ala Ile Gly Phe Ser Cys Ser
            260                 265                 270

Ser Ala His Pro Phe Ile Leu Ile Trp Gly Asn Lys Lys Leu Lys Gln
```

```
                     275                 280                 285
Thr Tyr Leu Ser Val Leu Trp Gln Met Arg Tyr
        290                 295

<210> SEQ ID NO 14
<211> LENGTH: 897
<212> TYPE: DNA
<213> ORGANISM: Homo sapiens

<400> SEQUENCE: 14
atgataactt ttctgcccat catatttttcc attctagtag tggttacatt tgttattgga      60
aattttgcta atggcttcat agcgttggta aattccaccg agtgggtgaa gagacaaaag     120
atctcctttg ctgaccaaat tgtcactgct ctggcggtct ccagagttgg tttgctctgg     180
gtgttattat taaattggta ttcaactgtg ttgaatccag cttttgtag tgtagaatta      240 agaactactg cttataatat ctgggcagta accggccatt tcagcaactg gcctgctact     300
agcctcagca tattttatt gctcaagatt gccaatttct ccaaccttat ttttcttcgc      360
ttaaagagga gagttaagag tgtcattctg gtggtgctgt gggggccttt gctatttttg     420
gcttgtcatc ttttttgtggt aaacatgaat cagattgtat ggacaaaaga atatgaagga    480
aacatgactt ggaagatcaa attgaggcgt gcaatgtacc tttcagatac gactgtaacc    540
atgctagcaa acttagtacc cttactgta accctgatat cttttctgct gttagtctgt     600
tctctgtgta acatctcaa gaagatgcag ctccatggca aaggatctca agatcccagt     660
accaaggtcc acataaaagt tttgcaaact gtgatctcct tcttcttgtt acgtgccatt    720
tactttgtgt ctgtaataat atcagtttgg agttttaaga atctggaaaa caaacctgtc    780
ttcatgttct gccaagctat tggattcagc tgttcttcag cccacccgtt catcctgatt     840
tggggaaaca agaagctaaa gcagacttat ctttcagttt tgtggcaaat gaggtac        897

<210> SEQ ID NO 15
<211> LENGTH: 299
<212> TYPE: PRT
<213> ORGANISM: Homo sapiens

<400> SEQUENCE: 15

Met Ile Thr Phe Leu Pro Ile Ile Phe Ser Ile Leu Ile Val Val Thr
1               5                  10                  15

Phe Val Ile Gly Asn Phe Ala Asn Gly Phe Ile Ala Leu Val Asn Ser
            20                  25                  30

Ile Glu Trp Phe Lys Arg Gln Lys Ile Ser Phe Ala Asp Gln Ile Leu
        35                  40                  45

Thr Ala Leu Ala Val Ser Arg Val Gly Leu Leu Trp Val Leu Val Leu
    50                  55                  60

Asn Trp Tyr Ala Thr Glu Leu Asn Pro Ala Phe Asn Ser Ile Glu Val
65                  70                  75                  80

Arg Ile Thr Ala Tyr Asn Val Trp Ala Val Ile Asn His Phe Ser Asn
                85                  90                  95

Trp Leu Ala Thr Ser Leu Ser Ile Phe Tyr Leu Leu Lys Ile Ala Asn
            100                 105                 110

Phe Ser Asn Leu Ile Phe Leu His Leu Lys Arg Arg Val Lys Ser Val
        115                 120                 125

Val Leu Val Ile Leu Leu Gly Pro Leu Leu Phe Leu Val Cys His Leu
    130                 135                 140

Phe Val Ile Asn Met Asn Gln Ile Ile Trp Thr Lys Glu Tyr Glu Gly
145                 150                 155                 160
```

```
Asn Met Thr Trp Lys Ile Lys Leu Arg Ser Ala Met Tyr Leu Ser Asn
            165                 170                 175

Thr Thr Val Thr Ile Leu Ala Asn Leu Val Pro Phe Thr Leu Thr Leu
            180                 185                 190

Ile Ser Phe Leu Leu Leu Ile Cys Ser Leu Cys Lys His Leu Lys Lys
            195                 200                 205

Met Gln Leu His Gly Lys Gly Ser Gln Asp Pro Ser Met Lys Val His
            210                 215                 220

Ile Lys Ala Leu Gln Thr Val Thr Ser Phe Leu Leu Cys Ala Ile
225                 230                 235                 240

Tyr Phe Leu Ser Ile Ile Met Ser Val Trp Ser Phe Glu Ser Leu Glu
            245                 250                 255

Asn Lys Pro Val Phe Met Phe Cys Glu Ala Ile Ala Phe Ser Tyr Pro
            260                 265                 270

Ser Thr His Pro Phe Ile Leu Ile Trp Gly Asn Lys Lys Leu Lys Gln
            275                 280                 285

Thr Phe Leu Ser Val Leu Trp Gln Met Arg Tyr
            290                 295

<210> SEQ ID NO 16
<211> LENGTH: 897
<212> TYPE: DNA
<213> ORGANISM: Homo sapiens

<400> SEQUENCE: 16
atgataactt ttctgcccat cattttttcc attctaatag tggttacatt tgtgattgga      60
aattttgcta atggcttcat agcattggta aattccattg agtggtttaa gagacaaaag     120
atctcttttg ctgaccaaat tctcactgct ctggcagtct ccagagttgg tttactctgg     180
gtattagtat taaattggta tgcaactgag ttgaatccag cttttaacag tatagaagta     240
agaattactg cttacaatgt ctgggcagta atcaaccatt tcagcaactg gcttgctact     300
agcctcagca tattttattt gctcaagatt gccaatttct ccaacctat ttttcttcac      360 ttaaagagga gagttaagag tgttgttctg gtgatactat tggggccttt gctattttg      420 gtttgtcatc tttttgtgat aaacatgaat cagattatat ggacaaaaga atatgaagga     480
aacatgactt ggaagatcaa actgaggagt gcaatgtacc tttcaaatac aacggtaacc     540
atcctagcaa acttagttcc cttcactctg accctgatat cttttctgct gttaatctgt     600
tctctgtgta acatctcaa aaagatgcag ctccatggca aaggatctca agatcccagc     660
atgaaggtcc acataaaagc tttgcaaact gtgacctcct tcctcttgtt atgtgccatt     720
tactttctgt ccataatcat gtcagttggg agtttggaga gtctggaaaa caaacctgtc     780
ttcatgttct gcgaagctat tgcattcagc tatccttcaa cccacccatt catcctgatt     840
tggggaaaca agaagctaaa gcagactttt ctttcagttt gtggcaaat gaggtac        897

<210> SEQ ID NO 17
<211> LENGTH: 308
<212> TYPE: PRT
<213> ORGANISM: Homo sapiens

<400> SEQUENCE: 17

Met Ile Thr Phe Leu Pro Ile Ile Phe Ser Ile Leu Ile Val Val Ile
1               5                   10                  15

Phe Val Ile Gly Asn Phe Ala Asn Gly Phe Ile Ala Leu Val Asn Ser
            20                  25                  30
```

Ile Glu Trp Val Lys Arg Gln Lys Ile Ser Phe Val Asp Gln Ile Leu
 35                  40                  45

Thr Ala Leu Ala Val Ser Arg Val Gly Leu Leu Trp Val Leu Leu Leu
 50                  55                  60

His Trp Tyr Ala Thr Gln Leu Asn Pro Ala Phe Tyr Ser Val Glu Val
 65                  70                  75                  80

Arg Ile Thr Ala Tyr Asn Val Trp Ala Val Thr Asn His Phe Ser Ser
                 85                  90                  95

Trp Leu Ala Thr Ser Leu Ser Met Phe Tyr Leu Leu Arg Ile Ala Asn
                100                 105                 110

Phe Ser Asn Leu Ile Phe Leu Arg Ile Lys Arg Val Lys Ser Val
                115                 120                 125

Val Leu Val Ile Leu Leu Gly Pro Leu Leu Phe Leu Val Cys His Leu
                130                 135                 140

Phe Val Ile Asn Met Asp Glu Thr Val Trp Thr Lys Glu Tyr Glu Gly
145                 150                 155                 160

Asn Val Thr Trp Lys Ile Lys Leu Arg Ser Ala Met Tyr His Ser Asn
                165                 170                 175

Met Thr Leu Thr Met Leu Ala Asn Phe Val Pro Leu Thr Leu Thr Leu
                180                 185                 190

Ile Ser Phe Leu Leu Leu Ile Cys Ser Leu Cys Lys His Leu Lys Lys
                195                 200                 205

Met Gln Leu His Gly Lys Gly Ser Gln Asp Pro Ser Thr Lys Val His
                210                 215                 220

Ile Lys Ala Leu Gln Thr Val Thr Ser Phe Leu Leu Cys Ala Ile
225                 230                 235                 240

Tyr Phe Leu Ser Met Ile Ile Ser Val Cys Asn Phe Gly Arg Leu Glu
                245                 250                 255

Lys Gln Pro Val Phe Met Phe Cys Gln Ala Ile Ile Phe Ser Tyr Pro
                260                 265                 270

Ser Thr His Pro Phe Ile Leu Ile Leu Gly Asn Lys Lys Leu Lys Gln
                275                 280                 285

Ile Phe Leu Ser Val Leu Arg His Val Arg Tyr Trp Val Lys Asp Arg
                290                 295                 300

Ser Leu Arg Leu
305

<210> SEQ ID NO 18
<211> LENGTH: 926
<212> TYPE: DNA
<213> ORGANISM: Homo sapiens

<400> SEQUENCE: 18
atgataactt ttctgcccat cattttttcc attctaatag tggttatatt tgttattgga      60
aattttgcta atggcttcat agcattggta aattccattg agtgggtcaa agacaaaag     120 atctccttg ttgaccaaat tctcactgct ctggcggtct ccagagttgg tttgctctgg     180
gtgttattac tacattggta tgcaactcag ttgaatccag ctttttatag tgtagaagta     240
agaattactg cttataatgt ctgggcagta accaaccatt tcagcagctg gcttgctact     300
agcctcagca tgttttattt gctcaggatt gccaatttct ccaaccttat ttttcttcgc     360
ataaagagga gagttaagag tgttgttctg gtgatactgt tggggccttt gctattttg     420 gtttgtcatc ttttttgtgat aaacatggat gagactgtat ggacaaaaga atatgaagga    480
aacgtgactt ggaagatcaa attgaggagt gcaatgtacc attcaaatat gactctaacc    540

```
atgctagcaa actttgtacc cctcactctg accctgatat cttttctgct gttaatctgt    600
tctctgtgta acatctcaa gaagatgcag ctccatggca aaggatctca agatcccagc    660
accaaggtcc acataaaagc tttgcaaact gtgacctcct ttcttctgtt atgtgccatt    720
tactttctgt ccatgatcat atcagtttgt aattttggga ggctggaaaa gcaacctgtc    780
ttcatgttct gccaagctat tatattcagc tatccttcaa cccacccatt catcctgatt    840
ttgggaaaca agaagctaaa gcagattttt ctttcagttt tgcggcatgt gaggtactgg    900
gtgaaagaca gaagccttcg tctcca                                         926
```

<210> SEQ ID NO 19
<211> LENGTH: 298
<212> TYPE: PRT
<213> ORGANISM: Homo sapiens

<400> SEQUENCE: 19

```
Met Met Cys Phe Leu Leu Ile Ile Ser Ser Ile Leu Val Val Phe Ala
1               5                   10                  15

Phe Val Leu Gly Asn Val Ala Asn Gly Phe Ile Ala Leu Val Asn Val
                20                  25                  30

Ile Asp Trp Val Asn Thr Arg Lys Ile Ser Ser Ala Glu Gln Ile Leu
        35                  40                  45

Thr Ala Leu Val Val Ser Arg Ile Gly Leu Leu Trp Val Met Leu Phe
    50                  55                  60

Leu Trp Tyr Ala Thr Val Phe Asn Ser Ala Leu Tyr Gly Leu Glu Val
65                  70                  75                  80

Arg Ile Val Ala Ser Asn Ala Trp Ala Val Thr Asn His Phe Ser Met
                85                  90                  95

Trp Leu Ala Ala Ser Leu Ser Ile Phe Cys Leu Leu Lys Ile Ala Asn
            100                 105                 110

Phe Ser Asn Leu Ile Ser Leu His Leu Lys Lys Arg Ile Lys Ser Val
        115                 120                 125

Val Leu Val Ile Leu Leu Gly Pro Leu Val Phe Leu Ile Cys Asn Leu
    130                 135                 140

Ala Val Ile Thr Met Asp Glu Arg Val Trp Thr Lys Glu Tyr Glu Gly
145                 150                 155                 160

Asn Val Thr Trp Lys Ile Lys Leu Arg Asn Ala Ile His Leu Ser Ser
                165                 170                 175

Leu Thr Val Thr Thr Leu Ala Asn Leu Ile Pro Phe Thr Leu Ser Leu
            180                 185                 190

Ile Cys Phe Leu Leu Leu Ile Cys Ser Leu Cys Lys His Leu Lys Lys
        195                 200                 205

Met Arg Leu His Ser Lys Gly Ser Gln Asp Pro Ser Thr Lys Val His
    210                 215                 220

Ile Lys Ala Leu Gln Thr Val Thr Ser Phe Leu Met Leu Phe Ala Ile
225                 230                 235                 240

Tyr Phe Leu Cys Ile Ile Thr Ser Thr Trp Asn Leu Arg Thr Gln Gln
                245                 250                 255

Ser Lys Leu Val Leu Leu Cys Gln Thr Val Ala Ile Met Tyr Pro
            260                 265                 270

Ser Phe His Ser Phe Ile Leu Ile Met Gly Ser Arg Lys Leu Lys Gln
        275                 280                 285

Thr Phe Leu Ser Val Leu Trp Gln Met Thr
    290                 295
```

<210> SEQ ID NO 20
<211> LENGTH: 897
<212> TYPE: DNA
<213> ORGANISM: Homo sapiens

<400> SEQUENCE: 20

```
atgatgtgtt ttctgctcat catttcatca attctggtag tgtttgcatt tgttcttgga      60
aatgttgcca atggcttcat agccctagta aatgtcattg actgggttaa cacacgaaag     120
atctcctcag ctgagcaaat tctcactgct ctggtggtct ccagaattgg tttactctgg     180
gtcatgttat tcctttggta tgcaactgtg tttaattctg ctttatatgg tttagaagta     240
agaattgttg cttctaatgc ctgggctgta acgaaccatt tcagcatgtg gcttgctgct     300
agcctcagca tattttgttt gctcaagatt gccaatttct ccaaccttat ttctctccac     360
ctaaagaaga gaattaagag tgttgttctg gtgatactgt ggggccctt ggtattttg      420
atttgtaatc ttgctgtgat aaccatggat gagagagtgt ggacaaaaga atatgaagga     480
aatgtgactt ggaagatcaa attgaggaat gcaatacacc tttcaagctt gactgtaact     540
actctagcaa acctcatacc ctttactctg agcctaatat gttttctgct gttaatctgt     600
tctctttgta acatctcaa gaagatgcgg ctccatagca aaggatctca agatcccagc      660
accaaggtcc atataaaagc tttgcaaact gtgacctcct tcctcatgtt atttgccatt     720
tactttctgt gtataatcac atcaacttgg aatcttagga cacagcagag caaacttgta     780
ctcctgcttt gccaaactgt tgcaatcatg tatccttcat ccactcatt catcctgatt      840
atgggaagta ggaagctaaa acagaccttt ctttcagttt tgtggcagat gacacgc        897
```

<210> SEQ ID NO 21
<211> LENGTH: 309
<212> TYPE: PRT
<213> ORGANISM: Homo sapiens

<400> SEQUENCE: 21

```
Met Met Ser Phe Leu His Ile Val Phe Ser Ile Leu Val Val Val Ala
1               5                   10                  15

Phe Ile Leu Gly Asn Phe Ala Asn Gly Phe Ile Ala Leu Ile Asn Phe
            20                  25                  30

Ile Ala Trp Val Lys Arg Gln Lys Ile Ser Ser Ala Asp Gln Ile Ile
        35                  40                  45

Ala Ala Leu Ala Val Ser Lys Val Gly Leu Leu Trp Val Ile Leu Leu
    50                  55                  60

His Trp Tyr Ser Thr Val Leu Asn Pro Thr Ser Ser Asn Leu Lys Val
65                  70                  75                  80

Ile Ile Phe Ile Ser Asn Ala Trp Ala Val Thr Asn His Phe Ser Ile
                85                  90                  95

Trp Leu Ala Thr Ser Leu Ser Ile Phe Tyr Leu Leu Lys Ile Val Asn
            100                 105                 110

Phe Ser Arg Leu Ile Phe His His Leu Lys Arg Lys Ala Lys Ser Val
        115                 120                 125

Val Leu Val Ile Val Leu Gly Ser Leu Phe Phe Leu Val Cys His Leu
    130                 135                 140

Val Met Lys His Thr Tyr Ile Asn Val Trp Thr Glu Glu Cys Glu Gly
145                 150                 155                 160

Asn Val Thr Trp Lys Ile Lys Leu Arg Asn Ala Met His Leu Ser Asn
                165                 170                 175

Leu Thr Val Ala Met Leu Ala Asn Leu Ile Pro Phe Thr Leu Thr Leu
            180                 185                 190
```

Ile Ser Phe Leu Leu Leu Ile Tyr Ser Leu Cys Lys His Leu Lys Lys
            195                 200                 205

Met Gln Leu His Gly Lys Gly Ser Gln Asp Pro Ser Thr Lys Ile His
        210                 215                 220

Ile Lys Ala Leu Gln Thr Val Thr Ser Phe Leu Ile Leu Leu Ala Ile
225                 230                 235                 240

Tyr Phe Leu Cys Leu Ile Ile Ser Phe Trp Asn Phe Lys Met Arg Pro
                245                 250                 255

Lys Glu Ile Val Leu Met Leu Cys Gln Ala Phe Gly Ile Ile Tyr Pro
            260                 265                 270

Ser Phe His Ser Phe Ile Leu Ile Trp Gly Asn Lys Thr Leu Lys Gln
        275                 280                 285

Thr Phe Leu Ser Val Leu Trp Gln Val Thr Cys Trp Ala Lys Gly Gln
        290                 295                 300

Asn Gln Ser Thr Pro
305

<210> SEQ ID NO 22
<211> LENGTH: 927
<212> TYPE: DNA
<213> ORGANISM: Homo sapiens

<400> SEQUENCE: 22
atgatgagtt ttctacacat tgttttttcc attctagtag tggttgcatt tattcttgga      60
aattttgcca atggctttat agcactgata aatttcattg cctgggtcaa gagacaaaag     120
atctcctcag ctgatcaaat tattgctgct ctggcagtct ccaaagttgg tttgctctgg     180
gtaatattat tacattggta ttcaactgtg ttgaatccaa cttcatctaa tttaaaagta     240
ataattttta tttctaatgc ctgggcagta accaatcatt tcagcatctg gcttgctact     300
agcctcagca tatttatttt gctcaagatc gtcaatttct ccagacttat ttttcatcac     360
ttaaaaagga aggctaagag tgtagttctg gtgatagtgt tggggtcttt gttcttttg     420 gtttgtcacc ttgtgatgaa acacacgtat ataaatgtgt ggacagaaga atgtgaagga     480
aacgtaactt ggaagatcaa actgaggaat gcaatgcacc tttccaactt gactgtagcc     540
atgctagcaa acttgatacc attcactctg accctgatat cttttctgct gttaatctac     600
tctctgtgta acatctgaa gaagatgcag ctccatggca aaggatctca agatcccagc     660
accaagatcc acataaaagc tctgcaaact gtgacctcct tcctcatatt acttgccatt     720
tactttctgt gtctaatcat atcgttttgg aattttaaga tgcgaccaaa agaaattgtc     780
ttaatgcttt gccaagcttt tggaatcata tatccatcat tccactcatt cattctgatt     840
tgggggaaca agacgctaaa gcagaccttt ctttcagttt tgtggcaggt gacttgctgg     900
gcaaaggaca gaaccagtc aactcca                                           927

<210> SEQ ID NO 23
<211> LENGTH: 299
<212> TYPE: PRT
<213> ORGANISM: Homo sapiens

<400> SEQUENCE: 23

Met Ile Thr Phe Leu Tyr Ile Phe Ser Ile Leu Ile Met Val Leu
1                5                  10                  15

Phe Val Leu Gly Asn Phe Ala Asn Gly Phe Ile Ala Leu Val Asn Phe
                20                  25                  30

Ile Asp Trp Val Lys Arg Lys Lys Ile Ser Ser Ala Asp Gln Ile Leu

```
                         35                  40                  45
Thr Ala Leu Ala Val Ser Arg Ile Gly Leu Leu Trp Ala Leu Leu Leu
 50                  55                  60

Asn Trp Tyr Leu Thr Val Leu Asn Pro Ala Phe Tyr Ser Val Glu Leu
 65                  70                  75                  80

Arg Ile Thr Ser Tyr Asn Ala Trp Val Val Thr Asn His Phe Ser Met
                 85                  90                  95

Trp Leu Ala Ala Asn Leu Ser Ile Phe Tyr Leu Lys Ile Ala Asn
            100                 105                 110

Phe Ser Asn Leu Leu Phe Leu His Leu Lys Arg Arg Val Arg Ser Val
            115                 120                 125

Ile Leu Val Ile Leu Leu Gly Thr Leu Ile Phe Leu Val Cys His Leu
130                 135                 140

Leu Val Ala Asn Met Asp Glu Ser Met Trp Ala Glu Glu Tyr Glu Gly
145                 150                 155                 160

Asn Met Thr Gly Lys Met Lys Leu Arg Asn Thr Val His Leu Ser Tyr
                165                 170                 175

Leu Thr Val Thr Thr Leu Trp Ser Phe Ile Pro Phe Thr Leu Ser Leu
            180                 185                 190

Ile Ser Phe Leu Met Leu Ile Cys Ser Leu Tyr Lys His Leu Lys Lys
            195                 200                 205

Met Gln Leu His Gly Glu Gly Ser Gln Asp Leu Ser Thr Lys Val His
210                 215                 220

Ile Lys Ala Leu Gln Thr Leu Ile Ser Phe Leu Leu Cys Ala Ile
225                 230                 235                 240

Phe Phe Leu Phe Leu Ile Val Ser Val Trp Ser Pro Arg Arg Leu Arg
                245                 250                 255

Asn Asp Pro Val Val Met Val Ser Lys Ala Val Gly Asn Ile Tyr Leu
            260                 265                 270

Ala Phe Asp Ser Phe Ile Leu Ile Trp Arg Thr Lys Lys Leu Lys His
            275                 280                 285

Thr Phe Leu Leu Ile Leu Cys Gln Ile Arg Cys
290                 295

<210> SEQ ID NO 24
<211> LENGTH: 897
<212> TYPE: DNA
<213> ORGANISM: Homo sapiens

<400> SEQUENCE: 24
atgataactt ttctatacat tttttttttca attctaataa tggtttttatt tgttctcgga    60 aactttgcca atggcttcat agcactggta aatttcattg actgggtgaa gagaaaaaag   120
atctcctcag ctgaccaaat tctcactgct ctggcggtct ccagaattgg tttgctctgg   180
gcattattat taaattggta tttaactgtg ttgaatccag cttttatag tgtagaatta   240 agaattactt cttataatgc ctgggttgta accaaccatt tcagcatgtg gcttgctgct   300
aacctcagca tatttatttt gctcaagatt gccaatttct ccaaccttct ttttcttcat   360
ttaaagagga gagttaggag tgtcattctg gtgatactgt tggggacttt gatattttg    420 gtttgtcatc ttcttgtggc aaacatggat gagagtatg gggcagaaga atatgaagga   480
aacatgactg ggaagatgaa attgaggaat acagtacatc tttcatattt gactgtaact   540 acccctatgga gcttcatacc ctttactctg tccctgatat cttttctgat gctaatctgt   600
tctctgtata aacatctcaa gaagatgcag ctccatggag aaggatcgca agatctcagc   660
```

```
accaaggtcc acataaaagc tttgcaaact ctgatctcct tcctcttgtt atgtgccatt      720
ttctttctat tcctaatcgt ttcggtttgg agtcctagga ggctgcggaa tgacccagtt      780
gtcatggtta gcaaggctgt tggaaacata tatcttgcat tcgactcatt catcctaatt      840
tggagaacca agaagctaaa acacaccttt cttttgattt tgtgtcagat taggtgc         897
```

<210> SEQ ID NO 25
<211> LENGTH: 299
<212> TYPE: PRT
<213> ORGANISM: Homo sapiens

<400> SEQUENCE: 25

```
Met Leu Glu Ser His Leu Ile Ile Tyr Phe Leu Leu Ala Val Ile Gln
1               5                   10                  15

Phe Leu Leu Gly Ile Phe Thr Asn Gly Ile Ile Val Val Val Asn Gly
            20                  25                  30

Ile Asp Leu Ile Lys His Arg Lys Met Ala Pro Leu Asp Leu Leu Leu
        35                  40                  45

Ser Cys Leu Ala Val Ser Arg Ile Phe Leu Gln Leu Phe Ile Phe Tyr
    50                  55                  60

Val Asn Val Ile Val Phe Phe Ile Glu Phe Ile Met Cys Ser Ala
65                  70                  75                  80

Asn Cys Ala Ile Leu Leu Phe Ile Asn Glu Leu Glu Leu Trp Leu Ala
                85                  90                  95

Thr Trp Leu Gly Val Phe Tyr Cys Ala Lys Val Ala Ser Val Arg His
            100                 105                 110

Pro Leu Phe Ile Trp Leu Lys Met Arg Ile Ser Lys Leu Val Pro Trp
        115                 120                 125

Met Ile Leu Gly Ser Leu Leu Tyr Val Ser Met Ile Cys Val Phe His
    130                 135                 140

Ser Lys Tyr Ala Gly Phe Met Val Pro Tyr Phe Leu Arg Lys Phe Phe
145                 150                 155                 160

Ser Gln Asn Ala Thr Ile Gln Lys Glu Asp Thr Leu Ala Ile Gln Ile
                165                 170                 175

Phe Ser Phe Val Ala Glu Phe Ser Val Pro Leu Leu Ile Phe Leu Phe
            180                 185                 190

Ala Val Leu Leu Leu Ile Phe Ser Leu Gly Arg His Thr Arg Gln Met
        195                 200                 205

Arg Asn Thr Val Ala Gly Ser Arg Val Pro Gly Arg Gly Ala Pro Ile
    210                 215                 220

Ser Ala Leu Leu Ser Ile Leu Ser Phe Leu Ile Leu Tyr Phe Ser His
225                 230                 235                 240

Cys Met Ile Lys Val Phe Leu Ser Leu Lys Phe His Ile Arg Arg
                245                 250                 255

Phe Ile Phe Leu Phe Phe Ile Leu Val Ile Gly Ile Tyr Pro Ser Gly
            260                 265                 270

His Ser Leu Ile Leu Ile Leu Gly Asn Pro Lys Leu Lys Gln Asn Ala
        275                 280                 285

Lys Lys Phe Leu Leu His Ser Lys Cys Cys Gln
    290                 295
```

<210> SEQ ID NO 26
<211> LENGTH: 897
<212> TYPE: DNA
<213> ORGANISM: Homo sapiens

<400> SEQUENCE: 26

```
atgctagagt ctcacctcat tatctatttt cttcttgcag tgatacaatt tcttcttggg      60
attttcacaa atggcatcat tgtggtggtg aatggcattg acttgatcaa gcacagaaaa     120
atggctccgc tggatctcct tctttcttgt ctggcagttt ctagaatttt tctgcagttg     180
ttcatcttct acgttaatgt gattgttatc ttccttcatag aattcatcat gtgttctgcg    240
aattgtgcaa ttctcttatt tataaatgaa ttggaacttt ggcttgccac atggctcggc     300
gttttctatt gtgccaaggt tgccagcgtc cgtcacccac tcttcatctg gttgaagatg     360
aggatatcca agctggtccc atggatgatc ctggggtctc tgctatatgt atctatgatt     420
tgtgttttcc atagcaaata tgcagggttt atggtcccat acttcctaag gaaattttc     480 tcccaaaatg ccacaattca aaagaagat acactggcta tacagatttt ctcttttgtt     540
gctgagttct cagtgccatt gcttatcttc cttttttgctg ttttgctctt gattttctct    600
ctggggaggc acacccggca atgagaaac acagtggccg gcagcagggt tcctggcagg     660
ggtgcaccca tcagcgcgtt gctgtctatc ctgtccttcc tgatcctcta cttctcccac    720
tgcatgataa aagttttttct ctcttctcta aagtttcaca tcagaaggtt catctttctg    780
ttcttcatcc ttgtgattgg tatatacct tctggacact ctctcatctt aattttagga    840
aatcctaaat tgaaacaaaa tgcaaaaaag ttcctcctcc acagtaagtg ctgtcag       897

<210> SEQ ID NO 27
<211> LENGTH: 299
<212> TYPE: PRT
<213> ORGANISM: Homo sapiens

<400> SEQUENCE: 27

Met Leu Arg Leu Phe Tyr Phe Ser Ala Ile Ile Ala Ser Val Ile Leu
1               5                   10                  15

Asn Phe Val Gly Ile Ile Met Asn Leu Phe Ile Thr Val Val Asn Cys
            20                  25                  30

Lys Thr Trp Val Lys Ser His Arg Ile Ser Ser Ser Asp Arg Ile Leu
        35                  40                  45

Phe Ser Leu Gly Ile Thr Arg Phe Leu Met Leu Gly Leu Phe Leu Val
    50                  55                  60

Asn Thr Ile Tyr Phe Val Ser Ser Asn Thr Glu Arg Ser Val Tyr Leu
65                  70                  75                  80

Ser Ala Phe Phe Val Leu Cys Phe Met Phe Leu Asp Ser Ser Val
                85                  90                  95

Trp Phe Val Thr Leu Leu Asn Ile Leu Tyr Cys Val Lys Ile Thr Asn
            100                 105                 110

Phe Gln His Ser Val Phe Leu Leu Leu Lys Arg Asn Ile Ser Pro Lys
        115                 120                 125

Ile Pro Arg Leu Leu Leu Ala Cys Val Leu Ile Ser Ala Phe Thr Thr
    130                 135                 140

Cys Leu Tyr Ile Thr Leu Ser Gln Ala Ser Pro Phe Pro Glu Leu Val
145                 150                 155                 160

Thr Thr Arg Asn Asn Thr Ser Phe Asn Ile Ser Glu Gly Ile Leu Ser
                165                 170                 175

Leu Val Val Ser Leu Val Leu Ser Ser Ser Leu Gln Phe Ile Ile Asn
            180                 185                 190

Val Thr Ser Ala Ser Leu Leu Ile His Ser Leu Arg Arg His Ile Gln
        195                 200                 205

Lys Met Gln Lys Asn Ala Thr Gly Phe Trp Asn Pro Gln Thr Glu Ala
    210                 215                 220
```

His Val Gly Ala Met Lys Leu Met Val Tyr Phe Leu Ile Leu Tyr Ile
225                 230                 235                 240

Pro Tyr Ser Val Ala Thr Leu Val Gln Tyr Leu Pro Phe Tyr Ala Gly
            245                 250                 255

Met Asp Met Gly Thr Lys Ser Ile Cys Leu Ile Phe Ala Thr Leu Tyr
            260                 265                 270

Ser Pro Gly His Ser Val Leu Ile Ile Ile Thr His Pro Lys Leu Lys
        275                 280                 285

Thr Thr Ala Lys Lys Ile Leu Cys Phe Lys Lys
    290                 295

<210> SEQ ID NO 28
<211> LENGTH: 897
<212> TYPE: DNA
<213> ORGANISM: Homo sapiens

<400> SEQUENCE: 28
atgcttcggt tattctattt ctctgctatt attgcctcag ttattttaaa ttttgtagga      60
atcattatga atctgtttat tacagtggtc aattgcaaaa cttgggtcaa aagccataga    120
atctcctctt ctgataggat tctgttcagc ctgggcatca ccaggtttct tatgctggga    180
ctatttctgg tgaacaccat ctacttcgtc tcttcaaata cggaaaggtc agtctacctg    240
tctgcttttt ttgtgttgtg tttcatgttt ttggactcga gcagtgtctg gtttgtgacc    300
ttgctcaata tcttgtactg tgtgaagatt actaacttcc aacactcagt gtttctcctg    360
ctgaagcgga atatctcccc aaagatcccc aggctgctgc tggcctgtgt gctgatttct    420
gctttcacca cttgcctgta catcacgctt agccaggcat ccccttttcc tgaacttgtg    480
actacgagaa ataacacatc atttaatatc agtgagggca tcttgtcttt agtggtttct    540
ttggtcttga gctcatctct ccagttcatc attaatgtga cttctgcttc cttgctaata    600
cactccttga ggagacatat acagaagatg cagaaaaatg ccactggttt ctggaatccc    660
cagacggaag ctcatgtagg tgctatgaag ctgatggtct atttcctcat cctctacatt    720
ccatattcag ttgctaccct ggtccagtat ctcccctttt atgcagggat ggatatgggg    780
accaaatcca tttgtctgat ttttgccacc ctttactctc aggacattc tgttctcatt      840
attatcacac atcctaaact gaaaacaaca gcaagaaga ttctttgttt caaaaaa          897

<210> SEQ ID NO 29
<211> LENGTH: 299
<212> TYPE: PRT
<213> ORGANISM: Homo sapiens

<400> SEQUENCE: 29

Met Leu Ser Ala Gly Leu Gly Leu Leu Met Leu Val Ala Val Val Glu
1               5                   10                  15

Phe Leu Ile Gly Leu Ile Gly Asn Gly Ser Leu Val Val Trp Ser Phe
            20                  25                  30

Arg Glu Trp Ile Arg Lys Phe Asn Trp Ser Ser Tyr Asn Leu Ile Ile
        35                  40                  45

Leu Gly Leu Ala Gly Cys Arg Phe Leu Leu Gln Trp Leu Ile Ile Leu
    50                  55                  60

Asp Leu Ser Leu Phe Pro Leu Phe Gln Ser Ser Arg Trp Leu Arg Tyr
65                  70                  75                  80

Leu Ser Ile Phe Trp Val Leu Val Ser Gln Ala Ser Leu Trp Phe Ala
            85                  90                  95

Thr Phe Leu Ser Val Phe Tyr Cys Lys Lys Ile Thr Thr Phe Asp Arg
            100                 105                 110

Pro Ala Tyr Leu Trp Leu Lys Gln Arg Ala Tyr Asn Leu Ser Leu Trp
        115                 120                 125

Cys Leu Leu Gly Tyr Phe Ile Ile Asn Leu Leu Leu Thr Val Gln Ile
    130                 135                 140

Gly Leu Thr Phe Tyr His Pro Pro Gln Gly Asn Ser Ser Ile Arg Tyr
145                 150                 155                 160

Pro Phe Glu Ser Trp Gln Tyr Leu Tyr Ala Phe Gln Leu Asn Ser Gly
                165                 170                 175

Ser Tyr Leu Pro Leu Val Val Phe Leu Val Ser Ser Gly Met Leu Ile
            180                 185                 190

Val Ser Leu Tyr Thr His His Lys Lys Met Lys Val His Ser Ala Gly
        195                 200                 205

Arg Arg Asp Val Arg Ala Lys Ala His Ile Thr Ala Leu Lys Ser Leu
210                 215                 220

Gly Cys Phe Leu Leu Leu His Leu Val Tyr Ile Met Ala Ser Pro Phe
225                 230                 235                 240

Ser Ile Thr Ser Lys Thr Tyr Pro Pro Asp Leu Thr Ser Val Phe Ile
                245                 250                 255

Trp Glu Thr Leu Met Ala Ala Tyr Pro Ser Leu His Ser Leu Ile Leu
            260                 265                 270

Ile Met Gly Ile Pro Arg Val Lys Gln Thr Cys Gln Lys Ile Leu Trp
        275                 280                 285

Lys Thr Val Cys Ala Arg Arg Cys Trp Gly Pro
290                 295

<210> SEQ ID NO 30
<211> LENGTH: 897
<212> TYPE: DNA
<213> ORGANISM: Homo sapiens

<400> SEQUENCE: 30
atgctgagcg ctggcctagg actgctgatg ctggtggcag tggttgaatt tctcatcggt     60
ttaattggaa atggaagcct ggtggtctgg agttttagag aatggatcag aaaattcaac    120
tggtcctcat ataacctcat tatcctgggc ctggctggct gccgatttct cctgcagtgg    180
ctgatcattt tggacttaag cttgtttcca cttttccaga gcagccgttg gcttcgctat    240
cttagtatct tctgggtcct ggtaagccag gccagcttat ggtttgccac cttcctcagt    300
gtcttctatt gcaagaagat cacgaccttc gatcgcccgg cctacttgtg gctgaagcag    360
agggcctata acctgagtct ctggtgcctt ctgggctact ttataatcaa tttgttactt    420
acagtccaaa ttggcttaac attctatcat cctccccaag aaacagcag cattcggtat    480 ccctttgaaa gctggcagta cctgtatgca tttcagctca attcaggaag ttatttgcct    540
ttagtggtgt tcttgtttc ctctgggatg ctgattgtct ctttgtatac acaccacaag    600
aagatgaagg tccattcagc tggtaggagg gatgtccggg ccaaggctca catcactgcg    660
ctgaagtcct tgggctgctt cctcttactt cacctggttt atatcatggc cagccccttc    720
tccatcacct ccaagactta tcctcctgat ctcaccagtg tcttcatctg ggagacactc    780
atggcagcct atccttctct tcattctctc atattgatca tggggattcc tagggtgaag    840
cagacttgtc agaagatcct gtggaagacg gtgtgtgctc ggagatgctg ggccca       897

<210> SEQ ID NO 31
<211> LENGTH: 318

<212> TYPE: PRT
<213> ORGANISM: Homo sapiens

<400> SEQUENCE: 31

Met Ala Asp Lys Val Gln Thr Thr Leu Leu Phe Leu Ala Val Gly Glu
1               5                   10                  15

Phe Ser Val Gly Ile Leu Gly Asn Ala Phe Ile Gly Leu Val Asn Cys
            20                  25                  30

Met Asp Trp Val Lys Lys Arg Lys Ile Ala Ser Ile Asp Leu Ile Leu
        35                  40                  45

Thr Ser Leu Ala Ile Ser Arg Ile Cys Leu Leu Cys Val Ile Leu Leu
    50                  55                  60

Asp Cys Phe Ile Leu Val Leu Tyr Pro Asp Val Tyr Ala Thr Gly Lys
65                  70                  75                  80

Glu Met Arg Ile Ile Asp Phe Phe Trp Thr Leu Thr Asn His Leu Ser
                85                  90                  95

Ile Trp Phe Ala Thr Cys Leu Ser Ile Tyr Tyr Phe Phe Lys Ile Gly
            100                 105                 110

Asn Phe Phe His Pro Leu Phe Leu Trp Met Lys Trp Arg Ile Asp Arg
        115                 120                 125

Val Ile Ser Trp Ile Leu Leu Gly Cys Val Val Leu Ser Val Phe Ile
    130                 135                 140

Ser Leu Pro Ala Thr Glu Asn Leu Asn Ala Asp Phe Arg Phe Cys Val
145                 150                 155                 160

Lys Ala Lys Arg Lys Thr Asn Leu Thr Trp Ser Cys Arg Val Asn Lys
                165                 170                 175

Thr Gln His Ala Ser Thr Lys Leu Phe Leu Asn Leu Ala Thr Leu Leu
            180                 185                 190

Pro Phe Cys Val Cys Leu Met Ser Phe Phe Leu Leu Ile Leu Ser Leu
        195                 200                 205

Arg Arg His Ile Arg Arg Met Gln Leu Ser Ala Thr Gly Cys Arg Asp
    210                 215                 220

Pro Ser Thr Glu Ala His Val Arg Ala Leu Lys Ala Val Ile Ser Phe
225                 230                 235                 240

Leu Leu Leu Phe Ile Ala Tyr Tyr Leu Ser Phe Leu Ile Ala Thr Ser
                245                 250                 255

Ser Tyr Phe Met Pro Glu Thr Glu Leu Ala Val Ile Phe Gly Glu Ser
            260                 265                 270

Ile Ala Leu Ile Tyr Pro Ser Ser His Ser Phe Ile Leu Ile Leu Gly
        275                 280                 285

Asn Asn Lys Leu Arg His Ala Ser Leu Lys Val Ile Trp Lys Val Met
    290                 295                 300

Ser Ile Leu Lys Gly Arg Lys Phe Gln Gln His Lys Gln Ile
305                 310                 315

<210> SEQ ID NO 32
<211> LENGTH: 954
<212> TYPE: DNA
<213> ORGANISM: Homo sapiens

<400> SEQUENCE: 32
atggcagata aagtgcagac tactttattg ttcttagcag ttggagagtt ttcagtgggg     60
atcttaggga atgcattcat tggattggta aactgcatgg actgggtcaa gaagaggaaa    120
attgcctcca ttgatttaat cctcacaagt ctggccatat ccagaatttg tctattgtgc    180
gtaatactat tagattgttt tatattggtg ctatatccag atgtctatgc cactggtaaa    240

-continued

```
gaaatgagaa tcattgactt cttctggaca ctaaccaatc atttaagtat ctggtttgca    300
acctgcctca gcatttacta tttcttcaag ataggtaatt tctttcaccc acttttcctc    360
tggatgaagt ggagaattga cagggtgatt tcctggattc tactggggtg cgtggttctc    420
tctgtgttta ttagccttcc agccactgag aatttgaacg ctgatttcag gttttgtgtg    480
aaggcaaaga ggaaaacaaa cttaacttgg agttgcagag taaataaaac tcaacatgct    540
tctaccaagt tatttctcaa cctggcaacg ctgctcccct tttgtgtgtg cctaatgtcc    600
tttttcctct tgatcctctc cctgcggaga catatcaggc gaatgcagct cagtgccaca    660
gggtgcagag accccagcac agaagcccat gtgagagccc tgaaagctgt catttccttc    720
cttctcctct ttattgccta ctatttgtcc tttctcattg ccacctccag ctactttatg    780
ccagagacgg aattagctgt gattttggt gagtccatag ctctaatcta cccctcaagt    840
cattcattta tcctaatact ggggaacaat aaattaagac atgcatctct aaaggtgatt    900
tggaaagtaa tgtctattct aaaaggaaga aaattccaac aacataaaca aatc          954
```

<210> SEQ ID NO 33
<211> LENGTH: 309
<212> TYPE: PRT
<213> ORGANISM: Homo sapiens

<400> SEQUENCE: 33

```
Met Phe Ser Pro Ala Asp Asn Ile Phe Ile Ile Leu Ile Thr Gly Glu
1               5                   10                  15

Phe Ile Leu Gly Ile Leu Gly Asn Gly Tyr Ile Ala Leu Val Asn Trp
            20                  25                  30

Ile Asp Trp Ile Lys Lys Lys Ile Ser Thr Val Asp Tyr Ile Leu
        35                  40                  45

Thr Asn Leu Val Ile Ala Arg Ile Cys Leu Ile Ser Val Met Val Val
    50                  55                  60

Asn Gly Ile Val Ile Val Leu Asn Pro Asp Val Tyr Thr Lys Asn Lys
65                  70                  75                  80

Gln Gln Ile Val Ile Phe Thr Phe Trp Thr Phe Ala Asn Tyr Leu Asn
                85                  90                  95

Met Trp Ile Thr Thr Cys Leu Asn Val Phe Tyr Phe Leu Lys Ile Ala
            100                 105                 110

Ser Ser Ser His Pro Leu Phe Leu Trp Leu Lys Trp Lys Ile Asp Met
        115                 120                 125

Val Val His Trp Ile Leu Leu Gly Cys Phe Ala Ile Ser Leu Leu Val
    130                 135                 140

Ser Leu Ile Ala Ala Ile Val Leu Ser Cys Asp Tyr Arg Phe His Ala
145                 150                 155                 160

Ile Ala Lys His Lys Arg Asn Ile Thr Glu Met Phe His Val Ser Lys
                165                 170                 175

Ile Pro Tyr Phe Glu Pro Leu Thr Leu Phe Asn Leu Phe Ala Ile Val
            180                 185                 190

Pro Phe Ile Val Ser Leu Ile Ser Phe Phe Leu Leu Val Arg Ser Leu
        195                 200                 205

Trp Arg His Thr Lys Gln Ile Lys Leu Tyr Ala Thr Gly Ser Arg Asp
    210                 215                 220

Pro Ser Thr Glu Val His Val Arg Ala Ile Lys Thr Met Thr Ser Phe
225                 230                 235                 240

Ile Phe Phe Phe Phe Leu Tyr Tyr Ile Ser Ser Ile Leu Met Thr Phe
                245                 250                 255
```

Ser Tyr Leu Met Thr Lys Tyr Lys Leu Ala Val Glu Phe Gly Glu Ile
                260                 265                 270

Ala Ala Ile Leu Tyr Pro Leu Gly His Ser Leu Ile Leu Ile Val Leu
            275                 280                 285

Asn Asn Lys Leu Arg Gln Thr Phe Val Arg Met Leu Thr Cys Arg Lys
        290                 295                 300

Ile Ala Cys Met Ile
305

<210> SEQ ID NO 34
<211> LENGTH: 927
<212> TYPE: DNA
<213> ORGANISM: Homo sapiens

<400> SEQUENCE: 34

```
atgttcagtc ctgcagataa catctttata atcctaataa ctggagaatt catactagga      60
atattgggga atggatacat tgcactagtc aactggattg actggattaa gaagaaaaag     120
atttccacag ttgactacat ccttaccaat ttagttatcg ccagaatttg tttgatcagt     180
gtaatggttg taaatggcat tgtaatagta ctgaacccag atgtttatac aaaaaataaa     240
caacagatag tcattttttac cttctggaca tttgccaact acttaaatat gtggattacc     300
acctgcctta atgtcttcta ttttctgaag atagccagtt cctctcatcc acttttttctc    360
tggctgaagt ggaaaattga tatggtggtg cactggatcc tgctgggatg ctttgccatt    420
tccttgttgg tcagccttat agcagcaata gtactgagtt gtgattatag gtttcatgca    480
attgccaaac ataaaagaaa cattactgaa atgttccatg tgagtaaaat accatacttt    540
gaacccttaa ctctctttaa cctgtttgca attgtcccat ttattgtgtc actgatatca    600
ttttttcctttt tagtaagatc tttatggaga cataccaagc aaataaaact ctatgctacc    660
ggcagtagag accccagcac agaagttcat gtgagagcca ttaaaactat gacttcatttt    720
atcttctttt tttttcctata ctatattttct tctattttga tgacctttag ctatcttatg    780
acaaaataca agttagctgt ggagtttgga gagattgcag caattctcta cccccttggt    840
cactcactta ttttaattgt ttaaaataat aaactgaggc agacatttgt cagaatgctg    900
acatgtagaa aaattgcctg catgata                                         927
```

<210> SEQ ID NO 35
<211> LENGTH: 312
<212> TYPE: PRT
<213> ORGANISM: Homo sapiens

<400> SEQUENCE: 35

Met Pro Ser Ala Ile Glu Ala Ile Tyr Ile Ile Leu Ile Ala Gly Glu
1               5                   10                  15

Leu Thr Ile Gly Ile Trp Gly Asn Gly Phe Ile Val Leu Val Asn Cys
            20                  25                  30

Ile Asp Trp Leu Lys Arg Arg Asp Ile Ser Leu Ile Asp Ile Ile Leu
        35                  40                  45

Ile Ser Leu Ala Ile Ser Arg Ile Cys Leu Leu Cys Val Ile Ser Leu
    50                  55                  60

Asp Gly Phe Phe Met Leu Leu Phe Pro Gly Thr Tyr Gly Asn Ser Val
65                  70                  75                  80

Leu Val Ser Ile Val Asn Val Val Trp Thr Phe Ala Asn Asn Ser Ser
                85                  90                  95

Leu Trp Phe Thr Ser Cys Leu Ser Ile Phe Tyr Leu Leu Lys Ile Ala

```
                 100                 105                 110
Asn Ile Ser His Pro Phe Phe Trp Leu Lys Leu Lys Ile Asn Lys
            115                 120                 125
Val Met Leu Ala Ile Leu Leu Gly Ser Phe Leu Ile Ser Leu Ile Ile
        130                 135                 140
Ser Val Pro Lys Asn Asp Asp Met Trp Tyr His Leu Phe Lys Val Ser
145                 150                 155                 160
His Glu Glu Asn Ile Thr Trp Lys Phe Lys Val Ser Lys Ile Pro Gly
                165                 170                 175
Thr Phe Lys Gln Leu Thr Leu Asn Leu Gly Val Met Val Pro Phe Ile
            180                 185                 190
Leu Cys Leu Ile Ser Phe Phe Leu Leu Phe Ser Leu Val Arg His
        195                 200                 205
Thr Lys Gln Ile Arg Leu His Ala Thr Gly Phe Arg Asp Pro Ser Thr
210                 215                 220
Glu Ala His Met Arg Ala Ile Lys Ala Val Ile Ile Phe Leu Leu Leu
225                 230                 235                 240
Leu Ile Val Tyr Tyr Pro Val Phe Leu Val Met Thr Ser Ser Ala Leu
                245                 250                 255
Ile Pro Gln Gly Lys Leu Val Leu Met Ile Gly Asp Ile Val Thr Val
            260                 265                 270
Ile Phe Pro Ser Ser His Ser Phe Leu Ile Met Gly Asn Ser Lys
        275                 280                 285
Leu Arg Glu Ala Phe Leu Lys Met Leu Arg Phe Val Lys Cys Phe Leu
    290                 295                 300
Arg Arg Arg Lys Pro Phe Val Pro
305                 310

<210> SEQ ID NO 36
<211> LENGTH: 936
<212> TYPE: DNA
<213> ORGANISM: Homo sapiens

<400> SEQUENCE: 36
atgccaagtg caatagaggc aatatatatt attttaattg ctggtgaatt gaccataggg      60
atttggggaa atggattcat tgtactagtt aactgcattg actggctcaa aagaagagat     120
atttccttga ttgacatcat cctgatcagc ttggccatct ccagaatctg tctgctgtgt     180
gtaatatcat tagatggctt ctttatgctg ctctttccag gtacatatgg caatagcgtg     240
ctagtaagca ttgtgaatgt tgtctggaca tttgccaata attcaagtct ctggtttact     300
tcttgcctca gtatcttcta tttactcaag atagccaata tatcgcaccc attttcttc     360
tggctgaagc taaagatcaa caaggtcatg cttgcgattc ttctgggtc cttttcttatc     420
tctttaatta ttagtgttcc aaagaatgat gatatgtggt atcacctttt caaagtcagt     480
catgaagaaa acattacttg gaaattcaaa gtgagtaaaa ttccaggtac tttcaaacag     540
ttaaccctga acctgggggt gatggttccc tttatccttt gcctgatctc attttcttg     600
ttactttcct ccctagttag acacaccaag cagattcgac tgcatgctac agggttcaga     660
gaccccagta cagaggccca catgagggcc ataaaggcag tgatcatctt tctgctcctc     720
ctcatcgtgt actacccagt ctttcttgtt atgacctcta gcgctctgat tcctcaggga     780
aaattagtgt tgatgattgg tgacatagta actgtcattt tcccatcaag ccattcattc     840
attctaatta tgggaaatag caagttgagg gaagctttc tgaagatgtt aagatttgtg     900
aagtgtttcc ttagaagaag aaagcctttt gttcca                               936
```

<210> SEQ ID NO 37
<211> LENGTH: 307
<212> TYPE: PRT
<213> ORGANISM: Homo sapiens

<400> SEQUENCE: 37

Met Leu Arg Val Val Glu Gly Ile Phe Ile Phe Val Val Ser Glu
1               5                   10                  15

Ser Val Phe Gly Val Leu Gly Asn Gly Phe Ile Gly Leu Val Asn Cys
            20                  25                  30

Ile Asp Cys Ala Lys Asn Lys Leu Ser Thr Ile Gly Phe Ile Leu Thr
        35                  40                  45

Gly Leu Ala Ile Ser Arg Ile Phe Leu Ile Trp Ile Ile Thr Asp
50                  55                  60

Gly Phe Ile Gln Ile Phe Ser Pro Asn Ile Tyr Ala Ser Gly Asn Leu
65                  70                  75                  80

Ile Glu Tyr Ile Ser Tyr Phe Trp Val Ile Gly Asn Gln Ser Ser Met
                85                  90                  95

Trp Phe Ala Thr Ser Leu Ser Ile Phe Tyr Phe Leu Lys Ile Ala Asn
            100                 105                 110

Phe Ser Asn Tyr Ile Phe Leu Trp Leu Lys Ser Arg Thr Asn Met Val
        115                 120                 125

Leu Pro Phe Met Ile Val Phe Leu Leu Ile Ser Ser Leu Leu Asn Phe
130                 135                 140

Ala Tyr Ile Ala Lys Ile Leu Asn Asp Tyr Lys Met Lys Asn Asp Thr
145                 150                 155                 160

Val Trp Asp Leu Asn Met Tyr Lys Ser Glu Tyr Phe Ile Lys Gln Ile
                165                 170                 175

Leu Leu Asn Leu Gly Val Ile Phe Phe Phe Thr Leu Ser Leu Ile Thr
            180                 185                 190

Cys Ile Phe Leu Ile Ile Ser Leu Trp Arg His Asn Arg Gln Met Gln
        195                 200                 205

Ser Asn Val Thr Gly Leu Arg Asp Ser Asn Thr Glu Ala His Val Lys
210                 215                 220

Ala Met Lys Val Leu Ile Ser Phe Ile Ile Leu Phe Ile Leu Tyr Phe
225                 230                 235                 240

Ile Gly Met Ala Ile Glu Ile Ser Cys Phe Thr Val Arg Glu Asn Lys
                245                 250                 255

Leu Leu Leu Met Phe Gly Met Thr Thr Thr Ala Ile Tyr Pro Trp Gly
            260                 265                 270

His Ser Phe Ile Leu Ile Leu Gly Asn Ser Lys Leu Lys Gln Ala Ser
        275                 280                 285

Leu Arg Val Leu Gln Gln Leu Lys Cys Cys Glu Lys Arg Lys Asn Leu
290                 295                 300

Arg Val Thr
305

<210> SEQ ID NO 38
<211> LENGTH: 921
<212> TYPE: DNA
<213> ORGANISM: Homo sapiens

<400> SEQUENCE: 38
atgctacgtg tagtggaagg catcttcatt tttgttgtag ttagtgagtc agtgtttggg      60
gttttgggga atggatttat tggacttgta aactgcattg actgtgccaa gaataagtta     120

```
tctacgattg gctttattct caccggctta gctatttcaa gaattttttct gatatggata    180 ataattacag atggatttat acagatattc tctccaaata tatatgcctc cggtaaccta    240
attgaatata ttagttactt ttgggtaatt ggtaatcaat caagtatgtg gtttgccacc    300
agcctcagca tcttctattt cctgaagata gcaaattttt ccaactacat atttctctgg    360
ttgaagagca gaacaaatat ggttcttccc ttcatgatag tattcttact tatttcatcg    420
ttacttaatt ttgcatacat tgcgaagatt cttaatgatt ataaaatgaa gaatgacaca    480
gtctgggatc tcaacatgta taaaagtgaa tactttatta acagattttt gctaaatctg    540
ggagtcattt tcttctttac actatcccta attacatgta ttttttttaat catttcccctt    600 tggagacaca acaggcagat gcaatcgaat gtgacaggat tgagagactc caacacagaa    660
gctcatgtga aggcaatgaa agttttgata tctttcatca tcctctttat cttgtatttt    720
ataggcatgg ccatagaaat atcatgtttt actgtgcgag aaaacaaact gctgcttatg    780
tttggaatga caaccacagc catctatccc tggggtcact catttatctt aattctagga    840
aacagcaagc taaagcaagc ctctttgagg gtactgcagc aattgaagtg ctgtgagaaa    900
aggaaaaatc tcagagtcac a                                            921
```

<210> SEQ ID NO 39
<211> LENGTH: 303
<212> TYPE: PRT
<213> ORGANISM: Homo sapiens

<400> SEQUENCE: 39

```
Met Glu Ser Ala Leu Pro Ser Ile Phe Thr Leu Val Ile Ile Ala Glu
1               5                   10                  15

Phe Ile Ile Gly Asn Leu Ser Asn Gly Phe Ile Val Leu Ile Asn Cys
            20                  25                  30

Ile Asp Trp Val Ser Lys Arg Glu Leu Ser Ser Val Asp Lys Leu Leu
        35                  40                  45

Ile Ile Leu Ala Ile Ser Arg Ile Gly Leu Ile Trp Glu Ile Leu Val
    50                  55                  60

Ser Trp Phe Leu Ala Leu His Tyr Leu Ala Ile Phe Val Ser Gly Thr
65                  70                  75                  80

Gly Leu Arg Ile Met Ile Phe Ser Trp Ile Val Ser Asn His Phe Asn
                85                  90                  95

Leu Trp Leu Ala Thr Ile Phe Ser Ile Phe Tyr Leu Leu Lys Ile Ala
            100                 105                 110

Ser Phe Ser Ser Pro Ala Phe Leu Tyr Leu Lys Trp Arg Val Asn Lys
        115                 120                 125

Val Ile Leu Met Ile Leu Leu Gly Thr Leu Val Phe Leu Phe Leu Asn
    130                 135                 140

Leu Ile Gln Ile Asn Met His Ile Lys Asp Trp Leu Asp Arg Tyr Glu
145                 150                 155                 160

Arg Asn Thr Thr Trp Asn Phe Ser Met Ser Asp Phe Glu Thr Phe Ser
                165                 170                 175

Val Ser Val Lys Phe Thr Met Thr Met Phe Ser Leu Thr Pro Phe Thr
            180                 185                 190

Val Ala Phe Ile Ser Phe Leu Leu Ile Phe Ser Leu Gln Lys His
        195                 200                 205

Leu Gln Lys Met Gln Leu Asn Tyr Lys Gly His Arg Asp Pro Arg Thr
    210                 215                 220

Lys Val His Thr Asn Ala Leu Lys Ile Val Ile Ser Phe Leu Leu Phe
```

```
                225                 230                 235                 240
Tyr Ala Ser Phe Phe Leu Cys Val Leu Ile Ser Trp Ile Ser Glu Leu
                    245                 250                 255

Tyr Gln Ser Thr Val Ile Tyr Met Leu Cys Glu Thr Ile Gly Val Phe
                260                 265                 270

Ser Pro Ser Ser His Ser Phe Leu Leu Ile Leu Gly Asn Ala Lys Leu
                275                 280                 285

Arg Gln Ala Phe Leu Leu Val Ala Ala Lys Val Trp Ala Lys Arg
        290                 295                 300

<210> SEQ ID NO 40
<211> LENGTH: 909
<212> TYPE: DNA
<213> ORGANISM: Homo sapiens

<400> SEQUENCE: 40
atggaaagtg ccctgccgag tatcttcact cttgtaataa ttgcagaatt cataattggg      60
aatttgagca atggatttat agtactgatc aactgcattg actgggtcag taaaagagag     120
ctgtcctcag tcgataaact cctcattatc ttggcaatct ccagaattgg gctgatctgg     180
gaaatattag taagttggtt tttagctctg cattatctag ccatatttgt gtctggaaca     240
ggattaagaa ttatgatttt tagctggata gtttctaatc acttcaatct ctggcttgct     300
acaatcttca gcatctttta tttgctcaaa atagcgagtt tctctagccc tgcttttctc     360
tatttgaagt ggagagtaaa caaagtgatt ctgatgatac tgctaggaac cttggtcttc     420
ttattttaa atctgataca aataaacatg catataaaag actggctgga ccgatatgaa     480
agaaacacaa cttggaattt cagtatgagt gactttgaaa cattttcagt gtcggtcaaa     540
ttcactatga ctatgttcag tctaacacca tttactgtgg ccttcatctc ttttctcctg     600
ttaattttct ccctgcagaa acatctccag aaaatgcaac tcaattacaa aggacacaga     660
gaccccagga ccaaggtcca tacaaatgcc ttgaaaattg tgatctcatt cctttattc     720
tatgctagtt tctttctatg tgttctcata tcatggattt ctgagctgta tcagagcaca     780
gtgatctaca tgctttgtga gacgattgga gtcttctctc cttcaagcca ctcctttctt     840
ctgattctag gaacgctaa gttaagacag gcctttcttt tggtggcagc taaggtatgg     900
gctaaacga                                                             909

<210> SEQ ID NO 41
<211> LENGTH: 317
<212> TYPE: PRT
<213> ORGANISM: Homo sapiens

<400> SEQUENCE: 41

Met Gly Gly Val Ile Lys Ser Ile Phe Thr Phe Val Leu Ile Val Glu
1               5                   10                  15

Phe Ile Ile Gly Asn Leu Gly Asn Ser Phe Ile Ala Leu Val Asn Cys
                20                  25                  30

Ile Asp Trp Val Lys Gly Arg Lys Ile Ser Ser Val Asp Arg Ile Leu
            35                  40                  45

Thr Ala Leu Ala Ile Ser Arg Ile Ser Leu Val Trp Leu Ile Phe Gly
        50                  55                  60

Ser Trp Cys Val Ser Val Phe Phe Pro Ala Leu Phe Ala Thr Glu Lys
65                  70                  75                  80

Met Phe Arg Met Leu Thr Asn Ile Trp Thr Val Ile Asn His Phe Ser
                85                  90                  95
```

```
Val Trp Leu Ala Thr Gly Leu Gly Thr Phe Tyr Leu Lys Ile Ala
            100                 105                 110

Asn Phe Ser Asn Ser Ile Phe Leu Tyr Leu Lys Trp Arg Val Lys Lys
        115                 120                 125

Val Val Leu Val Leu Leu Leu Val Thr Ser Val Phe Leu Phe Leu Asn
130                 135                 140

Ile Ala Leu Ile Asn Ile His Ile Asn Ala Ser Ile Asn Gly Tyr Arg
145                 150                 155                 160

Arg Asn Lys Thr Cys Ser Ser Asp Ser Ser Asn Phe Thr Arg Phe Ser
                165                 170                 175

Ser Leu Ile Val Leu Thr Ser Thr Val Phe Ile Phe Ile Pro Phe Thr
            180                 185                 190

Leu Ser Leu Ala Met Phe Leu Leu Leu Ile Phe Ser Met Trp Lys His
        195                 200                 205

Arg Lys Lys Met Gln His Thr Val Lys Ile Ser Gly Asp Ala Ser Thr
210                 215                 220

Lys Ala His Arg Gly Val Lys Ser Val Ile Thr Phe Phe Leu Leu Tyr
225                 230                 235                 240

Ala Ile Phe Ser Leu Ser Phe Phe Ile Ser Val Trp Thr Ser Glu Arg
                245                 250                 255

Leu Glu Glu Asn Leu Ile Ile Leu Ser Gln Val Met Gly Met Ala Tyr
            260                 265                 270

Pro Ser Cys His Ser Cys Val Leu Ile Leu Gly Asn Lys Lys Leu Arg
        275                 280                 285

Gln Ala Ser Leu Ser Val Leu Leu Trp Leu Arg Tyr Met Phe Lys Asp
290                 295                 300

Gly Glu Pro Ser Gly His Lys Glu Phe Arg Glu Ser Ser
305                 310                 315

<210> SEQ ID NO 42
<211> LENGTH: 951
<212> TYPE: DNA
<213> ORGANISM: Homo sapiens

<400> SEQUENCE: 42
atgggtggtg tcataaagag catatttaca ttcgttttaa ttgtggaatt tataattgga      60
aatttaggaa atagtttcat agcactggtg aactgtattg actgggtcaa gggaagaaag     120
atctcttcgg ttgatcggat cctcactgct ttggcaatct ctcgaattag cctggtttgg     180
ttaatattcg gaagctggtg tgtgtctgtg ttttccccag cttttatttgc cactgaaaaa     240 atgttcagaa tgcttactaa tatctggaca gtgatcaatc attttagtgt ctggttagct     300
acaggcctcg gtactttta ttttctcaag atagccaatt tttctaactc tatttttctc     360
tacctaaagt ggagagttaa aaaggtggtt ttggtgctgc ttcttgtgac ttcggtcttc     420 ttgttttta atattgcact gataaacatc catataaatg ccagtatcaa tggatacaga     480
agaaacaaga cttgcagttc tgattcaagt aactttacac gattttccag tcttattgta     540
ttaaccagca ctgtgttcat tttcataccc tttactttgt ccctggcaat gtttcttctc     600
ctcatcttct ccatgtggaa acatcgcaag aagatgcagc acactgtcaa aatatccgga     660
gacgccagca ccaaagccca cagaggagtt aaaagtgtga tcactttctt cctactctat     720
gccattttct ctctgtcttt tttcatatca gtttggacct ctgaaaggtt ggaggaaaat     780
ctaattattc tttcccaggt gatgggaatg gcttatcctt catgtcactc atgtgttctg     840
attcttggaa acaagaagct gagacaggcc tctctgtcag tgctactgtg gctgaggtac     900
```
atgttcaaag atgggagcc ctcaggtcac aaagaattta gagaatcatc t              951

<210> SEQ ID NO 43
<211> LENGTH: 291
<212> TYPE: PRT
<213> ORGANISM: Homo sapiens

<400> SEQUENCE: 43

Met Ile Pro Ile Gln Leu Thr Val Phe Phe Met Ile Ile Tyr Val Leu
1               5                   10                  15

Glu Ser Leu Thr Ile Ile Val Gln Ser Ser Leu Ile Val Ala Val Leu
            20                  25                  30

Gly Arg Glu Trp Leu Gln Val Arg Arg Leu Met Pro Val Asp Met Ile
        35                  40                  45

Leu Ile Ser Leu Gly Ile Ser Arg Phe Cys Leu Gln Trp Ala Ser Met
    50                  55                  60

Leu Asn Asn Phe Cys Ser Tyr Phe Asn Leu Asn Tyr Val Leu Cys Asn
65                  70                  75                  80

Leu Thr Ile Thr Trp Glu Phe Phe Asn Ile Leu Thr Phe Trp Leu Asn
                85                  90                  95

Ser Leu Leu Thr Val Phe Tyr Cys Ile Lys Val Ser Ser Phe Thr His
            100                 105                 110

His Ile Phe Leu Trp Leu Arg Trp Arg Ile Leu Arg Leu Phe Pro Trp
        115                 120                 125

Ile Leu Leu Gly Ser Leu Met Ile Thr Cys Val Thr Ile Ile Pro Ser
    130                 135                 140

Ala Ile Gly Asn Tyr Ile Gln Ile Gln Leu Leu Thr Met Glu His Leu
145                 150                 155                 160

Pro Arg Asn Ser Thr Val Thr Asp Lys Leu Glu Asn Phe His Gln Tyr
                165                 170                 175

Gln Phe Gln Ala His Thr Val Ala Leu Val Ile Pro Phe Ile Leu Phe
            180                 185                 190

Leu Ala Ser Thr Ile Phe Leu Met Ala Ser Leu Thr Lys Gln Ile Gln
        195                 200                 205

His His Ser Thr Gly His Cys Asn Pro Ser Met Lys Ala His Phe Thr
    210                 215                 220

Ala Leu Arg Ser Leu Ala Val Leu Phe Ile Val Phe Thr Ser Tyr Phe
225                 230                 235                 240

Leu Thr Ile Leu Ile Thr Ile Ile Gly Thr Leu Phe Asp Lys Arg Cys
                245                 250                 255

Trp Leu Trp Val Trp Glu Ala Phe Val Tyr Ala Phe Ile Leu Met His
            260                 265                 270

Ser Thr Ser Leu Met Leu Ser Ser Pro Thr Leu Lys Arg Ile Leu Lys
        275                 280                 285

Gly Lys Cys
    290

<210> SEQ ID NO 44
<211> LENGTH: 873
<212> TYPE: DNA
<213> ORGANISM: Homo sapiens

<400> SEQUENCE: 44
atgataccca tccaactcac tgtcttcttc atgatcatct atgtgcttga gtccttgaca      60
attattgtgc agagcagcct aattgttgca gtgctgggca gagaatggct gcaagtcaga     120
aggctgatgc ctgtggacat gattctcatc agcctgggca tctctcgctt ctgtctacag     180

```
tgggcatcaa tgctgaacaa ttttttgctcc tattttaatt tgaattatgt actttgcaac      240
ttaacaatca cctgggaatt ttttaatatc cttacattct ggttaaacag cttgcttacc      300
gtgttctact gcatcaaggt ctcttctttc acccatcaca tctttctctg gctgaggtgg      360
agaattttga ggttgtttcc ctggatatta ctgggttctc tgatgattac ttgtgtaaca      420
atcatccctt cagctattgg gaattacatt caaattcagt tactcaccat ggagcatcta      480
ccaagaaaca gcactgtaac tgacaaactt gaaaatttc atcagtatca gttccaggct      540
catacagttg cattggttat tcctttcatc ctgttcctgg cctccaccat ctttctcatg      600
gcatcactga ccaagcagat acaacatcat agcactggtc actgcaatcc aagcatgaaa      660
gcgcacttca ctgccctgag gtcccttgcc gtcttattta ttgtgtttac ctcttacttt      720
ctaaccatac tcatcaccat tataggtact ctatttgata agagatgttg gttatgggtc      780
tgggaagctt ttgtctatgc tttcatctta atgcattcca cttcactgat gctgagcagc      840
cctacgttga aaaggattct aagggaaagt gc                                    873
```

<210> SEQ ID NO 45
<211> LENGTH: 316
<212> TYPE: PRT
<213> ORGANISM: Homo sapiens

<400> SEQUENCE: 45

```
Met Met Gly Leu Thr Glu Gly Val Phe Leu Ile Leu Ser Gly Thr Gln
1               5                   10                  15

Phe Thr Leu Gly Ile Leu Val Asn Cys Phe Ile Glu Leu Val Asn Gly
            20                  25                  30

Ser Ser Trp Phe Lys Thr Lys Arg Met Ser Leu Ser Asp Phe Ile Ile
        35                  40                  45

Thr Thr Leu Ala Leu Leu Arg Ile Ile Leu Leu Cys Ile Ile Leu Thr
    50                  55                  60

Asp Ser Phe Leu Ile Glu Phe Ser Pro Asn Thr His Asp Ser Gly Ile
65                  70                  75                  80

Ile Met Gln Ile Ile Asp Val Ser Trp Thr Phe Thr Asn His Leu Ser
                85                  90                  95

Ile Trp Leu Ala Thr Cys Leu Gly Val Leu Tyr Cys Leu Lys Ile Ala
            100                 105                 110

Ser Phe Ser His Pro Thr Phe Leu Trp Leu Lys Trp Arg Val Ser Arg
        115                 120                 125

Val Met Val Trp Met Leu Leu Gly Ala Leu Leu Ser Cys Gly Ser
    130                 135                 140

Thr Ala Ser Leu Ile Asn Glu Phe Lys Leu Tyr Ser Val Phe Arg Gly
145                 150                 155                 160

Ile Glu Ala Thr Arg Asn Val Thr Glu His Phe Arg Lys Lys Arg Ser
                165                 170                 175

Glu Tyr Tyr Leu Ile His Val Leu Gly Thr Leu Trp Tyr Leu Pro Pro
            180                 185                 190

Leu Ile Val Ser Leu Ala Ser Tyr Ser Leu Leu Ile Phe Ser Leu Gly
        195                 200                 205

Arg His Thr Arg Gln Met Leu Gln Asn Gly Thr Ser Ser Arg Asp Pro
    210                 215                 220

Thr Thr Glu Ala His Lys Arg Ala Ile Arg Ile Ile Leu Ser Phe Phe
225                 230                 235                 240

Phe Leu Phe Leu Leu Tyr Phe Leu Ala Phe Leu Ile Ala Ser Phe Gly
                245                 250                 255
```

Asn Phe Leu Pro Lys Thr Lys Met Ala Lys Met Ile Gly Glu Val Met
            260                 265                 270

Thr Met Phe Tyr Pro Ala Gly His Ser Phe Ile Leu Ile Leu Gly Asn
            275                 280                 285

Ser Lys Leu Lys Gln Thr Phe Val Val Met Leu Arg Cys Glu Ser Gly
            290                 295                 300

His Leu Lys Pro Gly Ser Lys Gly Pro Ile Phe Ser
305                 310                 315

<210> SEQ ID NO 46
<211> LENGTH: 948
<212> TYPE: DNA
<213> ORGANISM: Homo sapiens

<400> SEQUENCE: 46

```
atgatgggac tcaccgaggg ggtgttcctg attctgtctg gcactcagtt cacactggga      60
attctggtca attgtttcat tgagttggtc aatggtagca gctggttcaa gaccaagaga     120
atgtctttgt ctgacttcat catcaccacc ctggcactct gaggatcat tctgctgtgt      180
attatcttga ctgatagttt tttaatagaa ttctctccca acacacatga ttcagggata     240
ataatgcaaa ttattgatgt ttcctggaca tttacaaacc atctgagcat tggcttgcc      300
acctgtcttg gtgtcctcta ctgcctgaaa atcgccagtt tctctcaccc acattcctc     360
tggctcaagt ggagagtttc tagggtgatg gtatggatgc tgttgggtgc actgctctta     420
tcctgtggta gtaccgcatc tctgatcaat gagtttaagc tctattctgt ctttagggga     480
attgaggcca ccaggaatgt gactgaacac ttcagaaaga gaggagtga gtattatctg      540
atccatgttc ttgggactct gtggtacctg cctcccttaa ttgtgtccct ggcctcctac     600
tctttgctca tcttctccct ggggaggcac acacggcaga tgctgcaaaa tgggacaagc     660
tccagagatc caaccactga ggcccacaag agggccatca gaatcatcct tccttcttc     720
tttctcttct tactttactt tcttgctttc ttaattgcat catttggtaa tttcctacca     780
aaaaccaaga tggctaagat gattggcgaa gtaatgacaa tgttttatcc tgctggccac     840
tcatttattc tcattctggg gaacagtaag ctgaagcaga catttgtagt gatgctccgg     900
tgtgagtctg gtcatctgaa gcctggatcc aagggaccca ttttctct                  948
```

<210> SEQ ID NO 47
<211> LENGTH: 314
<212> TYPE: PRT
<213> ORGANISM: Homo sapiens

<400> SEQUENCE: 47

Met Ala Thr Glu Leu Asp Lys Ile Phe Leu Ile Leu Ala Ile Ala Glu
1               5                   10                  15

Phe Ile Ile Ser Met Leu Gly Asn Val Phe Ile Gly Leu Val Asn Cys
            20                  25                  30

Ser Glu Gly Ile Lys Asn Gln Lys Val Phe Ser Ala Asp Phe Ile Leu
            35                  40                  45

Thr Cys Leu Ala Ile Ser Thr Ile Gly Gln Leu Leu Val Ile Leu Phe
        50                  55                  60

Asp Ser Phe Leu Val Gly Leu Ala Ser His Leu Tyr Thr Thr Tyr Arg
65                  70                  75                  80

Leu Gly Lys Thr Val Ile Met Leu Trp His Met Thr Asn His Leu Thr
            85                  90                  95

Thr Trp Leu Ala Thr Cys Leu Ser Ile Phe Tyr Phe Phe Lys Ile Ala

```
              100                 105                 110
His Phe Pro His Ser Leu Phe Leu Trp Leu Arg Trp Arg Met Asn Gly
            115                 120                 125

Met Ile Val Met Leu Leu Ile Leu Ser Leu Phe Leu Leu Ile Phe Asp
        130                 135                 140

Ser Leu Val Leu Glu Ile Phe Ile Asp Ile Ser Leu Asn Ile Ile Asp
145                 150                 155                 160

Lys Ser Asn Leu Thr Leu Tyr Leu Asp Glu Ser Lys Thr Leu Phe Asp
                165                 170                 175

Lys Leu Ser Ile Leu Lys Thr Leu Leu Ser Leu Thr Ser Phe Ile Pro
            180                 185                 190

Phe Ser Leu Ser Leu Thr Ser Leu Leu Phe Leu Phe Leu Ser Leu Val
        195                 200                 205

Arg His Thr Arg Asn Leu Lys Leu Ser Ser Leu Gly Ser Arg Asp Ser
210                 215                 220

Ser Thr Glu Ala His Arg Arg Ala Met Lys Met Val Met Ser Phe Leu
225                 230                 235                 240

Phe Leu Phe Ile Val His Phe Phe Ser Leu Gln Val Ala Asn Trp Ile
            245                 250                 255

Phe Phe Met Leu Trp Asn Asn Lys Tyr Ile Lys Phe Val Met Leu Ala
        260                 265                 270

Leu Asn Ala Phe Pro Ser Cys His Ser Phe Ile Leu Ile Leu Gly Asn
                275                 280                 285

Ser Lys Leu Arg Gln Thr Ala Val Arg Leu Leu Trp His Leu Arg Asn
        290                 295                 300

Tyr Thr Lys Thr Pro Asn Ala Leu Pro Leu
305                 310

<210> SEQ ID NO 48
<211> LENGTH: 942
<212> TYPE: DNA
<213> ORGANISM: Homo sapiens

<400> SEQUENCE: 48
atggccaccg aattggacaa atctttctg attctggcaa tagcagaatt catcatcagc      60
atgctgggga atgtgttcat tggactggta aactgctctg aagggatcaa gaaccaaaag    120
gtcttctcag ctgacttcat cctcacctgc ttggctatct ccacaattgg acaactgttg    180
gtgatactgt ttgattcatt tctagtggga cttgcttcac atttatatac acatataga    240 ctaggaaaaa ctgttattat gctttggcac atgactaatc acttgacaac ctggcttgcc    300
acctgcctaa gcattttcta tttctttaag atagcccact ccccactc ccttttcctc     360 tggctgaggt ggaggatgaa cggaatgatt gttatgcttc ttatattgtc tttgttctta    420 ctgattttg acagtttagt gctagaaata tttattgata tctcactcaa tataatagat    480
aaaagtaatc tgactttata tttagatgaa agtaaaactc tctttgataa actctctatt    540
ttaaaaactc ttctcagctt gaccagtttt atccccttt ctctgtccct gacctccttg     600 cttttttat ttctgtcctt ggtgagacat actagaaatt tgaagctcag ttccttgggc     660
tctagagact ccagcacaga ggcccatagg agggccatga aaatggtgat gtctttcctt    720
ttcctcttca tagttcattt ttttccttta caagtggcca attggatatt ttttatgttg    780
tggaacaaca gtacataaa gtttgtcatg ttagccttaa atgcctttcc ctcgtgccac     840
tcatttattc tcattctggg aaacagcaag ctgcgacaga cagctgtgag gctactgtgg    900
catcttagga actatacaaa aacaccaaat gctttaccct tg                       942
```

<210> SEQ ID NO 49
<211> LENGTH: 318
<212> TYPE: PRT
<213> ORGANISM: Homo sapiens

<400> SEQUENCE: 49

Met Asn Gly Asp His Met Val Leu Gly Ser Val Thr Asp Lys Lys
1               5                   10                  15

Ala Ile Ile Leu Val Thr Ile Leu Leu Leu Arg Leu Val Ala Ile
            20                  25                  30

Ala Gly Asn Gly Phe Ile Thr Ala Ala Leu Gly Val Glu Trp Val Leu
        35                  40                  45

Arg Arg Met Leu Leu Pro Cys Asp Lys Leu Leu Val Ser Leu Gly Ala
50                  55                  60

Ser Arg Phe Cys Leu Gln Ser Val Val Met Gly Lys Thr Ile Tyr Val
65                  70                  75                  80

Phe Leu His Pro Met Ala Phe Pro Tyr Asn Pro Val Leu Gln Phe Leu
                85                  90                  95

Ala Phe Gln Trp Asp Phe Leu Asn Ala Ala Thr Leu Trp Ser Ser Thr
            100                 105                 110

Trp Leu Ser Val Phe Tyr Cys Val Lys Ile Ala Thr Phe Thr His Pro
        115                 120                 125

Val Phe Phe Trp Leu Lys His Lys Leu Ser Gly Trp Leu Pro Trp Met
130                 135                 140

Leu Phe Ser Ser Val Gly Leu Ser Ser Phe Thr Thr Ile Leu Phe Phe
145                 150                 155                 160

Ile Gly Asn His Arg Met Tyr Gln Asn Tyr Leu Arg Asn His Leu Gln
                165                 170                 175

Pro Trp Asn Val Thr Gly Asp Ser Ile Arg Ser Tyr Cys Glu Lys Phe
            180                 185                 190

Tyr Leu Phe Pro Leu Lys Met Ile Thr Trp Thr Met Pro Thr Ala Val
        195                 200                 205

Phe Phe Ile Cys Met Ile Leu Leu Ile Thr Ser Leu Gly Arg His Arg
210                 215                 220

Lys Lys Ala Leu Leu Thr Thr Ser Gly Phe Arg Glu Pro Ser Val Gln
225                 230                 235                 240

Ala His Ile Lys Ala Leu Leu Ala Leu Leu Ser Phe Ala Met Leu Phe
                245                 250                 255

Ile Ser Tyr Phe Leu Ser Leu Val Phe Ser Ala Ala Gly Ile Phe Pro
            260                 265                 270

Pro Leu Asp Phe Lys Phe Trp Val Trp Glu Ser Val Ile Tyr Leu Cys
        275                 280                 285

Ala Ala Val His Pro Ile Ile Leu Leu Phe Ser Asn Cys Arg Leu Arg
290                 295                 300

Ala Val Leu Lys Ser Arg Arg Ser Ser Arg Cys Gly Thr Pro
305                 310                 315

<210> SEQ ID NO 50
<211> LENGTH: 957
<212> TYPE: DNA
<213> ORGANISM: Homo sapiens

<400> SEQUENCE: 50
atgaatggag accacatggt tctaggatct tcggtgactg acaagaaggc catcatcttg      60
gttaccattt tactcctttt acgcctggta gcaatagcag gcaatggctt catcactgct     120

```
gctctgggcg tggagtgggt gctacggaga atgttgttgc cttgtgataa gttattggtt    180
agcctagggg cctctcgctt ctgtctgcag tcagtggtaa tgggtaagac catttatgtt    240
ttcttgcatc cgatggcctt cccatacaac cctgtactgc agtttctagc tttccagtgg    300
gacttcctga atgctgccac cttatggtcc tctacctggc tcagtgtctt ctattgtgtg    360
aaaattgcta ccttcaccca ccctgtcttc ttctggctaa agcacaagtt gtctgggtgg    420
ctaccatgga tgctcttcag ctctgtaggg ctctccagct tcaccaccat tctattttc     480 ataggcaacc acagaatgta tcagaactat ttaaggaacc atctacaacc ttggaatgtc    540
actggcgata gcatacggag ctactgtgag aaattctatc tcttccctct aaaaatgatt    600
acttggacaa tgcccactgc tgtctttttc atttgcatga ttttgctcat cacatctctg    660
ggaagacaca ggaagaaggc tctccttaca acctcaggat tccgagagcc cagtgtgcag    720
gcacacataa aggctctgct ggctctcctc tcttttgcca tgctcttcat ctcatatttc    780
ctgtcactgg tgttcagtgc tgcaggtatt tttccacctc tggactttaa attctgggtg    840
tgggagtcag tgatttatct gtgtgcagca gttcacccca tcattctgct cttcagcaac    900
tgcaggctga gagctgtgct gaagagtcgt cgttcctcaa ggtgtgggac accttga       957

<210> SEQ ID NO 51
<211> LENGTH: 33
<212> TYPE: DNA
<213> ORGANISM: Artificial
<220> FEATURE:
<223> OTHER INFORMATION: Primer comprising EcoRI restriction site for
      PCR amplification of hTAS2R16

<400> SEQUENCE: 51
cctgggaatt ttttaatatc cttacattct ggt                                 33

<210> SEQ ID NO 52
<211> LENGTH: 19
<212> TYPE: DNA
<213> ORGANISM: Artificial
<220> FEATURE:
<223> OTHER INFORMATION: Primer comprising NotI restriction site for PCR
      amplification of hTAS2R16

<400> SEQUENCE: 52
gaagcgcgct ttcatgctt                                                 19
```

BITTER TASTE RECEPTORS

CROSS-REFERENCE TO RELATED APPLICATION

This application is a continuation application of application Ser. No. 12/168,551, filed Jul. 7, 2008; which is a divisional application of Ser. No. 10/528,630, filed Mar. 22, 2005, now U.S. Pat. No. 5,413,867; which is a National Stage Application of international Application Number PCT/EP2003/010691, filed Sep. 25, 2003; which claims the benefit of U.S. Provisional Application Ser. No. 60/413,298, filed Sep. 25, 2002, all of which are incorporated herein in their entirety.

BACKGROUND OF THE INVENTION

Investigators have recently turned their attention to understanding the biological mechanisms of taste, and in particular bitter taste. For a review of the literature see, for example, *Science* 291, 1557-1560. (2001); *Cell* 100, 607-610 (2000); *Neuron* 25, 507-510 (2000); *Nature* 413, 219-225. (2001); and *J. Biol. Chem.* 277, 1-4 (2001).

Bitter taste is aversive, and as such provides humans with a mechanism of protection against poisonous substances, which are generally bitter-tasting compounds. More subtly, bitter-tastants also affect the palatability of food, beverages, thereby influencing human nutritional habits as is more fully discussed by Drewnowski in "The Science and Complexity of Bitter Taste", *Nutr. Rev.* 59, 163-169 (2001). They also affect the palatability of other ingestibles such as orally administered pharmaceuticals and nutraceuticals. Understanding the mechanism of bitter taste transduction has implications for the food and pharmaceutical industries. If the bitter taste transduction pathway can be manipulated, it may be possible to suppress or eliminate bitter taste to render foods more palatable and increase patient compliance in oral pharmaceutics.

Taste transduction involves the interaction of molecules, i.e., tastants with taste receptor-expressing cells which reside in the taste buds located in the papillae of the tongue. Taste buds relay information to the brain on the nutrient content of food and the presence of poisons. Recent advances in biochemical and physiological studies have enabled researchers to conclude that bitter taste transduction is mediated by so-called G-protein coupled receptors (GPCRs). GPCRs are 7 transmembrane domain cell surface proteins that amplify signals generated at a cell surface when the receptor interacts with a ligand (a tastant) whereupon they activate heterotrimeric G-proteins. The G-proteins are protein complexes that are composed of alpha and beta-gamma subunits. They are usually referred to by their alpha subunits and classified generally into 4 groups: $G_{alpha\ s, i, q\ and\ 12}$. The $G_{alpha\ q}$ type couple with GPCRs to activate phospholipase C which leads to the increase in cellular $Ca^{2+}$. There are many $G_q$-type G-proteins that are promiscuous and can couple to GPCRs, including taste receptors, and these so-called "promiscuous" G-proteins are well known to the man skilled in the art. These G-proteins dissociate into alpha and beta-gamma subunits upon activation, resulting in a complex cascade of cellular events that results in the cell producing cell messengers, such as calcium ions, that enable the cells to send a signal to the brain indicating a bitter response.

There is also anatomical evidence that GPCRs mediate bitter taste transduction: clusters of these receptors are found in mammalian taste cells containing gustducin. Gustducin is a G-protein subunit that is implicated in the perception of bitter taste in mammals, see for example Chandrashekar, J. et al., *Cell* 100, 703-711 (2000); Matsunami H. et al., *Nature* 404, 601-604 (2000); or Adler E. et al., *Cell* 100, 693-702 (2000). cDNAs encoding such GPCRs have been identified, isolated, and used as templates to compare with DNA libraries using in-silico data-mining techniques to identify other related receptors. In this manner it has been possible to identify a family of related receptors, the so-called T2R family of receptors, that have been putatively assigned as bitter receptors.

To-date, however, it is not clear as to whether all the bitter taste receptors have been discovered. Further, of those that have been discovered, many have not been matched, or paired, with ligands, and applicant is aware of very few published studies wherein rigorous matching has been undertaken. Chandrashekar, J. et al. in *Cell* 100, 703-711 (2000), has expressed a human T2R receptor, the so-called hT2R4 receptor, in heterologous systems and looked at the in vitro response of this receptor. They found that it provided a response to the bitter compounds denatonium and 6-n-propyl-2-thiouracil. However, the concentrations of bitter tastants needed to activate the hT2R4 receptor were two orders of magnitude higher than the thresholds reported in human taste studies, and so it is not clear that the protein encoded by the hT2R4 gene is a functional bitter receptor. The authors of the Chandrashekar et al. article also looked at a number of mouse T2R receptors with a range of stock bitter-tasting chemicals of disparate chemical structure. However, no study has looked at receptor responses to bitter ligands that are problematic in the food and pharmaceutical industries, and means of suppressing the bitter response to these ligands.

The universe of compounds that provoke a bitter response in humans is structurally very diverse. Therefore, if research into bitter receptors is to be of any practical significance to the food and pharmaceutical industries, all bitter receptors will need to be identified, and once identified, there has to be a rigorous understanding of how specific receptors are matched to particular structural classes of bitter compounds. Unfortunately, although much basic research has been conducted in the area of bitter taste receptors, there are potentially many more bitter receptors to be discovered, and little is still known as to whether the known members of the human T2R family of bitter receptors actually respond to bitter tastants, and if so what, if any, specificity they show to ligand substructures.

BRIEF SUMMARY OF THE INVENTION

The present invention relates to bitter-taste receptors and their role in bitter taste transduction. The invention also relates to assays for screening molecules that modulate, e.g. suppress or block bitter taste transduction, or enhance bitter taste response.

DETAILED DESCRIPTION OF THE INVENTION

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., screening for compounds that inhibit bitter taste, will be apparent from the following description, from the drawings and from the claims.

Surprisingly, applicant has now found a new group of putative bitter taste receptors, and in respect of certain known bitter receptors, applicant has found that they respond with specificity towards classes of bitter compounds that are important in the food and pharmaceutical industries.

In a first aspect of the invention there is provided a new group of putative bitter receptors. The genetics of bitter tasting has been extensively studied in mice and rats. Therefore, applicant compared the nucleotide sequences encoding polypeptides previously proposed to be bitter receptors with publicly available human nucleic acid sequences in the NCBI database using the BLAST® search methodology (Parameters: Expect=0.01, Filter=default). Surprisingly, the search identified 24 DNA sequences (from human chromosomes 5, 7, and 12) that, because of their homology to a mouse nucleic acid sequence that encodes a polypeptide (T2R5) previously designated as a bitter receptor, we designated as bitter receptor-encoding. Bitter taste receptors were originally assigned identifiers starting with the three characters "T2R" (identifying the receptor family) followed by a number (e.g., 1, 2, 3, etc.) that identifies a particular receptor, e.g., T2R5. More recently a different system has been used in which the identifiers start with five characters "TAS2R" (identifying the receptor family) followed, as previously, by a number (e.g., 1, 2, 3, etc.) that identifies a particular receptor, e.g., TAS2R5. A lower case letter in front of the identifier indicates the species of the receptor (e.g., "h" for human, "r" for rat, and "m" for mouse). Thus, for example, mTAS2R5 is a mouse bitter receptor and hTAS2R2 is a human bitter receptor. For consistency the new TAS2R identifier system is used throughout the rest of this application.

Of the 24 coding sequences identified by the search, 12 are believed to be novel; the polypeptides encoded by these novel sequences are designated hTAS2R38-41, and 43-50. The DNA sequences encoding the polypeptides are assigned SEQ ID NOs: 2 (hTAS2R38), 4 (hTAS2R39), 6 (hTAS2R40), 8 (hTAS2R41), 10 (hTAS2R43), 12 (hTAS2R44), 14(hTAS2R45), 16 (hTAS2R46), 18 (hTAS2R47), 20 (hTAS2R48), 22 (hTAS2R49), and 24 (hTAS2R50), respectively, and the amino acid sequences of the polypeptides are assigned SEQ ID NOs: 1, 3, 5, 7, 9, 11, 13, 15, 17, 19, 21, and 23, respectively.

The 12 additional (possibly novel) sequences identified by the search encode polypeptides, which are designated hTAS2R1, 4, 5, 7-10, 13, 14, 16, 3, 42 and 60. The DNA sequences encoding the polypeptides are assigned SEQ ID NOs: 26 (hTAS2R1), 28 (hTAS2R4), 30 (hTAS2R5), 32 (hTAS2R7), 34 (hTAS2R8), 36 (hTAS2R9), 38 (hTAS2R10), 40 (hTAS2R13), 42 (hTAS2R14), 44 (hTAS2R16), 46 (hTAS2R3), 48 (hTAS2R42), and 50 (hTAS2R60), respectively, and the amino acid sequences of the polypeptides are assigned SEQ ID NOs: 25, 27, 29, 31, 33, 35, 37, 39, 41, 43, 45, 47 and 49, respectively.

Thus, one aspect of the present invention is a polynucleotide selected from the group consist ing of
(a) polynucleotides encoding at least the mature form of the polypeptide having the deduced amino acid sequence as shown in SEQ ID NOs 1, 3, 5, 7, 9, 11, 13, 15, 17, 19, 21, and 23;
(b) polynucleotides having the coding sequence, as shown in SEQ ID NOs: 2, 4, 6, 8, 10, 12, 14, 16, 18, 20, 22, and 24 encoding at least the mature form of the polypeptide;
(c) polynucleotides encoding a fragment or derivative of a polypeptide encoded by a polynucleotide of any one of (a) to (b), wherein in said derivative one or more amino acid residues are conservatively substituted compared to said polypeptide, and said fragment or derivative has bitter substance binding activity;
(d) polynucleotides which are at least 50% identical to a polynucleotide as defined in any one of (a) to (c) and which code for a polypeptide having bitter substance binding activity; and
(e) polynucleotides the complementary strand of which hybridizes, preferably under stringent conditions to a polynucleotide as defined in any one of (a) to (d) and which code for a polypeptide having bitter substance binding activity;
or the complementary strand of such a polynucleotide.

A polypeptide that exhibits bitter substance binding activity is a polypeptide that has at least 20% (e.g., at least: 20%; 30%; 40%; 50%; 60%; 70%; 80%; 90%; 95%; 98%; 99%; 99.5%; or 100% or even more) of the ability of the respective full-length TAS2R to bind to a given bitter substance. Binding assays and bitter substances are described herein below.

In a preferred embodiment the polynucleotide of the present invention encodes a polypeptide that still exhibits essentially the same activity as the respective mature bitter taste receptor, i.e. has "bitter taste receptor activity". Preferably the polypeptide has at least 20% (e.g., at least: 20%; 30%; 40%; 50%; 60%; 70%; 80%; 90%; 95%; 98%; 99%; 99.5%; or 100% or even more) of the ability of the respective full-length TAS2R to release intracellular calcium in a heterologous cell expression system like, for example, HEK293/15—cells, which stably express the alpha-subunit of promiscuous G-proteins, e.g. the mouse $G_{15}$ subunit, in response to bitter tastants, which is dependent on the expression of polypeptides encoded by the polynucleotides of the present invention. The amount of intracellular calcium release can be monitored by, for example, the in vitro FLIPR assay described herein below.

The TAS2R nucleic acid molecules of the invention can be DNA, cDNA, genomic DNA, synthetic DNA, or, RNA, and can be double-stranded or single-stranded, the sense and/or an antisense strand. Segments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription.

The polynucleotide molecules of the invention can contain naturally occurring sequences, or sequences that differ from those that occur naturally, but, due to the degeneracy of the genetic code, encode the same polypeptide (for example, the polypeptides with SEQ ID NOs: 1, 3, 5, 7, 9, 11, 13, 15, 17, 19, 21, and 23). In addition, these nucleic acid molecules are not limited to coding sequences, e.g., they can include some or all of the non-coding sequences that lie upstream or downstream from a coding sequence.

The polynucleotide molecules of the invention can be synthesized in vitro (for example, by phosphoramidite-based synthesis) or obtained from a cell, such as the cell of a bacteria mammal. The nucleic acids can be those of a human but also derived from a non-human primate, mouse, rat, guinea pig, cow, sheep, horse, pig, rabbit, dog, or cat as long as they fulfill the criteria set out above. Combinations or modifications of the nucleotides within these types of nucleic acids are also encompassed.

In addition, the isolated nucleic acid molecules of the invention encompass segments that are not found as such in the natural state. Thus, the invention encompasses recombinant nucleic acid molecules incorporated into a vector (for example, a plasmid or viral vector) or into the genome of a heterologous cell (or the genome of a homologous cell, at a position other than the natural chromosomal location). Recombinant nucleic acid molecules and uses therefore are discussed further below.

A polynucleotide belonging to a family of any of the TAS2R disclosed herein or a protein can be identified based on its similarity to the relevant TAS2R gene or protein, respectively. For example, the identification can be based on sequence identity. In certain preferred embodiments the invention features isolated nucleic acid molecules which are at least 50% (or 55%, 65%, 75%, 85°/a, 95%, or 98%) identical to (a) a nucleic acid molecule that encodes the polypeptide of SEQ ID NOs:1, 3, 5, 7, 9, 11, 13, 15, 17, 19, 21, or 23; (b) the nucleotide sequence of SEQ ID NOs: 2, 4, 6, 8, 10, 12, 14, 16, 18, 20, 22, or 24; and (c) a nucleic acid molecule which includes a segment of at least 30 (e.g., at least 30, 40, 50, 60, 80, 100, 125, 150, 175, 200, 250, 300, 400, 500, 600, 700, 800, 850, 900, 950, 1000, or 1010) nucleotides of SEQ ID NOs: 2, 4, 6, 8, 10, 12, 14, 16, 18, 20, 22, or 24.

The determination of percent identity between two sequences is accomplished using the mathematical algorithm of Karlin and Altschul, *Proc. Natl. Acad. Sci. USA* 90, 5873-5877, 1993. Such an algorithm is incorporated into the BLASTN and BLASTP programs of Altschul et al. (1990) J. Mol. Biol. 215, 403-410. BLAST nucleotide searches are performed with the BLASTN program, score=100, wordlength=12, to obtain nucleotide sequences homologous to HIN-1-encoding nucleic acids. BLAST protein searches are performed with the BLASTP program, score=50, wordlength=3, to obtain amino acid sequences homologous to the TAS2R polypeptide. To obtain gapped alignments for comparative purposes, Gapped BLAST is utilized as described in Altschul et al. (1997) Nucleic Acids Res. 25, 3389-3402. When utilizing BLAST and Gapped BLAST programs, the default parameters of the respective programs.

Hybridization can also be used as a measure of homology between two nucleic acid sequences. A nucleic acid sequence encoding any of the TAS2R disclosed herein, or a portion thereof, can be used as a hybridization probe according to standard hybridization techniques. The hybridization of a TAS2R probe to DNA or RNA from a test source (e.g., a mammalian cell) is an indication of the presence of the relevant TAS2R DNA or RNA in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

An "isolated DNA" is either (1) a DNA that contains sequence not identical to that of any naturally occurring sequence, or (2), in the context of a DNA with a naturally-occurring sequence (e.g., a cDNA or genomic DNA), a DNA free of at least one of the genes that flank the gene containing the DNA of interest in the genome of the organism in which the gene containing the DNA of interest naturally occurs. The term therefore includes a recombinant DNA incorporated into a vector, into an autonomously replicating plasmid or virus, or into the genomic DNA of a prokaryote or eukaryote. The term also includes a separate molecule such as a cDNA where the corresponding genomic DNA has introns and therefore a different sequence; a genomic fragment that lacks at least one of the flanking genes; a fragment of cDNA or genomic DNA produced by polymerase chain reaction (PCR) and that lacks at least one of the flanking genes; a restriction fragment that lacks at least one of the flanking genes; a DNA encoding a non-naturally occurring protein such as a fusion protein, mutein, or fragment of a given protein; and a nucleic acid which is a degenerate variant of a cDNA or a naturally occurring nucleic acid. In addition, it includes a recombinant nucleotide sequence that is part of a hybrid gene, i.e., a gene encoding a non-naturally occurring fusion protein. It will be apparent from the foregoing that isolated DNA does not mean a DNA present among hundreds to millions of other DNA molecules within, for example, cDNA or genomic DNA libraries or genomic DNA restriction digests in, for example, a restriction digest reaction mixture or an electrophoretic gel slice.

A further aspect of the present invention is a vector containing the polynucleotide(s) of the present invention or a protein encoded by a polynucleotide of the present invention The term "vector" refers to a protein or a polynucleotide or a mixture thereof which is capable of being introduced or of introducing the proteins and/or nucleic acid comprised into a cell. It is preferred that the proteins encoded by the introduced polynucleotide are expressed within the cell upon introduction of the vector.

In a preferred embodiment the vector of the present invention comprises plasmids, phagemids, phages, cosmids, artificial mammalian chromosomes, knock-out or knock-in constructs, viruses, in particular adenoviruses, vaccinia viruses, attenuated vaccinia viruses, canary pox viruses, lentivirus (Chang, L. J. and Gay, E. E. (20001) Curr. Gene Therap. 1:237-251), herpes viruses, in particular Herpes simplex virus (HSV-1, Carlezon, W. A. et al. (2000) Crit. Rev. Neurobiol.), baculovirus, retrovirus, adeno-associated-virus (AAV, Carter, P. J. and Samulski, R. J. (2000) J. Mol. Med. 6:17-27), rhinovirus, human immune deficiency virus (HIV), filovirus and engineered versions thereof (see, for example, Cobinger G. P. et al (2001) Nat. Biotechnol. 19:225-30), virosomes, "naked" DNA liposomes, and nucleic acid coated particles, in particular gold spheres. Particularly preferred are viral vectors like adenoviral vectors or retroviral vectors (Lindemann et al. (1997) Mol. Med. 3:466-76 and Springer et al. (1998) Mol. Cell. 2:549-58). Liposomes are usually small unilamellar or multilamellar vesicles made of cationic, neutral and/or anionic lipids, for example, by ultrasound treatment of liposomal suspensions. The DNA can, for example, be ionically bound to the surface of the liposomes or internally enclosed in the liposome. Suitable lipid mixtures are known in the art and comprise, for example, DOTMA (1,2-Dioleyloxpropyl-3-trimethylammoniumbromid) and DPOE (Dioleoylphosphatidyl-ethanolamin) which both have been used on a variety of cell lines.

Nucleic acid coated particles are another means for the introduction of nucleic acids into cells using so called "gene guns", which allow the mechanical introduction of particles into the cells. Preferably the particles itself are inert, and therefore, are in a preferred embodiment made out of gold spheres.

In a further aspect the polynucleotide of the present invention is operatively linked to expression control sequences allowing expression in prokaryotic and/or eukaryotic host cells. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include but are not limited to regulatory elements directing constitutive expression like, for example, promoters transcribed by RNA polymerase III like, e.g., promoters for the snRNA U6 or scRNA 7SK gene, the cytomegalovirus hCMV immediate early gene, the early or late promoters of SV40 adenovirus, viral promoter and activator sequences derived from, e.g., NBV, HCV, HSV, HPV, EBV, HTLV, or HIV; which allow inducible expression like, for example, CUP-1 promoter, the tet-repressor as employed, for example, in the tet-on or tet-off systems, the lac system, the trp system; regulatory elements directing tissue specific expression, preferably taste bud specific expression, e.g., PLCβ2 promoter or gustducin promoter, regulatory elements directing cell cycle specific expression like, for example, cdc2, cdc25C or cyclin A; or the TAC system, the TRC system, the major operator and promoter regions of phage A, the control regions of fd coat protein, the promoter for 3-phosphoglycerate kinase, the promoters of acid phosphatase, and the promoters of the yeast α- or α-mating factors.

As used herein, "operatively linked" means incorporated into a genetic construct so that expression control sequences effectively control expression of a coding sequence of interest.

Similarly, the polynucleotides of the present invention can form part of a hybrid gene encoding additional polypeptide sequences, for example, a sequence that functions as a marker or reporter. Examples of marker and reporter genes include β-lactamase, chloramphenicol acetyltransferase (CAT), adenosine deammase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, additional sequences that can serve the function of a marker or reporter. Generally, the hybrid polypeptide will include a first portion and a second portion; the first portion being a TAS2R polypeptide and the second portion being, for example, the reporter described above or an Ig constant region or part of an Ig constant region, e.g., the CH2 and CH3 domains of IgG2a heavy chain. Other hybrids could include an antigenic tag or His tag to facilitate purification and/or detection. Recombinant nucleic acid molecules can also contain a polynucleotide sequence encoding a TAS2R polypeptide operatively linked to a heterologous signal sequence. Such signal sequences can direct the protein to different compartments within the cell and are well known to someone of skill in the art. A preferred signal sequence is a sequence that facilitates secretion of the resulting protein.

Another aspect of the present invention is a host cell genetically engineered with the polynucleotide or the vector as outlined above. The host cells that may be used for purposes of the invention include but are not limited to prokaryotic cells such as bacteria (for example, *E. coli* and *B. subtilis*), which can be transformed with, for example, recombinant bacteriophage DNA, plasmid DNA, or cosmid DNA expression vectors containing the polynucleotide molecules of the invention; simple eukaryotic cells like yeast (for example, *Saccharomyces* and *Pichia*), which can be transformed with, for example, recombinant yeast expression vectors containing the polynucleotide molecule of the invention; insect cell systems like, for example, Sf9 of Hi5 cells, which can be infected with, for example, recombinant virus expression vectors (for example, baculovirus) containing the polynucleotide molecules of the invention; *Xenopus* oocytes, which can be injected with, for example, plasmids; plant cell systems, which can be infected with, for example, recombinant virus expression vectors (for example, cauliflower mosaic virus (CaMV) or tobacco mosaic virus (TMV)) or transformed with recombinant plasmid expression vectors (for example, Ti plasmid) containing a TAS2R nucleotide sequence; or mammalian cell systems (for example, COS, CHO, BHK, HEK293, VERO, HeLa, MDCK, Wi38, and NIH 3T3 cells), which can be transformed with recombinant expression constructs containing, for example, promoters derived, for example, from the genome of mammalian cells (for example, the metallothionein promoter) from mammalian vi ruses (for example, the adenovirus late promoter and the vaccinia virus 7.5K promoter) or from bacterial cells (for example, the tet-repressor binding its employed in the tet-on and tet-off systems). Also useful as host cells are primary or secondary cells obtained directly from a mammal and transfected with a plasmid vector or infected with a viral vector. Depending on the host cell and the respective vector used to introduce the polynucleotide of the invention the polynucleotide can integrate, for example, into the chromosome or the mitochondrial DNA or can be maintained extrachromosomally like, for example, episomally or can be only transiently comprised in the cells.

In a preferred embodiment, the TAS2R encoded by the polynucleotides of the present invention and which are expressed by such cells are functional, i.e., upon binding to one or more bitter molecules they trigger an activation pathway in the cell. The cells are preferably mammalian (e.g., human, non-human primate, horse, bovine, sheep, goat, pig, dog, cat, goat, rabbit, mouse, rat, guinea pig, hamster, or gerbil) cells, insect cells, bacterial cells, or fungal (including yeast) cells.

A further aspect of the present invention is a transgenic non-human animal containing a polynucleotide, a vector and/or a host cell as described above. The animal can be a mosaic animal, which means that only part of the cells making up the body comprise polynucleotides, vectors, and/or cells of the present invention or the animal can be a transgenic animal which means that all cells of the animal comprise the polynucleotides and/or vectors of the present invention or are derived from a cell of the present invention. Mosaic or transgenic animals can be either homo- or heterozygous with respect to the polynucleotides of the present invention contained in the cell. In a preferred embodiment the transgenic animals are either homo- or heterozygous knock-out or knock-in animals with respect to the genes which code for the proteins of the present invention. The animals can in principal be any animal, preferably, however, it is a mammal, selected from the group of non-human primate horse, bovine, sheep, goat, pig, dog, cat, goat, rabbit, mouse, rat, guinea pig, hamster, or gerbil. Another aspect of the present invention is a process for producing a polypeptide encoded by a polynucleotide of the present invention comprising: culturing the host cell described above and recovering the polypeptide encoded by said polynucleotide. Preferred combinations of host cells and vectors are outlined above and further combination will be readily apparent to someone of skill in the art. Depending on the intended later use of the recovered peptide a suitable cell type can be chosen. Eukaryotic cells are preferably chosen, if it is desired that the proteins produced by the cells exhibit an essentially natural pattern of glycosylation and prokaryotic cells are chosen, if for example, glycosylation or other modifications, which are normally introduced into proteins only in eukaryotic cells, are not desired or not needed.

A further aspect of the invention is a process for producing cells capable of expressing at least one of the bitter taste receptor polypeptides comprising genetically engineering cells in vitro with at least one of the vectors described above, wherein said bitter taste receptor polypeptide(s) is(are) encoded by a polynucleotide of the present invention.

Another aspect of the invention is a polypeptide having the amino acid sequence encoded by a polynucleotide of the invention or obtainable by the process mentioned above. The polypeptides of the invention include all those disclosed herein and functional fragments of these polypeptides. "Polypeptide" and "protein" are used interchangeably and mean any peptide linked chain of amino acids, regardless of length or posttranslational modification. As used herein, a functional fragment of a TAS2R is a fragment of the TAS2R that is shorter than the full-length TAS2R but that has at least 20% (e.g., at least: 20%, 30%; 40%; 50%; 60%; 70%; 80%; 90%; 95%; 98%; 99%; 99.5%; or 100% or even more) of the ability of the fall-length TAS2R to bind to a bitter substance to which the full-length TAS2R binds. Binding assays and bitter substances are described herein. Further bitter substances can be identified by the binding assays and bitter taste receptor activity assays described herein. The polypeptides embraced by the invention also include fusion proteins that contain either a fall-length TAS2R polypeptide or a functional fragment of it fused to an unrelated amino acid sequence. The unrelated sequences can be additional functional domains or signal peptides. Signal peptides are described in greater detail and exemplified below.

The polypeptides can be any of those described above but with not more than 50 (e.g., not more than: 50, 45, 40, 35, 30, 25, 20, 15, 14, 13, 12, 11, 10, nine, eight, seven, six, five, four, three, two, or one) conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. All that is required of a polypeptide having one or more conservative substitutions is that it has at least 20% (e.g., at least: 20%; 30%; 40%; 50%; 60%; 70%, 80%, 90%; 95%; 98%; 99%; 99.5%; or 100% or even more) of the ability of the wild-type, full-length TAS2R to bind to a bitter substance, preferably the ability to release intracellular calcium, when expressed in a cellular system.

The polypeptides can be purified from natural sources (e.g., blood, serum, plasma, tissues or cells such as normal tongue cells or any cell that naturally produces the relevant TAS2R polypeptides). Smaller peptides (less than 50 amino acids long) can also be conveniently synthesized by standard chemical means. In addition, both polypeptides and peptides can be produced by standard in vitro recombinant DNA techniques and in vivo transgenesis, using nucleotide sequences encoding the appropriate polypeptides or peptides. Methods ell-known to those skilled in the art can be used to construct expression vectors containing relevant coding sequences and appropriate transcriptional/translational control signals. See, for example, the techniques described in Sambrook et al., *Molecular Cloning: A Laboratory Manual* (2nd Ed.) [Cold Spring Harbor Laboratory, N.Y., 1989], and Ausubel et al., *Current Protocols in Molecular Biology* [Green Publishing Associates and Wiley Interscience, N.Y., 1989].

Polypeptides and fragments of the invention also include those described above, but modified for in vivo use by the addition, at the amino- and/or carboxyl-terminal ends, of blocking agents to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

Also of interest are peptidomimetic compounds that are designed based upon the amino acid sequences of the functional peptides or peptide fragments. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to bind to a bitter compound in a manner qualitatively identical to that of the TAS2R functional fragment from which the peptidomimetic was derived. Peptidomimetic compounds can have additional characteristics that enhance their therapeutic utility, such as increased cell permeability and prolonged biological half-life.

The peptidomimetics typically have a backbone that is partially or completely nonpeptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

The term "isolated" polypeptide or peptide fragment as used herein refers to a polypeptide or a peptide fragment which either has no naturally-occurring counterpart or has been separated or purified from components which naturally accompany it, e.g., in tissues such as tongue, pancreas, liver, spleen, ovary, testis, muscle, joint tissue, neural tissue, gastrointestinal tissue or tumor tissue, or body fluids such as blood, serum, or urine. Typically, the polypeptide or peptide fragment is considered "isolated" when it is at least 70%, by dry weight, free from the proteins and other naturally-occurring organic molecules with which it is naturally associated. Preferably, a preparation of a polypeptide (or peptide fragment thereof) of the invention is at least 80%, more preferably at least 90%, and most preferably at least 99%, by dry weight, the polypeptide (or the peptide fragment thereof), respectively, of the invention. Thus, for example, a preparation of polypeptide x is at least 80%, more preferably at least 90%, and most preferably at least 99%, by dry weight, polypeptide x. Since a polypeptide that is chemically synthesized is, by its nature, separated from the components that naturally accompany it, the synthetic polypeptide is "isolated."

An isolated polypeptide (or peptide fragment) of the invention can be obtained, for example, by extraction from a natural source (e.g., from tissues or bodily fluids); by expression of a recombinant nucleic acid encoding the polypeptide; or by chemical synthesis. A polypeptide that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

A further aspect of the invention is an antibody, which specifically binds to the polypeptide encoded by a polynucleotide of the invention or obtainable by the process mentioned above. The term "antibody" comprises monoclonal and polyclonal antibodies and binding fragments thereof, in particular Fc-fragments as well as so called "single-chain-antibodies" (Bird R. E. et al (1988) Science 242:423-6), chimeric, humanized, in particular CDR-grafted antibodies, and dia or tetrabodies (Holliger P. et al (1993) Proc. Natl. Acad. Sci. U.S.A. 90:6444-8). Also comprised are immunoglobulin like proteins that are selected through techniques including, for example, phage display to specifically bind to the polypeptides of the present invention. Preferred antibodies bind to the extracellular domain of bitter receptors and in particular to those domains responsible for binding to bitter tastants.

In yet another embodiment there is provided a molecule, or collections of molecules containing a molecule, that act to antagonise aforementioned receptors in particular the bitter taste response, and methods for screening for such molecules.

Therefore, a further aspect of the invention is a nucleic acid molecule which specifically hybridizes to a polynucleotide of the present invention. In particular this nucleic acid molecule is an inhibiting RNA. Preferred inhibiting RNAs are antisense constructs hybridizing to a polynucleotide of the present invention, RNAi, siRNA or a ribozyme. The design of such inhibiting RNAs would be readily apparent to someone of skill in the art.

Another type of antagonist/inhibitor against the polypeptides of the present invention is an antibody, which is preferably directed against the extracellular domain of the respective bitter taste receptor and even more preferably binds to the site(s) of the receptor that interact(s) with the bitter substance(s) essentially without triggering the release of intracellular calcium. Further antagonists to the bitter taste response of a receptor are fragments of the receptor which have the capability to bind to the bitter substances as defined above. Such fragments can bind to the bitter substance and, thus, competitively antagonize the activity of the respective TAS2R. If such antagonists are, for example, employed within foodstuff to suppress the bitter taste of a specific bitter substance they might be exposed to a proteolytic environment and in this case the modifications of the polypeptides outlined above could be used to stabilize the competitive bitter receptor antagonist. However, various additional modifications, which stabilize such fragments will be readily apparent to the skilled person.

Antagonists and agonists of the bitter taste receptors described herein are of great importance for specific stimulation of a given bitter taste receptor or to antagonize it. The bitter taste response of the receptor is elicited by the specific binding of the respective bitter substance. Therefore, the present invention is also directed at a process for isolating a compound that binds to a polypeptide encoded by a polynucleotide selected from the group consisting of (a) polynucleotides encoding at least the mature form of the polypeptide having the deduced amino acid sequence as shown in SEQ ID NOs 1, 3, 5, 7, 9, 11, 13, 15, 17, 19, 21, 23, 25, 27, 29, 31, 33, 35, 37, 39, 41, 43, 45, 47 and 49;

(b) polynucleotides having the coding sequence, as shown in SEQ ID NOs: 2, 4, 6, 8, 10, 12, 14, 16, 18, 20, 22, 24, 26, 28, 30, 32, 34, 36, 38, 40, 42, 44, 46, 48 and 50 encoding at least the mature form of the polypeptide;

(c) polynucleotides encoding a fragment or derivative of a polypeptide encoded by a polynucleotide of any one of (a) to (b), wherein in said derivative one or more amino acid residues are conservatively substituted compared to said polypeptide, and said fragment or derivative has bitter substance binding activity;

(d) polynucleotides which are at least 50% identical to a polynucleotide as defined in any one of (a) to (c) and which code for a polypeptide having bitter substance binding activity; and (e) polynucleotides the complementary strand of which hybridizes, preferably under stringent conditions to a polynucleotide as defined in any one of (a) to (d) and which code for a polypeptide having bitter substance binding activity;

comprising:

(1) contacting said polypeptide or a host cell genetically engineered with said polynucleotide or with a vector containing said polynucleotide with a compound;

(2) detecting the presence of the compound which binds to said polypeptide; and (3) determining whether the compound binds said polypeptide.

A polynucleotide employed in this process is in preferred embodiments of the invention at least 50% (or 55%, 65%, 75%, 85°/a, 95%, or 98%) identical to (a) a nucleic acid molecule that encodes the polypeptide of SEQ ID NOs: 1, 3, 5, 7, 9, 11, 13, 15, 17, 19, 21, 23, 25, 27, 29, 31, 33, 35, 37, 39, 41, 43, 45, 47 or 49; (b) the nucleotide sequence of SEQ ID NOs: 2, 4, 6, 8, 10, 12, 14, 16, 18, 20, 22, 24, 26, 28, 30, 32, 34, 36, 38, 40, 42, 44, 46, 48 or 50; and has a length of at least 30 (e.g., at least 30, 40, 50, 60, 80, 100, 125, 150, 175, 200, 250, 300, 400, 500, 600, 700, 800, 850, 900, 950, 1000, or 1010) of the nucleotides of SEQ ID NOs: 2, 4, 6, 8, 10, 12, 14, 16, 18, 20, 22, 24, 26, 28, 30, 32, 34, 36, 38, 40, 42, 44, 46, or 50.

Furthermore for all of the above described hTAS2R5, which can be employed in a process for isolating binding compounds, with the exception of hTAS2R40, single nucleotide polymorphisms are known. 79 of these are listed in Table I below. 61 of those result in an amino acid change. Polynucleotides or polypeptides that differ from the respectively in SEQ ID 1-50 indicated sequences by the nucleotide and amino acid change as indicted in Table I can similarly be employed for the process of the present invention.

TABLE I

| Gen + Acession No. | Name of SNP | Substitution | | Position | | Allelic frequency |
| --- | --- | --- | --- | --- | --- | --- |
| | | Base | Amino acid | Base pair | Amino acid | |
| hTAS2R1 | rs2234231 | C/T | P/L | 128 | 43 | unknown |
| NM019599 | rs41469 | G/A | R/H | 332 | 111 | A 0.46/G 0.54 |
| | rs223432 | G/A | C/Y | 422 | 141 | unknown |
| | rs2234233 | C/T | R/W | 616 | 206 | C 0.87/T 0.13 |
| | rs2234234 | C/T | S/S | 675 | 225 | unknown |
| | rs2234235 | T/C | L/L | 850 | 284 | unknown |

TABLE I-continued

| Gen + Acession No. | Name of SNP | Substitution Base | Amino acid | Position Base pair | Amino acid | Allelic frequency |
|---|---|---|---|---|---|---|
| hTAS2R3 NM016943 | rs227009 | C/T | G/G | 807 | 369 | unknown |
| hTAS2R4 NM016944 | ss3181498 | G/A | R/Q | 8 | 3 | unknown |
|  | rs2233996 | G/C | R/R | 9 | 3 | unknown |
|  | rs2233997 | A/C | Y/C | 17 | 6 | unknown |
|  | rs2233998 | T/C | F/S | 20 | 7 | unknown |
|  | rs2233999 | T/A | F/L | 186 | 62 | unknown |
|  | rs2234000 | C/T | T/M | 221 | 74 | C 0.94/T 0.56 |
|  | rs2234001 | G/C | V/L | 286 | 96 | C 0.78/G 0.22 |
|  | rs2234002 | G/A | S/N | 512 | 171 | A 0.78/G 0.22 |
|  | rs2234003 | A/G | I/V | 571 | 191 | unknown |
| hTAS2R5 | rs2234013 | G/A | G/S | 58 | 20 | unknown |
|  | rs2227264 | G/T | S/I | 77 | 26 | unknown |
|  | rs2234014 | C/T | P/L | 338 | 113 | unknown |
|  | rs2234015 | G/A | R/Q | 638 | 213 | unknown |
|  | rs2234016 | G/T | R/L | 294 | 881 | unknown |
| hTAS2R7 NM023919 | rs3759251 | A/T | T/S | 787 | 263 | A 0.97/T 0.03 |
|  | rs3759252 | C/A | I/I | 828 | 276 | unknown |
|  | rs619381 | G/A | M/I | 912 | 304 | unknown |
| hTAS2R8 NM023918 | ss2391467 | G/A | L/L | 549 | 183 | unknown |
|  | rs2537817 | A/G | M/V | 922 | 308 | unknown |
| hTAS2R9 NM23917 | rs3741845 | T/C | V/A | 560 | 187 | C 073/T 027 |
|  | rs3944035 | C/T | L/F | 910 | 304 | unknown |
|  | rs2159903 | C/T | P/L | 926 | 309 | unknown |
| hTAS2R10 NM23921 | rs597468 | C/T | T/M | 467 | 156 | unknown |
| hTAS2R13 NM23920 | ss1478988 | A/G | N/S | 776 | 259 | C 0.73/T 0.27 |
| hTAS2R14 NM23922 | rs3741843 | G/A | R/R | 375 | 125 | A 0.97/G 0.03 |
| hTAS2R16 NM016945 | rs2233988 | C/T | T/T | 300 | 100 | unknown |
|  | rs2692396 | G/C | V/V | 303 | 101 | unknown |
|  | rs2233989 | T/C | L/L | 460 | 154 | unknown |
|  | rs846664 | T/G | N/K | 516 | 172 | A 0.71/C 0.29 |
|  | rs860170 | G/A | R/H | 665 | 222 | A 0.55/G.0.45 |
| hTAS2R38 AF494321 | PTC Paper | G/A | V/I | 886 | 296 | G 0.38/A 0.62 |
|  | rs1726866 | T/C | V/A | 785 | 262 | G 0.38/T 0.62 |
|  | rs713598 | C/T | A/P | 49 | 145 | C 0.36/G 0.64 |
|  | hTAS2R38 SNP1 | A/T | N/I | 557 | 186 | C 0.60/G 0.40 |
| hTAS2R39 AF494230 | hTAS2R39 SNP1 | A/AA | frameshift | 967 | 323 | unknown |
| hTAS2R41 AF494232 | rs1404635 | A/G | T/T | 189 | 64 | unknown |
|  | hTAS2R41 SNP1 | T/C | L/P | 380 | 127 | unknown |
|  | hTAS2R41 SNP2 | A/G | S/S | 885 | 295 | unknown |
| hTAS2R42 AX097739 | rs1650017 | G/C | A/P | 931 | 311 | unknown |
|  | rs1669411 | T/C | N/N | 930 | 310 | unknown |
|  | rs1669412 | G/A | R/Q | 875 | 292 | unknown |
|  | rs1451772 | A/G | Y/C | 794 | 265 | unknown |
|  | rs1669413 | G/T | G/W | 763 | 255 | unknown |
|  | rs1650019 | A/G | L/L | 561 | 187 | unknown |
| hTAS2R43 AF494237 | rs3759246 | G/C | R/T | 893 | 298 | unknown |
|  | hTAS2R43 SNP1 | C/G | S/W | 104 | 35 | unknown |
|  | hTAS2R43 SNP2 | G/A | R/H | 635 | 212 | unknown |
|  | hTAS2R43 SNP3 | G/C | T/T | 663 | 221 | unknown |
| hTAS2R44 AF494228 | rs3759247 | G/A | W/stop | 900 | 300 | unknown |
|  | rs3759246 | G/C | R/T | 893 | 298 | unknown |
|  | hTAS2R44 SNP1 | A/T | M/L | 162 | 484 | unknown |
|  | hTAS2R44 SNP2 | T/A | F/Y | 869 | 290 | unknown |
|  | hTAS2R44 SNP3 | G/A | V/M | 899 | 297 | unknown |
| hTAS2R45 AF494226 | rs3759247 | A/G | G/stop | 900 | 300 | unknown |
|  | rs3759246 | G/C | R/T | 893 | 298 | unknown |
|  | rs3759245 | C/T | R/C | 712 | 238 | unknown |
|  | rs3759244 | T/C | F/L | 703 | 235 | unknown |
| hTAS2R46 AF494227 | rs2708381 | G/A | W/stop | 749 | 250 | unknown |
|  | rs2708380 | T/A | L/M | 682 | 228 | unknown |
|  | rs2598002 | T/G | F/V | 106 | 36 | unknown |
|  | hTAS2R46 SNP1 | A/T | Q/H | 888 | 296 | unknown |
|  | hTAS2R46 SNP2 | A/G | M/V | 889 | 297 | unknown |
|  | hTAS2R46 SNP3 | T/C | F/F | 108 | 36 | unknown |
| hTAS2R47 AF494233 | rs2597924 | G/A | R/H | 920 | 307 | unknown |
|  | rs1669405 | T/G | L/W | 842 | 281 | unknown |
|  | rs2599404 | T/G | F/L | 756 | 252 | unknown |
|  | rs2600355 | T/G | V/V | 54 | 18 | unknown |
| hTAS2R48 AF494234 | rs1868769 | T/C | L/L | 418 | 140 | unknown |

TABLE I-continued

| Gen + Acession No. | Name of SNP | Substitution | | Position | | |
|---|---|---|---|---|---|---|
| | | Base | Amino acid | Base pair | Amino acid | Allelic frequency |
| hTAS2R49 AF494236 | hTAS2R49 SNP1 | A/G | K/R | 164 | 55 | unknown |
| hTAS2R50 | rs1376521 | A/G | Y/C | 608 | 203 | G 0.66/A 0.34 |
| AF494235 | hTAS2R50 SNP1 | A/G | P/P | 777 | 259 | unknown |

A polypeptide that exhibits bitter substance binding activity is a polypeptide that has at least 20% (e.g., at least: 20%; 30%; 40%; 50%; 60%; 70%; 80%; 90%; 95%; 98%; 99%; 99.5%; or 100% or even more) of the ability of the respective full-length TAS2R to bind to a given bitter substance. Binding assays and bitter substances are described herein.

The term "contacting" in the context of the present invention means any interaction between the compound with the polypeptide of the invention, whereby any of the at least two components can be independently of each other in a liquid phase, for example in solution, or in suspension or can be bound to a solid phase, for example, in the form of an essentially planar surface or in the form of particles, pearls or the like. In a preferred embodiment a multitude of different compounds are immobilized on a solid surface like, for example, on a compound library chip and the protein of the present invention is subsequently contacted with such a chip. In another preferred embodiment the cells genetically engineered with the polynucleotide of the invention or with a vector containing such a polynucleotide express the bitter taste receptor at the cell surface and are contacted separately in small containers, e.g., microtitre plates, with various compounds.

Detecting the presence and the binding of the compound to the polypeptide can be carried out, for example, by measuring a marker that can be attached either to the protein or to the compound Suitable markers are known in the art and comprise, for example, fluorescence, enzymatic or radioactive markers. The binding of the two components can, however, also be measured by the change of an electrochemical parameter of the binding compound or of the protein, e.g. a change of the redox properties of either the protein or the binding compound, upon binding. Suitable methods of detecting such changes comprise, for example, potentiometric methods. Further methods for detecting and/or measuring the binding of the two components to each other are known in the art and can without limitation also be used to measure the binding of the compound to the polypeptide. The effect of the binding of the compound on the activity of the polypeptide can also be measured by assessing changes in the cells that express the polypeptides, for example, by assaying the intracellular release of calcium upon binding of the compound.

As a further step after measuring the binding of a compound and after having measured the binding strength of at least two different compounds at least one compound can be selected, for example, on grounds of a higher binding strength or on grounds of the detected intracellular release of calcium.

The thus selected compound is than in a preferred embodiment modified in a further step. Modification can be effected by a variety of methods known in the art, which include without limitation the introduction of one or more, preferably two three or four novel side chains or residues or the exchange of one or more functional groups like, for example, introduction or exchange of halogens, in particular F, Cl or Br; the introduction or exchange of lower alkyl residues, preferably having one to five carbon atoms like, for example, methyl, ethyl, n-propyl, isopropyl, n-butyl, isobutyl, tert-butyl, n-pentyl or iso-pentyl residues; lower alkenyl residues, preferably having two, three, four or five carbon atoms; lower alkinyl residues, preferably having two, three, four or five carbon atoms, which can in a preferred embodiment be further substituted with F, Cl, Br, $NH_2$, $NO_2$, OH, SH, NH, CN, aryl, heteroaryl, COH or COOH group; or the introduction of, for example, one or more residue(s) selected from the group consisting of $NH_2$, $NO_2$, OH, SH, NH, CN, aryl, alkylaryl, heteroaryl, alkylheteroaryl, COH or COOH group.

The thus modified binding substances are than individually tested with the method of the present invention, i.e. they are contacted with the polypeptide as such or with the polypeptide expressed in a cell, and subsequently binding of the modified compounds is measured. In this step both the binding per se can be measured and/or the effect of the function of the protein like, e.g. the intracellular calcium release. If needed the steps of selecting the compound, modifying the compound, contacting the compound with a polypeptide of the invention and measuring the binding of the modified compound to the polypeptide can be repeated a third or any given number of times as required. The above described method is also termed "directed evolution" of the compound since it involves a multitude of steps including modification and selection, whereby binding compounds are selected in an "evolutionary" process optimizing their capabilities with respect to a particular property, e.g. its binding activity, its ability to activate, inhibit or modulate the activity, in particular inhibit the intracellular release of calcium mediated by the polypeptides of the present invention.

Of particular interest are compounds that antagonize the bitter taste receptor activity of the TAS2Rs disclosed and described herein. The specification thereby enables the skilled person to design intelligent compound libraries to screen for antagonists to the bitter response of these receptors, which in turn enables the development of compounds and compositions to suppress or eliminate bitter tasting components of foods, in particular animal foods, nutrients and dietary supplements and pharmaceutical or homeopathic preparations containing such phyto-chemicals. Similarly, the invention also enables the skilled person to screen for additional bitter ligands, or even to screen for compounds that enhance a bitter response, such as might be useful in the food industry. Therefore, another aspect of the invention is a process for isolating an antagonist of the bitter taste receptor activity of the polypeptide encoded by a polynucleotide selected from the group consisting of:

(a) polynucleotides encoding at least the mature form of the polypeptide having the deduced amino acid sequence as shown in SEQ ID NONOs: 1, 3, 5, 7, 9, 11, 13, 15, 17, 19, 21, 23, 25, 27, 29, 31, 33, 35, 37, 39, 41, 43, 45, 47 and 49;

(b) polynucleotides having the coding, sequence, as shown in SEQ ID NOs: 2, 4, 6, 8, 10, 12, 14, 16, 18, 20, 22, 24, 26, 28, 30, 32, 34, 36, 38, 40, 42, 44, 46, 48 and 50 encoding at least the mature form of the polypeptide;
(c) polynucleotides encoding a fragment or derivative of a polypeptide encoded by a polynucleotide of any one of (a) to (b), wherein in said derivative one or more amino acid residues are conservatively substituted compared to said polypeptide, and said fragment or derivative has bitter taste receptor activity;
(d) polynucleotides which are at least 50% identical to a polynucleotide as defined in any one of (a) to (c) and which code for a polypeptide having bitter taste receptor activity; and
(e) polynucleotides the complementary strand of which hybridizes, preferably under stringent conditions to a polynucleotide as defined in any one of (a) to (d) and which code for a polypeptide having bitter taste receptor activity;
comprising:
(1) contacting said polypeptide or a host cell genetically engineered with said polynucleotide or with a vector containing said polynucleotide with a potential antagonist;
(2) determining whether the potential antagonists antagonizes the bitter taste receptor activity of said polypeptide.

The polynucleotide employed in this process encodes a polypeptide that still exhibits essentially the same activity as the respective mature bitter taste receptor, i.e. has "bitter taste receptor activity". Preferably the polypeptide has at least 20% (e.g., at least: 20%; 30%; 40%; 50%; 60%; 70%; 80%; 90%; 95%; 98%; 99%; 99.5%; or 100% or even more) of the activity of the respective full-length TAS2R. One preferred way of measuring TAS2R activity is the ability to release intracellular calcium in a heterologous cell expression system like, for example, (HEK293/15) that stably expresses the alpha-subunit of promiscuous G-proteins, e.g. the mouse $G_{15}$ subunit or chimeric, in response to bitter tastants, which is dependent on the expression of polypeptides encoded by the polynucleotides of the present invention. The amount of intracellular calcium released can be monitored by, for example, the in vitro FLIPR assay described herein but also by the measurement of one of a variety of other parameters including, for example, $IP_3$ or cAMP. Additional ways of measuring G-protein coupled receptor activity are known in the art and comprise without limitation electrophysiological methods, transcription assays, which measure, e.g. activation or repression of reporter genes which are coupled to regulatory sequences regulated via the respective G-protein coupled signaling pathway, such reporter proteins comprise, e.g., CAT or LUC; assays measuring internalization of the receptor; or assays in frog melanophore systems, in which pigment movement in melanophores is used as a read out for the activity of adenylate cyclase or phospholipase C (PLC), which in turn are coupled via G-proteins to exogenously expressed receptors (see, for example, McClintock T. S. et al. (1993) Anal. Biochem. 209: 298-305; McClintock T. S, and Lerner M. R. (1997) Brain Res. Brain, Res. Protoc. 2: 59-68, Potenza M N (1992) Pigment Cell Res. 5: 372-328, and Potenza M. N. (1992) Anal. Biochem. 206: 315-322)

As described above with the exception of hTAS2R40, single nucleotide polymorphisms are known for all of the above hTAS2Rs, which can be employed in a process for isolating an antagonist of the bitter taste receptor activity. Polynucleotides or polypeptides that differ from the respectively in SEQ ID 1-50 indicated sequences by the nucleotide and amino acid change as indicted in Table I can similarly be employed for the process of the present invention.

The term "contacting" has the meaning as outlined above. A potential antagonist is a substance which lowers the respective bitter taste receptor activity determined in the absence of the antagonist by at least 10% (e.g., at least: 1%, 15% 20%; 30%; 40%; 50%; 60%; 70%; 80%; 90%; 95%; 98%; 99%; 99.5%; or 100%) once contacted with the bitter taste receptor.

In a preferred embodiment the process further comprises the contacting of the polypeptide with an agonist of the respective bitter taste receptor activity. The contacting of the bitter taste receptor with the agonist can be carried out prior, concomitantly or after contacting the polypeptide with the potential antagonist.

It has been demonstrated by the inventors that the bitter receptors hTAS2R10, hTAS2R14, hTAS2R16, hTAS2R38, hTAS2R43, hTAS2R44, hTAS2R45, hTAS2R46 and hTAS2R48 respond with specificity to (a) defined classe(s) of ligand(s) that include a class of useful phyto-chemicals in a functional expression assay. Therefore, in an even more preferred embodiment the polypeptides and agonist employed together in above process are selected from the group consisting of
(a) the polypeptide encoded by the polynucleotide outlined above as determined by SEQ ID NO: 1 and SEQ ID NO: 2 and the agonist selected from the group consisting of acetylthiourea, N,N-dimethylthioformamide, N,N'-diphenylthiourea, N-ethylthiourea, 2-imidazolidinethione, 4(6)-methyl-2-thiouracil, N-methylthiourea, phenylthio-carbamid, 6-phenyl-2-thiouracil, 6-propyl-2-thiouracil, tetramethylthiourea, thioacetamide, thio-acetanilide, 2-thiobarbituric acid, and 2-thiouracil and functional derivatives thereof;
(b) the polypeptide encoded by the polynucleotide of claim 1 or 2 as determined by SEQ ID NO: 9 and SEQ ID NO: 10 and the agonist selected from the group consisting of saccharin and functional derivatives thereof;
(c) the polypeptide encoded by the polynucleotide of claim 1 or 2 as determined by SEQ ID NO: 11 and SEQ ID NO: 12 and the agonist selected from the group consisting of saccharin and acesulfame K and functional derivatives thereof;
(d) the polypeptide encoded by the polynucleotide of claim 1 or 2 as determined by SEQ ID NO 13 and SEQ ID NO 14 and the agonist selected from the group consisting of absinthine and functional derivatives thereof;
(e) the polypeptide encoded by the polynucleotide of claim 1 or 2 as determined by SEQ ID NO 15 and SEQ ID NO 16 and the agonist selected from the group consisting of absinthine and functional derivatives thereof;
(f) the polypeptide encoded by the polynucleotide of claim 1 or 2 as determined by SEQ ID NO 19 and SEQ ID NO 20 and the agonist selected from the group consisting of absinthine and functional derivatives thereof;
(g) the polypeptide encoded by the polynucleotide of claim 1 or 2 as determined by SEQ ID NO 37 and SEQ ID NO 38 and the agonist selected from the group consisting of strychnine, brucine, denatonium benzoate, and absinthine and functional derivatives thereof;
(h) the polypeptide encoded by the polynucleotide of claim 1 or 2 as determined by SEQ ID NO: 41 and SEQ ID NO: 42 and the agonist selected from the group consisting of tyrosine, preferably L-tyrosine, and other bitter tasting amino acids including, e.g., leucine, histidine phenylalanine and tryptophan, and functional derivatives thereof; and
(i) the polypeptide encoded by the polynucleotide of claim 1 or 2 as determined by SEQ ID NO: 43 and SEQ ID NO: 44 and the agonist selected from the group consisting of naphtyl-β-D-glucoside, phenyl-β-D-glucoside, salicin, helicin, arbutin, 2-nitrophenyl-β-D-glucoside, 4-nitrophenyl-β-D-glucoside, methyl-β-D-glucoside, esculin, 4-nitrophenyl- β-D-thioglucoside, 4-nitrophenyl-β-D-mannoside, and amygdalin and functional derivatives thereof.

The term "functional derivatives thereof" refers to substances, which are derived from the respectively indicated bitter substance by chemical modification and which elicit at least 20% (e.g., at least: 20%; 30%; 40%; 50%; 60%; 70%; 80%; 90%; 95%; 98%; 99%; 99.5%; or 100% or even more) of the bitter taste receptor activity, if compared to the respective unmodified bitter substance. Chemical modification includes without limitation the introduction of one or more, preferably two, three or four novel side chains or residues or the exchange of one or more functional groups like, for example, introduction or exchange of H; linear or branched alkyl, in particular lower alkyl ($C_1$, $C_2$, $C_3$, $C_4$, and $C_5$, e.g. methyl, ethyl, n-propyl, isopropyl, n-butyl, isobutyl, tert-butyl, n-pentyl or iso-pentyl); substituted linear or branched alkyl, in particular lower substituted alkyl; linear or branched alkenyl, in particular lower alkenyl ($C_2$, $C_3$, $C_4$ and $C_5$, e.g. ethenyl, 1-propenyl, 2-propenyl, iso-propenyl, 1-butenyl, 2-butenyl, 3-butenyl; substituted linear or branched alkenyl, in particular lower substituted alkenyl; linear or branched alkinyl, in particular lower alkinyl ($C_2$, $C_3$, $C_4$ and $C_5$), substituted linear or branched alkinyl, in particular lower substituted alkinyl; linear or branched alkanol, in particular lower alkanol ($C_1$, $C_2$, $C_3$, $C_4$, and $C_5$); linear or branched alkanal, in particular lower alkanal ($C_1$, $C_2$, $C_3$, $C_4$, and $C_5$, e.g. COH, $CH_2COH$, $CH_2CH_2COH$; aryl, in particular phenyl; substituted aryl, in particular substituted aryl; heteroaryl; substituted heteroaryl; alkylaryl, in particular benzyl; substituted alkylaryl; in particular substituted benzyl; alkylheteroaryl; substituted alkylheteroaryl; aminoalkyl, $C_1$, $C_2$, $C_3$, $C_4$ and $C_5$, e.g. —$NHCH_3$, —$NHCH_2CH_3$, —$N(CH_3)_2$; substituted aminoalkyl; aminoketone, in particular —$NHCOCH_3$; substituted aminoketone; aminoaryl, in particular —NH-Ph; substituted aminoaryl, in particular substituted —NH-Ph; CN; $NH_2$; Halogen, in particular F, Cl, and Br; $NO_2$, OH; SH; NH; CN; or COOH group. If the residues mentioned above are substituted they are preferably mono, di, or tri substituted with a substituent selected from the group of halogen, in particular F, Cl, and Br, $NH_2$, $NO_2$, OH, SH, NH, CN, aryl, alkylaryl, heteroaryl, alkylheteroaryl, COH or COOH.

In particular the hTAS2R16 receptor has been shown to respond specifically to a narrow class of interesting phytochemicals selected from the group consisting of bitter beta-glucopyranosides and mannopyranosides.

The beta-glucopyranosides and beta-mannosepyranosides are a group of bitter compounds consisting of a hydrophobic residue attached to glucose and mannose, respectively, by a beta-glycosidic bond.

Preferred compounds that bind to the hTAS2R16 taste receptor are chosen from beta glucopyranosides and beta-mannopyranosides defined by the formula:

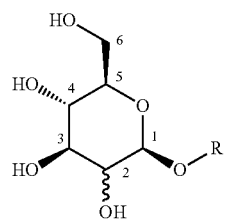

These compounds were studied in vitro (see Table I and IV below) and also by human panelists (see Table I below) as is described in greater detail below.

From these studies certain inferences can be drawn regarding the affinity of the compounds towards activation of the hTAS2R16 receptor. Thus, for the promotion of activation the steric position at C2 can be either alpha or beta and the beta-configuration of the glycosidic bond and the alpha steric position of the hydroxyl group at C4 of the pyranose ring are preferred. Whereas R can be hydrogen, it is preferred that R is a substituent selected from $C_1$-$C_8$ alkyl which may be branched, linear or cyclic as appropriate; lower alkenyl residues, preferably having two, three, four or five carbon atoms; lower alkinyl residues, preferably having two, three, four or five carbon atoms, which can in a preferred embodiment be further substituted with F, Cl, Br, $NH_2$, $NO_2$, OH, SH, NH, CN, aryl, heteroaryl, COH or COOH group; heteroaryl, e.g. benzofuran and cumarin; aryl, e.g. phenyl, naphtyl; or the same of other sugar residue, e.g. glucopyranoside, which itself can carry a substituent R with the meaning as outlined above. Bulkier groups at C1 may increase the activation of the receptor. The aryl or heteroaryl may be further substituted with one or more substituents. Preferred substituents of the aryl or heteroaryl group are F, Br, $C_1$, $NO_2$, lower alkyl with one, two, three, four, five, six, seven or eight carbon atoms and $CH_2OH$. The phenyl group is preferably mono, di, or trisubstituted in ortho, para and/or meta position(s). The substituent at C6 is shown as an hydroxyl group above. However, the compounds activity as agonists are little effected by further or alternative substitution at this position, and there is design freedom at this part of the compound. Furthermore, without intending to be bound by theory, it is thought that the substituent "R" is not responsible for bitterness in these compounds. Rather, bitterness is thought to derive from a hydrogen acceptor and donor site provided by two hydroxyl groups on the ring. In another embodiment the O-glycosidic bond of the compounds outlined above can be a S-glycosidic bond, as exemplified by the bitter substance 4-nitrophenyl-β-D-thioglucoside.

Most preferred compounds are selected from the group consisting of naphtyl-β-D-glucoside, phenyl-β-D-glucoside, salicin, helicin, arbutin, 2-nitrophenyl-β-D-glucoside, 4-nitrophenyl-β-D-glucoside, methyl-β-D-glucoside, esculin, 4-nitrophenyl-β-D-thioglucoside, 4-nitrophenyl-β-D-mannoside, and amygdalin.

The beta-glucopyranosides are phytonutrients that represent an important class of compounds found in plant-derived foods that may be useful as dietary supplements, or in functional foods or medicaments for the prevention of disease states. However, due to their bitter after-taste they are aversive to consumers and so they are routinely removed from foods during production and processing as is further described in Drewnowski, A. & Gomez-Cameros, C. Bitter taste, phytonutrients, and the consumer: a review. *Am. J. Clin. Nutr.* 72, 1424-1435 (2000). Removal is laborious and therefore expensive. The alternative is to mask the off-flavor using encapsulation technologies or organoleptic compounds as masking agents. However, encapsulation technology may not be appropriate in pharmaceutics as this may affect the absorption characteristics of the active compound, whereas the use of masking agents may impart their own characteristic flavor which may unbalance the flavor of food or beverages.

Without wishing to be bound by any particular theory as to their mechanism of action, applicant believes that the bitter receptors activate a G-protein and thereby initiate the aforementioned cellular activation cascade as a result of conformational changes in the receptor after binding by a ligand. Potential antagonists of the bitter response will contain functionality (i.e., will compete for binding at the receptor, and/or act at another binding site through an allosteric mechanism, and/or stabilize the receptor in the inactive conformation, and/or bind reversibly or irreversibly, and/or weaken receptor G protein interaction, and/or interfere with G protein activation).

Similarly, in another embodiment of the invention, it has been found that the so-called hTAS2R10 receptor is activated by strychnine, and strychnine analogues such as brucine as well as by denatonium benzoate, absinthine and other alkaloids with (a) ring system(s). Strychnine and its analogues are also useful phytochemicals that find use in medicines and homeopathic treatments.

In another embodiment of the invention, it has been found that the so-called hTAS2R14 receptor is activated by tyrosine, in particular L-tyrosine, and other bitter tasting amino acids including leucine, histidine, phenylalanine and tryptophan.

In another embodiment of the invention, it has been found that the so-called hTAS2R38 receptor is activated by acetylthiourea, N,N-dimethylthioformamide, N,N'-diphenylthiourea, N-ethylthiourea, 2-imidazolidinethione, 4(6)-methyl-2-thiouracil, N-methylthiourea, phenylthio-carbamid, 6-phenyl-2-thiouracil, 6-propyl-2-thiouracil, tetramethylthiourea, thioacetamide, thioacetanilide, 2-thiobarbituric acid, and 2-thiouracil.

From these studies certain inferences can be drawn regarding the affinity of the compounds, which activate the hTAS2R38 receptor. Thus, for the promotion of activation derivatives of 2-thiouracil according to following formula are preferred compounds.

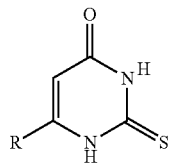

Whereas R in this formula can be hydrogen, it is preferred that R is a substituent selected from $C_1$-$C_{10}$ alkyl, which may be branched, linear or cyclic as appropriate, particularly preferred alkyls are methyl, ethyl, n-propyl, isopropyl, n-butyl, isobutyl, tert-butyl, n-pentyl or iso-pentyl residues; lower alkenyl residues, preferably having two, three, four or five carbon atoms; lower alkynyl residues, preferably having two, three, four or five carbon atoms, which can in a preferred embodiment be further substituted with F, Cl, Br, $NH_2$, $NO_2$, OH, SH, NH, CN, aryl, heteroaryl, COH or COOH group; heteroaryl, e.g. benzofuran and cumarin; aryl, e.g. phenyl, naphtyl; F, Cl, Br, $NH_2$, $NO_2$, OH, SH, NH, CN, aryl, alkylaryl, heteroaryl, alkylheteroaryl, COH or COOH group. In a further embodiment the carbon atom at the 4 position can substituted with —O—$R_1$ in which $R_1$ can have the same meaning as outlined above for R.

Another general structure of compounds having affinity for hTAS2R38 and which are thus suitable for activation of hTAS2R38 is depicted by the following formula:

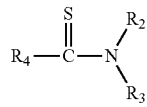

In this formula $R_2$, $R_3$, and $R_4$ can each independently of each other have the meaning H; alkyl, in particular lower alkyl ($C_1$-$C_5$, e.g. methyl, ethyl, n-propyl, isopropyl, n-butyl, isobutyl, tert-butyl, n-pentyl or iso-pentyl); substituted alkyl; alkenyl, in particular lower alkenyl (C2-$C_5$); substituted alkenyl; alkinyl, in particular lower alkinyl ($C_2$-$C_5$); substituted alkinyl: alkanal, in particulars lower alkanal (e.g. —$COCH_3$, —$COCH_2CH_3$, —$COCH_2CH_2CH_3$); aryl, in particular phenyl; substituted aryl; heteroaryl; substituted heteroaryl; alkylaryl, in particular benzyl; substituted alkylaryl; alkylheteroaryl; substituted alkylheteroaryl aminoalkyl, in particular —$NHCH_3$, —$NHCH_2CH_3$, —$N(CH_3)_2$; substituted aminoalkyl; aminoketone, in particular —$NHCOCH_3$; substituted aminoketone; aminoaryl, in particular —NH-Ph; substituted aminoaryl; CN; $NH_2$; Halogen, in particular F, Cl, and Br; $NO_2$. In a preferred embodiment $R_2$ or $R_3$ and $R_4$ can form a ring, preferably a four, five, six, seven or eight membered hetero cycle, which in a preferred embodiment is an aromatic hetero cycle. The residue of $R_2$ or $R_3$, which is not involved in the formation of the ring structure can have any of the meanings as outlined above. In a further preferred embodiment at least one of $R_2$ or $R_3$ has the meaning alkanal, preferably lower alkanal as outlined above. In case that only one of $R_2$ or $R_3$ has the meaning alkanal, than the other substituent preferably has the meaning H.

In a preferred embodiment $R_2$ is selected from the group consisting of H, $CH_3$ and Ph, $R_3$ is selected from the group of H, $CH_3$ and Ph and $R_4$ is selected from the group consisting of H, $CH_3$, NH-Ph, —$NHCH_2CH_3$, —$NHCH_2CH_3$, —$NHCH_3$, and —$N(CH_3)_2$.

In another embodiment of the invention, it has been found that the so-called hTAS2R43 receptor is activated by saccharin, derivatives thereof and other sulfoneimids.

In another embodiment of the invention, it has been found that the so-called hTAS2R44 receptor is activated by saccharin and acesulfame K, derivatives thereof and other sulfoneimids.

In another embodiment of the invention, it has been found that the so-called hTAS2R45, hTAS2R46 and hTAS2R48 receptor is activated by absinthine derivatives thereof and other sulfoneimids.

The skilled person will appreciate that having regard to the structure-function information provided by the present invention, it is possible to compile libraries of molecules to find inhibitors of the bitter response of the disclosed hTAS2R in particular of the hTAS2R10, 14, 16, 38, 43, 44, 45, 46, and 48, which are triggered by the above outlined specific bitter substance(s). Such inhibitors, and libraries comprising same, form other aspects of the present invention. A still further aspect of the invention relates to the use of such inhibitors in food or pharmaceutical compositions containing bitter tastants such as referred to herein above, for the elimination or suppression of bitter taste perception.

In practicing the various aspects and embodiments of the present invention in relation to cloning receptors, elucidating ligand-receptor pairs, and finding modulators of the bitter response of receptors, recourse is made to conventional techniques in molecular biology, microbiology and recombinant technology. Accordingly, the skilled person is fully apprised of such techniques and as such they are hereafter treated only summarily in order to more fully describe the context of the present invention.

In order to express cDNAs encoding the receptors, one typically subclones receptor cDNA into an expression vector that contains a strong promoter to direct transcription, a transcription/translation terminator, and a ribosome-binding site for translational initiation. Suitable bacterial promoters are well known in the art, e.g., *E. coli, Bacillus* sp., and *Salmonella*, and kits for such expression systems are commercially available. Similarly eukaryotic expression systems for mammalian cells, yeast, and insect cells are well known in the art and are also commercially available. The eukaryotic expression vector may be, for example an adenoviral vector, an adeno-associated vector, or a retroviral vector.

In addition to the promoter, the expression vector typically contains a transcription unit or expression cassette that contains all the additional elements required for the expression of the receptor-encoding nucleic acid in host cells. A typical expression cassette thus contains a promoter operatively linked to the nucleic acid sequence encoding the receptor and signals required for efficient polyadenylation of the transcript, ribosome binding sites, and translation termination. The nucleic acid sequence encoding the receptor may typically be linked to a membrane-targeting signal such as the N-terminal 45 amino acids of the rat Somatostatin-3 receptor sequence to promote efficient cell-surface expression of the recombinant receptor. Additional elements of the cassette may include, for example enhancers.

An expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used Standard bacterial expression vectors include plasmids such as pBR322 based plasmids, pSKF, pET23D, and fusion expression systems such as GST and LacZ, but there are many more known in the art to the skilled person that can be usefully employed.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A.sup.+, pMTO10/A.sup.+, pMAMneo-5, baculovirus pDSVE, pcDNA3.1, pIRES and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable.

The elements that are typically included in expression vectors also include a replicon that functions in *E. coli*, a gene encoding drug resistance to permit selection of bacteria that harbor recombinant plasmids, and unique restriction sites in nonessential regions of the plasmid to allow insertion of eukaryotic sequences. The particular drug resistance gene chosen is not critical, any of the many drug resistance genes known in the art are suitable. The prokaryotic sequences are optionally chosen such that they do not interfere with the replication of the DNA in eukaryotic cells, if necessary.

Standard transfection methods can be used to produce bacterial, mammalian, yeast or insect cell lines that express large quantities of the receptor, which are then purified using standard techniques.

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. It is only necessary that the particular genetic engineering procedure used be capable of successfully introducing at least one gene into the host cell capable of expressing the receptor.

After the expression vector is introduced into the cells, the transfected cells may be cultured under conditions favoring expression of the receptor, which is recovered from the culture using standard techniques. For example the cells may be burst open either mechanically or by osmotic shock before being subject to precipitation and chromatography steps, the nature and sequence of which will depend on the particular recombinant material to be recovered. Alternatively, the recombinant protein may be recovered from the culture medium in which the recombinant cells had been cultured.

The activity of any of the receptors described herein can be assessed using a variety of in vitro and in vivo assays to determine functional, chemical, and physical effects, e.g., measuring ligand binding; secondary messengers (e.g., cAMP, cGMP, IP$_3$, DAG, or Ca$^{2+}$) ion flux, phosphorylation levels, transcription levels, neurotransmitter levels, and the like. Furthermore, such assays can be used to test for inhibitors of the receptors as is well known in the art.

Samples or assays that are treated with a potential receptor inhibitor may be compared to control samples without the test compound, to examine the extent of modulation. Control samples (untreated with inhibitors) are assigned a relative receptor activity value of 100. Inhibition of receptor activity is achieved when the receptor activity value relative to the control is lower, and conversely receptor activity is enhanced when activity relative to the control is higher.

The effects of the test compounds upon the function of the receptors can be measured by examining any of the parameters described above. Any suitable physiological change that affects receptor activity can be used to assess the influence of a test compound on the receptors of this invention. When the functional consequences are determined using intact cells or animals, one can measure a variety of effects such as changes in intracellular secondary messengers such as Ca$^{2+}$, IP$_3$ or cAMP.

Preferred assays for G-protein coupled receptors include cells that are loaded with ion sensitive dyes to report receptor activity. In assays for identifying modulatory compounds, changes in the level of ions in the cytoplasm or membrane voltage will be monitored using an ion sensitive or membrane voltage fluorescent indicator, respectively. For G-protein coupled receptors, promiscuous G-proteins such as G.alpha.15 and G.alpha.16 and chimeric G proteins can be used in the assay of choice (see, for example, Wilkie et al., *Proc. Nat. Acad. Sci. USA* 88, 10049-10053 (1991)). Such promiscuous G-proteins allow coupling of a wide range of receptors.

Receptor activation typically initiates subsequent intracellular events, e.g., increases in second messengers such as IP$_3$, which releases intracellular stores of calcium ions. Activation of some G-protein coupled receptors stimulates the formation of inositol triphosphate (1133) through phospholipase C-mediated hydrolysis of phosphatidylinositol (Berridge & Irvine, *Nature* 312, 315-21 (1984)). IP$_3$ in turn stimulates the release of intracellular calcium ion stores. Thus, a change in cytoplasmic calcium ion levels, or a change in second messenger levels such as IP$_3$ can be used to assess G-protein coupled receptor function. Cells expressing such G-protein coupled receptors may exhibit increased cytoplasmic calcium levels as a result of contribution from both intracellular stores and via activation of ion channels, in which case it may be desirable, although not necessary, to conduct such assays in calcium-free buffer, optionally supplemented with a chelating agent such as EGTA, to distinguish fluorescence response resulting from calcium release from internal stores.

In a preferred embodiment, receptor activity is measured by expressing the receptor in a heterologous cell with a promiscuous G-protein, such as G.alpha.15, 16, or a chimeric G-protein that links the receptor to a phospholipase C signal transduction pathway. Optionally the cell line is HEK-293, although other mammalian cells are also preferred such as CHO and COS cells. Modulation of taste transduction is assayed by measuring changes in intracellular $Ca^{2+}$ levels, which change in response to modulation of the receptor signal transduction pathway via administration of a molecule that associates with the receptor. Changes in $Ca^{2+}$ levels are optionally measured using fluorescent $Ca^{2+}$ indicator dyes and fluorometric imaging.

The type of assay described above with respect to G-protein coupled bitter taste receptors can, however, also be employed for the identification of binding compounds, in particular agonists or antagonists of any G-protein coupled signalling molecule, in particular G-protein coupled receptor. Therefore, another aspect of the present invention relates to a process for the identification of agonists or antagonists of G-protein coupled signalling molecules comprising the steps of (1) contacting a cell comprising a promiscuous G-protein like, for example. G.alpha.15, 16, or a chimeric G-protein, and a G-protein coupled signalling molecule, in particular receptor, with a the potential agonist or antagonists of the signalling molecule;

(2) determining whether the potential agonist or antagonists agonizes or antagonizes the activity of the signalling molecule.

The activity of the signalling molecule and the increase or decrease of that activity in response to the potential agonist or antagonist can be determined as outlined above with respect to the identification of bitter receptor taste activity. The respectively indicated percent increases or decreases of the activity, which are required to qualify as antagonist or agonist do apply mutatis mutandis. Additionally the term "contacting" has the meaning as outlined above. Preferably the signalling molecule and/or the promiscuous G-protein has been introduced into the cell. The type of cell, which are preferred are those indicated above.

In yet another embodiment, the ligand-binding domains of the receptors can be employed in vitro in soluble or solid-state reactions to assay for ligand binding. Ligand binding in a receptor, or a domain of a receptor, can be tested in solution, in a bilayer membrane attached to a solid phase in a lipid monolayer or vesicles. Thereby, the binding of a modulator to the receptor, or domain, can be observed using changes in spectroscopic characteristics, e.g. fluorescence, absorbance or refractive index; or hydrodynamic (e.g. shape), chromatographic, or solubility properties, as is generally known in the art.

The compounds tested as modulators of the receptors can be any small chemical compound, or a biological entity, such as a protein, sugar, nucleic acid or lipid. Typically, test compounds will be small chemical molecules. Essentially any chemical compound can be used as a potential modulator or ligand in the assays of the invention, although knowledge of the ligand specificity of an individual receptor would enable the skilled person to make an intelligent selection of interesting compounds. The assays may be designed to screen large chemical libraries by automating the assay steps and providing compounds from any convenient source to assays, which are typically run in parallel (e.g., in microtiter formats on microtiter plates in robotic assays). The skilled person will understand that there are many suppliers of libraries of chemical compounds.

Assays may be run in high throughput screening methods that involve providing a combinatorial chemical or peptide library containing a large number of potential therapeutic, or tastant compounds (that are potential ligand compounds). Such libraries are then screened in one or more assays, as described herein, to identify those library members (particular chemical species or subclasses) that display a desired characteristic activity. The compounds thus identified can serve as lead compounds to further develop modulators for final products, or can themselves be used as actual modulators.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of ammo acids in a polypeptide compound). Millions of chemical compounds can be synthesized through such combinatorial mixing of chemical building blocks.

Preparation and screening of combinatorial chemical libraries is well known to those of skill in the art and no more needs to be stated here.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds is possible using the integrated systems of the invention.

Lead compounds found by assay technology herein above described, or development compounds formed from such leads can be administered directly to a human subject to modulate bitter taste. Alternatively, such compounds can be formulated with other ingredients of preparations to be taken orally, for example, foods, including animal food, and beverages, pharmaceutical or nutraceutical or homeopathic preparations.

Therefore, another aspect of the invention is a process for the production of foodstuffs or any precursor material or additive employed in the production of foodstuffs comprising the steps of the above described processes for the identification of a compound binding to hTAS2R or an antagonist of hTAS2R and the subsequent step of admixing the identified compound or antagonist with foodstuffs or any precursor material or additive employed in the production of foodstuffs.

Bitter taste is a particular problem when orally administering pharmaceuticals, which often have an unpleasant bitter taste. In particular in elderly persons, children and chronically ill patients this taste can lead to a lack of compliance with a treatment regimen. In addition in veterinary applications the oral administration of bitter tasting pharmaceuticals can be problematic. Therefore, a further aspect of the invention is a process for the production of a nutraceutical or pharmaceutical composition comprising the steps of the processes of a compound binding to hTAS2R or an antagonist of hTAS2R and the subsequent step of formulating the compound or antagonist with an active agent in a pharmaceutically acceptable form.

Consequently, a further aspect of the invention is a foodstuff, in particular animal food, or any precursor material or additive employed in the production of foodstuffs comprising an antagonist/inhibitor described above, preferably an antibody directed against one of the hTAS2Rs described herein, the extracellular domain of one of the hTAS2Rs described herein or an inhibiting RNA.

Also comprised is a nutraceutical or pharmaceutical composition comprising an antagonist/inhibitor as described above, preferably an antibody directed against one of the hTAS2Rs described herein, the extracellular domain of one of the hTAS2Rs described herein or an inhibiting RNA and an active agent, which preferably inhibits a bitter taste, and optionally a pharmaceutically acceptable carrier.

The amount of compound to be taken orally must be sufficient to effect a beneficial response in the human subject, and will be determined by the efficacy of the particular taste modulators and the existence, nature, and extent of any adverse side-effects that accompany the administration of a particular compound. There now follows a series of examples that serve to illustrate the invention, not to limit.

A further aspect of the present invention is the use of a polynucleotide as described above, a vector as described above, an antibody as described above or an antagonist/inhibitor of as described above, preferably an antibody directed against one of the hTAS2Rs described herein, the extracellular domain of one of the hTAS2Rs described herein or an inhibiting RNA for the manufacture of a medicament for the treatment of an abnormally increased or decreased sensitivity towards a bitter substance.

Techniques associated with detection or regulation of genes are well known to skilled artisans. Such techniques can be used, for example, for basic research on bitter receptors and to diagnose and/or treat disorders associated with aberrant bitter receptor expression.

The following examples are merely illustrative of the present invention and should not be construed to limit the scope of the invention as indicated by the appended claims in any way. The contents of the U.S. provisional application Ser. No. 60/413,298 the priority of which is claimed is hereby incorporated by reference in its entirety.

EXAMPLE 1

Cloning of the hTAS2R Genes

Human genomic DNA was isolated from HEK293 cells using the E.Z.N.A. Blood DNA Kit II (Peqlab) and the various hTAS2Rs were amplified by PCR using gene-specific primers that span the complete coding region of the individual hTAS2R genes. Reaction parameters were 4 cycles; 1 min, 94° C.; 1 min, 64° C.; 1.5 min 68° C. using Advantage 2 polymerase (Clontech). 5% of the reaction served then as template for further amplification with Pfu DNA polymerase (Promega): 30 cycles; 1 min, 94° C.; 1 min, 64° C.; 3 min, 72° C. The hTAS2R amplicons were then sub-cloned into a cassette based on pcDNAS-FRT (Invitrogen). The cloning cassette contains the first 45 amino acids of the rat somatostatin type 3 receptor (as is further described by Meyerhof et al., *Proc. Nat. Acad. Sci. USA*, 89, 10267-10271 (1992)) as a cell surface-targeting signal at the N-terminus. The C-terminus contained the herpes simplex virus (HSV) glycoprotein D epitope which does not interfere with signaling of heptahelical receptors and can be used for immunocytochemistry using an antibody that binds specifically to the HSV glycoprotein D epitope (see Roosterman et al, J. Neuroendocrinol, 9, 741-751 (1997)). Comparison of the DNA sequences of at least four clones identified mutations generated during PCR and this avoided picking mutated clones. We compared the amino acid sequences using the AlignX program of the Vector NTI™ Suite (InforMax).

Using the above-described method, DNA sequences encoding all 24 bitter receptors identified by applicant were cloned. As indicated above, they were derived by a PCR-based method using genomic DNA as the template. Since all of the 24 genomic sequences lack introns, the DNA clones obtained had the same sequences as corresponding cDNA clones derived by reverse transcription-PCR(RT-PCR) of mRNA from cells expressing the relevant polypeptides would have.

EXAMPLE 2

Immunocytochemistry

Batches of HEK293 cells were separately transiently transfected with expression vectors (pCDN5/FRT; Invitrogen) containing each of the 24 above described coding sequences using lipofectamine 2000 (Invitrogen) and aliquots of the resulting cell populations were separately seeded on polylysine-coated coverslips. At 24 h post transfection they were washed with phosphate buffered saline (PBS), cooled on ice and added 20 microgram/ml biotin-labeled concanavalin A (Sigma) for 1 h, which binds to cell surface glycoproteins. Thereafter, the cells were fixed for 5 min in methanol/acetone (1:1) and then permeabilized for 4 min with 0.25% Triton X-100. In order to reduce nonspecific binding the coverslips were incubated in 2% goat serum. Thereafter, anti-HSV glycoprotein D antiserum (Novagen, 1:10,000) was added to detect the chimeric receptors that, as described above, would have a HSV glycoprotein epitope fused to their C-termini, and Texas Red-Avidin D (Vector, 1:200) has added to stain the cell surface and incubation continued overnight at 4° C. Such C-termini are intracellular and for this reason it is necessary to permeabilize the cells to permit entry of the HSV glycoprotein D epitope-specific antibody molecules into them. After washing (5× in PBS, RT) Alexa488-conjugated goat anti-mouse antiserum (Molecular Probes, 1:1000) was added and incubation continued at room temperature for 1 h. Finally, the cells were embedded in Fluorescent Mounting Medium (Dako) and analyzed using a Leica TCS SP2 Laser Scan Inverted microscope. The preparations were scanned sequentially with an argon/krypton laser (488 nm) to excite the Alexa488 dye and with a green-helium-neon laser (543 nm) to excite the Texas Red dye. The spectral detector recorded light emission at 510-560 nm and 580-660 nm, respectively. Images of 1024×1024 pixels were processed with Corel PHOTO-PAINT 10.0 (Corel Corporation) and printed on a Tektronix color laser printer. The immunocytochemical data permitted calculation of the proportion of cells expressing recombinant receptors (green fluorescent cells divided by total cell number in a microscopic field) and the proportion of cells that display expression of TAS2Rs at the plasma membrane level (number of cells with colocalization of green and red fluorescence divided by the number of green fluorescent cells). Of the 24 transfectant lines tested, all were found to express the encoded polypeptides. The proportion of receptor-expressing cells in the various transfectant lines ranged from about 10% to about 35%.

EXAMPLE 3

Heterologous Expression of hTAS2R Receptors

A fluorescence imaging plate reader (FLIPR, Molecular Devices) was used to functionally screen cell populations transiently transfected with expression vectors encoding the above-described 24 bitter receptors and to establish concentration-response curves for hTAS2R16 and hTASR10. The single-cell calcium imaging technique was also employed to demonstrate receptor selectivity and crossdesensitization. For the FLIPR experiments the HEK293/15 cells were grown to 50% confluence. The cells were then seeded at a density of $3 \times 10^3$ cells per well into 96-well black-wall, clear-bottom microtiter plates (Greiner). After 48 h the cells in each well were transfected using Lipofectamine 2000 and 24-30 h later were loaded with Fluo4AM (Molecular Probes). Thereafter they were stimulated with bitter compounds (SigmaAldrich, further purified by reversed-phase HPLC to >99% purity). Calcium signals were recorded simultaneously from each well at 1 Hz at 510 nm after excitation at 488 nm and the recordings were corrected for cell density. The responses of five wells containing cells expressing the same receptor and that received the same stimulus (i.e., the same compound at the same concentration) were averaged. Calcium traces were subtracted that were determined in triplicate of mock-transfected cells stimulated with the same concentration of tastant. The calculations rest on at least four independent transfection experiments. Plots of the amplitudes versus concentrations fitted by nonlinear regression to the function $f(x)=100/(1+(EC_{50}/x)^{nH})$, with x=agonist concentration and nH=Hill coefficient permitted calculation of $EC_{50}$ values and threshold values of activation.

$EC_{50}$ and threshold values obtained with hTAS2R16-expressing transfectants are shown in Table 1 below and the results are described in Example 4.

In separate experiments, hTAS2R10-expressing transfectants were found to have a threshold of activation of approximately 0.1 µM and a $EC_{50}$ of 5-20 µM using strychnine as the test compound. Similar results were obtained with brucine.

Single-cell $Ca^{2+}$ imaging was performed with the hTAS2R16-transfected HEK293/15 cells as described in *Cell* 95, 917-926 (1998), but with the following modifications: The Till Photonics imaging system (Munich, Germany) was used in which a monochromator is connected by a quartz fiber lightguide and an epifluorescence condenser to an inverted Olympus IX50 microscope equipped with a UApo/340 40x1.35 oil-immersion lens. 30 h post-transfection, FURA-2AM-loaded cells were sequentially illuminated in 5 s intervals for 3-10 ms, first at 340 nm, then at 380 nm, online ratioed light emissions at 510 nm (340/380) and monitored the images via an intensified, cooled CCD camera. The 5 s interval camera pictures of all cells in the microscope field of vision permanently were stored and analyzed offline. 10-15% of all cells in the camera field responded to agonists in transient transfection experiments. The proportion of responders was about half of that found by immunocytochemistry, probably reflecting a sub-optimal signal transduction. Responses were not observed in mock-transfected cells. Isoproterenol (10 microMolar) was used at the end of all experiments to stimulate endogenous betaadrenergic receptors, proving a functional $G_{alpha\ 15}$ dependent signal transduction cascade.

For RT-PCR and in-situ hybridization work, human RNA (Clontech) was purchased or it was isolated from surgical tongue specimens with peqGOLD RNAPure (Peqlab) and the preparations digested with DNase I (Invitrogen). Following cDNA synthesis (Smart cDNA synthesis Kit, Clontech) hTAS2R16 cDNA was PCR-amplified (39 cycles, 1 min 94° C., 1 min 64° C., 1 min 72° C.) using specific forward and reverse primers with overhangs containing EcoRI or NotI sites SEQ ID Nos 51 and 52 and the amplicons analyzed on agarose gels. Subcloning and sequencing demonstrated the identity of the amplified bands. Approximately 15 micrometer cryo-sections of human tongue specimens containing vallate papilla at 65° C. were processed and hybridized with a hTAS2R16 riboprobe spanning the complete coding region and generated from hTAS2R16 cDNA. The in-situ hybridization method used was essentially the same as that described in *Nature*, 413, 631-635 (2001) except that the riboprobe was conjugated with biotin and an alkaline phosphatase-avidin conjugate was used for detection. This experiment indicated that TAS2R16 mRNA is expressed in vallate papilla which are known to perceive bitter taste.

EXAMPLE 4

Human Taste Experiments 15 experienced panelists in a sensory panel room at 22-25° C. determined bitter thresholds on three different sessions using a triangle test with tap water as solvent, according to methodology set out in *J. Agric. Food Chem.*, 49, 231-238 (2001), or Mailgaard M et al, "*Sensory Evaluation Techniques*" (CRC Press LLC, New York 1999). For dose-response relations, bitter tastant concentration series were presented to 10 trained panelists in random order. The panelists ranked the samples in increasing order of intensity and, for each concentration, evaluated bitterness intensity on a scale from 0 to 5 (ref 24). The dose-response curves of three different sessions were averaged. The intensity values between individuals and separate sessions differed by not more than 0.5 units.

To investigate adaptation, the 8 panelists first maintained aqueous solutions (5 ml) of phenyl-β-D-glucopyranoside (8 mM), phenyl-alpha-D-glucopyranoside (180 mM), salicin (8 mM), or helicin (8 mM) for 15 s in their oral cavities and evaluated the bitter intensity as described above. After 30 min, they kept a denatonium benzoate solution (5 ml, 0.0003 mM) for 15 s in their mouth and evaluated its bitterness. The panelists spat off the denatonium benzoate solution, took up the phenyl-β-D-glucopyranoside or the phenyl-alpha-D-glucopyranoside solutions orally for 120 s or 180 s and judged their bitterness intensity after 15, 30, 60, 120 and 180 s. Thereafter, the panelists spat off these solutions and then sequentially took up salicin, helicin (5 ml, 8 mM) and denatonium benzoate (5 ml, 0.0003 mM) and evaluated bitterness intensities of these solutions after 15 s. After an additional 30 min, the first experiment was repeated. The data of three different sessions for each panelist were averaged. Intensity values between individuals and separate sessions differed by not more than ±0.5 units.

Results of in vitro assays (FLIPR) and human taste experiments are shown in Table 1 below.

TABLE II

| | Threshold Value (mM) | | $EC_{50}$ (mM) | |
|---|---|---|---|---|
| Compound | FLIPR | Human | FLIPR | Human |
| 1 | 0.07 +/− 0.02 | 0.1 +/− 0.05 | 1.1 +/− 0.1 | 0.7 +/− 0.2 |
| 2 | 0.07 +/− 0.02 | 0.2 +/− 0.1 | 1.4 +/− 0.2 | 1.1 +/− 0.3 |
| 3 | 0.3 +/− 0.1 | 0.4 +/− 0.1 | 2.3 +/− 0.4 | 2.2 +/− 0.7 |
| 4 | 0.5 +/− 0.2 | 0.9 +/− 0.3 | 5.8 +/− 0.9 | 5.4 +/− 1.8 |
| 5 | 1.5 +/− 0.5 | n.d. | n.d. | n.d. |

TABLE II-continued

| | Threshold Value (mM) | | EC$_{50}$ (mM) | |
|---|---|---|---|---|
| Compound | FLIPR | Human | FLIPR | Human |
| 6 | 0.4 +/− 0.1 | 0.2 +/− 0.1 | 1.0 +/− 0.1 | 1.4 +/− 0.4 |
| 7 | 15 +/− 6 | 32 +/− 11 | n.d. | 320 +/− 108 |
| 8 | 2.3 +/− 0.9 | n.d. | 20 +/− 3.4 | n.d. |
| 9 | 4 +/− 2 | 4 +/− 1 | n.d. | n.d. |
| 10 | n.r. | 40 +/− 13 | n.r. | n.d. |
| 11 | n.r. | 9 +/− 3 | n.r. | 50 +/− 17 |

1 = phenyl-beta-D-glucopyranoside;
2 = salicin;
3 = helicin;
4 = arbutin;
5 = 2-nitro-phenyl-beta-D-glucopyranoside;
6 = naphthyl-beta-D-pyranoside;
7 = methyl-beta-D-lucopyranoside;
8 = amygdalin;
9 = esculin;
10 = phenyl-beta-D-galactopyranoside;
11 = phenyl-alpha-D-glucopyranoside.
n.d. = not data due to solubility problems or toxicity or artifacts in vitro.
n.r. = No response up to 100 mM.

The FLIPR results provide the threshold concentration of the compounds (nM) at which point the receptor detects the compounds. The EC$_{50}$ results express the concentration of the compound wherein the receptor signal is at 50%, and is a representation of the affinity of a receptor for a compound.

The results show that the in vitro FLIPR measurements for salicin closely resemble the human taste study results. This bitter-tasting compound has known anti-pyretic and analgesic action, and the results suggest that in vitro assays using hTAS2R16 may represent a useful tool to find compounds that suppress or eliminate the bitter response to this compound. Also, for all the other tested beta-glucopyranosides, the close correspondence of Threshold Concentration and EC$_{50}$ results suggest that hTAS2R16 is a cognate human receptor for these class of bitter compounds. In contrast, the related structures (see compounds 10 and 11) show 90- to 400-fold higher Threshold Concentrations, which indicates that this receptor is rather selective, and that these bitter compounds activate different receptors.

Adaptation frequently occurs in sensory systems and means that stimuli elicit reduced responses upon prolonged or repeated stimulus presentations. Repeated stimulation of hTAS2R16-expressing cells with phenyl-beta-D-glucopyranoside resulted in largely diminished responses to salicin as well. This cross-desensitization occurred among the other tested beta-pyranosides and was fully reversible. It resembles homologous desensitization of agonist-occupied heptahelical receptors mediated by GRKs, i.e. specific kinases, and arrestins. We also observed adaptation in the human test panel that initially scored phenyl-beta-D-glucopyranoside, salicin and helicin as equally intensely bitter. The bitterness of phenyl-beta-D glucopyranoside declined during prolonged stimulation and the test panel perceived salicin and helicin also as less bitter, but not the unrelated bitter substance denatonium benzoate, which cannot activate TAS2R16. Adaptation was fully reversible. On the opposite, the phenyl-alpha-D-glucopyranoside failed to cross-adapt with all tested beta-D-glucopyranosides, although its own bitter response desensitized strongly. This indicates that beta-glucopyranosides signal through a common mechanism most likely involving hTAS2R16 as a bitter taste receptor while the alpha-isomer activates a separate receptor. A recent human psychophysical study also revealed cross-adaptation amongst two bitter amino acids but not between the two bitter amino acids and urea, suggesting the existence of distinct receptors for the bitter amino acids and urea. Although most, if not all, bitter receptors are present in the same subset of taste receptor cells, adaptation to specific bitter stimuli can be explained if bitter receptors were subject to homologous desensitization.

EXAMPLE 5

Heterologous Expression of hTAS2R

Transient transfection of TAS2Rs into HEK-293T-Gα16gustducin44 cells. We cloned the DNAs of all human putative bitter responsive receptors into pcDNA5/FRT (Invitrogen) by PCR-methods and transiently transfected the plasmids with lipofectamine 2000 (Invitrogen) into HEK-293T-Gα16gustducin44 cells grown to 50% confluence. These cells stably express a chimeric G protein constructed from human Gα16 and rat gustducin. Finally, we seeded the transfected cells at a density of 3×10$^3$ cells per well into 96-well black-wall, clear-bottom microtiter plates (Greiner).

Co-transfection of TAS2Rs with gustducin and phospholipase-Cβ2 into HEK-293 cells. Alternatively, we transfected simultaneously plasmid DNAs encoding one of the TAS2Rs, phospholipase-Cβ2 and α-gustducin into HEK-293 cells using the lipofectamine method. Additional cotransfection of G-protein and β and γ-subunits may improve the bitter tastant-induced responses. Thereafter, the transfected cells were seeded at a density of 3×10$^3$ cells per well into 96-well black-wall, clear-bottom microtiter plates (Greiner).

Fluorometric Imaging Plate Reader (FLIPR) assay 24-30 h later, the cells were loaded with 4 μM FLUO-4/AM (Molecular Probes) and 0.04% Pluronic F-127 (Molecular Probes) in Hepes-buffered saline (HBS), 140 mM NaCl, 5 mM KCl, 2.5 mM CaCl$_2$, 10 mM Hepes, 10 mM glucose and 2.5 in M probenicide, pH 7.4, for 1 hour at 37° C. Thereafter, cells were gen tly washed in HBS by an automated plate washer (Denley Cellwash, Labsystems) and transferred to the FLIPR (Molecular Devices). The FLIPR integrates an argon laser excitation source, a 96-well pipettor, and a detection system utilizing a Charged Coupled Device imaging camera. Fluorescence emissions from the 96 wells were monitored at an emission wavelength of 510 nm, after excitation with 488 nm (F488). Fluorescence data were collected 1 min before and 10 min after stimulation. Data were collected every 6 s before and every 1 s after agonist stimulation. 50 μl of 3× concentrated agonists were delivered within 2 s by the integrated 96-well pipettor to the wells containing 100 μl HBS. Agonist responses were quantified using the amplitudes of the fluorescence peaks. We averaged the responses of five wells containing cells expressing the same receptor and that received the same stimulus. Calcium traces were determined in triplicate of mock-transfected cells stimulated with the same concentration of tastant. EC$_{50}$ values and plots of the amplitudes versus concentrations were derived from fitting the data by nonlinear regression to the function $f(x)=100/[1+(EC_{50}/x)^{nH}]$, where x is the agonist concentration and nH is the Hill coefficient. The results for hTAS2R10 (Table II), hTAS2R14 (Table III), hTAS2R16 (Table IV), hTAS2R38 (Table V), hTAS2R43 (Table VI), hTAS2R44 (Table VII), hTAS2R45 (Table VIII), hTAS2R46 (Table IX) and hTAS2R (Table X) are shown below.

TABLE III

Identified agonists of hTAS2R10

| Substance | Structure | Approx. threshold [mM] | EC₅₀ [mM] |
|---|---|---|---|
| Strychnine * | 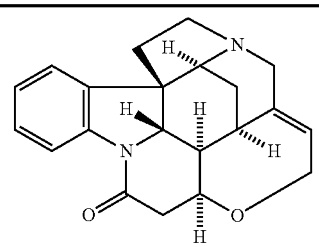 | 0.003 | 0.04 |
| Brucine | 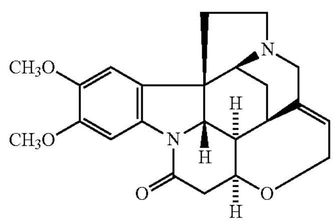 | 0.01 | 0.06 |
| Denatonium benzoate | 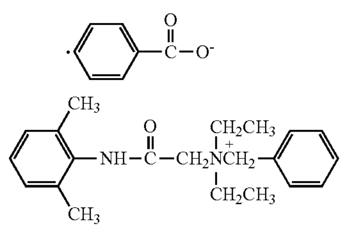 | 0.003 | 0.07 |

TABLE III-continued

Identified agonists of hTAS2R10

| Substance | Structure | Approx. threshold [mM] | EC₅₀ [mM] |
|---|---|---|---|
| Absinthine | 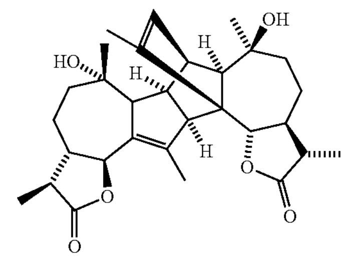 | 0.01 | |

TABLE IV

Identified agonists of hTAS2R14

| Substance | Structure | Reacts at |
|---|---|---|
| L-Tyrosine | 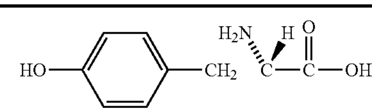 | 1 mM |

TABLE V

Identified agonists of hTAS2R16

| Substance | Structure | Threshold [mM] | EC₅₀ [mM] |
|---|---|---|---|
| Naphtyl-β-D-Glucoside | 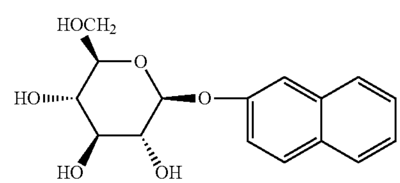 | 0.4 ± 0.1 | 1.0 ± 0.1 |
| Phenyl-β-D-Glucoside | 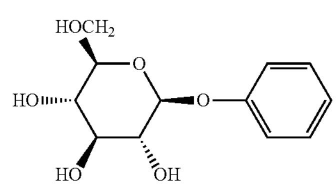 | 0.07 ± 0.02 | 1.1 ± 0.1 |
| Salicin | 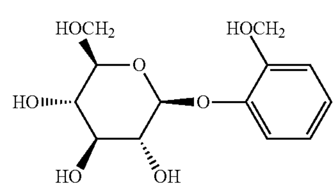 | 0.07 ± 0.02 | 1.4 ± 0.2 |

TABLE V-continued

| Identified agonists of hTAS2R16 | | | |
|---|---|---|---|
| Substance | Structure | Threshold [mM] | $EC_{50}$ [mM] |
| Helicin | | 0.3 ± 0.1 | 2.3 ± 0.4 |
| Arbutin | | 0.5 ± 0.2 | 5.8 ± 0.9 |
| 2-Nitrophenyl-β-D-Glucoside | | 0.3-1 | Not determined |
| 4-Nitrophenyl-β-D-Glucoside | | 1-3 | Not determined |
| Methyl-β-D-Glucoside * | | 15 ± 6 | 32 ± 11 |
| Esculin | | 4 ± 2 | Not determined |
| 4-Nitrophenyl-β-D-Thioglucoside | | 1-5 | Not determined |
| 4-Nitrophenyl-β-D-Mannoside | | 1-3 | Not determined |

TABLE V-continued

Identified agonists of hTAS2R16

| Substance | Structure | Threshold [mM] | EC$_{50}$ [mM] |
|---|---|---|---|
| Amygdalin | 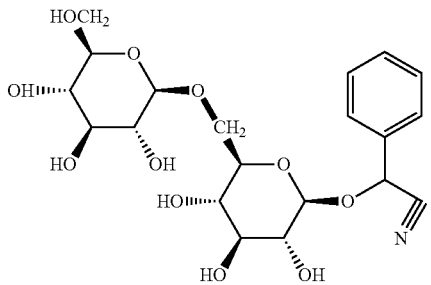 | 2.3 ± 0.9 | 20 ± 3.4 |

TABLE VI

Identified agonists of hTAS2R38

| Substance | Structure | Approx. Threshold [μM] | EC$_{50}$ [μM] |
|---|---|---|---|
| Acetylthiourea | CH$_3$—C(=O)—NH—C(=S)—NH$_2$ | 2 | 15 |
| N,N-Dimethyl-thioformamide | H—C(=S)—N(CH$_3$)$_2$ | 10 | 55 |
| N,N'-Diphenylthiourea | Ph—NH—C(=S)—NH—Ph | 0.3 | 2.3 |
| N-Ethylthiourea | CH$_3$CH$_2$NH—C(=S)—NH$_2$ | 30 | 260 |
| 2-Imidazolidine-thione (=N,N'-Ethylenethiourea) | (cyclic ethylene thiourea) | 10 | not determined |
| 4(6)-Methyl-2-thiouracil | (6-methyl-2-thiouracil) | 20 | 180 |
| N-Methylthiourea | CH$_3$NH—C(=S)—NH$_2$ | 100 | estimated 600-800 |
| Phenyl-thiocarbamid (PTC) | Ph—NH—C(=S)—NH$_2$ | 0.3 | 2 |
| 6-Phenyl-2-thiouracil | (6-phenoxy-2-thiouracil) | 0.15 | 0.5 |
| 6-Propyl-2-thiouracil (PROP) | (6-propyl-2-thiouracil) | 0.3 | 2 |
| Tetramethyl-thiourea | (CH$_3$)$_2$N—C(=S)—N(CH$_3$)$_2$ | 10-30 | 100 |
| Thioacetamide | CH$_3$—C(=S)—NH$_2$ | 100 | not determined |
| Thioacetanilide | CH$_3$—C(=S)—NH—Ph | 3 | 18 |
| 2-Thiobarbituric acid | (2-thiobarbituric acid) | reacts at 10 mM | |

TABLE VI-continued

Identified agonists of hTAS2R38

| Substance | Structure | Approx. Threshold [μM] | EC$_{50}$ [μM] |
|---|---|---|---|
| 2-Thiouracil | 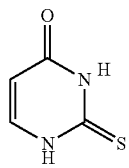 | 300 | estimated 2000 |

TABLE VII

Identified agonists of hTAS2R43

| Substance | Structure | Approx. Threshold [mM] | EC$_{50}$ [mM] |
|---|---|---|---|
| Saccharin | 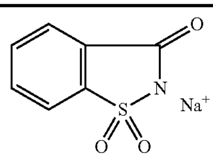 | 0.2 | 1.1 |
| Acesulfame K | 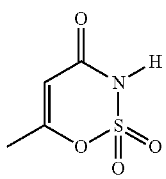 | No response up to 10 mM | |

TABLE VIII

Identified agonists of hTAS2R44

| Substance | Structure | Approx. Threshold [mM] | EC$_{50}$ [mM] |
|---|---|---|---|
| Saccharin | 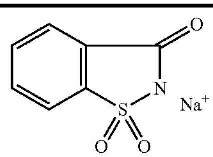 | 0.2 | estimated 2-5 |
| Acesulfame K | 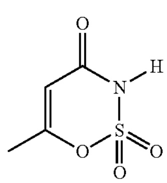 | 0.5 | 3 |

TABLE IX

Identified agonists of hTAS2R45

| Substance | Structure | Approx. Threshold [mM] | EC$_{50}$ [mM] |
|---|---|---|---|
| Absinthine | 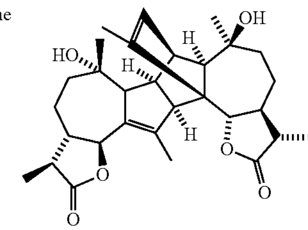 | 0.003 | Not determined |

TABLE X

Identified agonists of hTAS2R46

| Substance | Structure | Approx. Threshold [mM] | EC$_{50}$ [mM] |
|---|---|---|---|
| Absinthine | 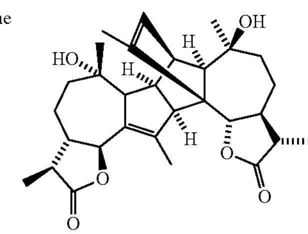 | 0.001 | Not determined |

TABLE XI

Identified agonists of hTAS2R48

| Substance | Structure | Approx. Threshold [mM] | EC$_{50}$ [mM] |
|---|---|---|---|
| Absinthine | 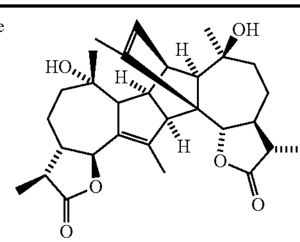 | 0.03 | Not determined |

We claim:

1. A process for identifying a compound that binds to a polypeptide selected from the group consisting of:
   (a) a polypeptide comprising the amino acid sequence as shown in SEQ ID NO:37;
   (b) a fragment or derivative of a polypeptide of (a), wherein in said derivative no more than 15 amino acid residues are conservatively substituted compared to said polypeptide, wherein said fragment comprises at least 290 contiguous amino acids of SEQ ID NO:37 and said fragment or derivative has bitter substance binding activity; and
   (c) a polypeptide which is at least 95% identical to a polypeptide as defined in any one of (a) to (b) and which has bitter substance binding activity; and wherein said process comprises:
   (1) contacting said polypeptide, or a host cell genetically engineered with a polynucleotide encoding said polypeptide, or with a vector containing a polynucleotide encoding said polypeptide, with a compound;
   (2) detecting the presence of the compound which binds to said polypeptide; and
   (3) determining whether the compound binds said polypeptide;

wherein prior to, concomitantly and/or after step (1) said polypeptide or said host cell is contacted with an agonist selected from the group consisting of strychnine, brucine, and functional derivatives thereof.

2. A process selected from the group consisting of:
   A. a process for the production of a food or any precursor material or additive employed in the production of foodstuffs comprising:
      (1) identifying a compound according to the process of claim 1, and
      (2) admixing the identified compound with foodstuffs or any precursor material or additive employed in the production of foodstuffs; and
   B. a process for the production of a nutraceutical or pharmaceutical composition, comprising:

(1) identifying a compound according to the process of claim 1, and
(2) formulating the identified compound with an active agent in a pharmaceutically acceptable form.

3. A process for identifying an antagonist of the bitter taste receptor activity of the polypeptide selected from the group consisting of:
  (a) a polypeptide comprising the amino acid sequence as shown in SEQ ID NO:37;
  (b) a fragment or derivative of a polypeptide of (a), wherein in said derivative no more than 15 amino acid residues are conservatively substituted compared to said polypeptide, wherein said fragment comprises at least 290 contiguous amino acids of SEQ ID NO:37 and said fragment or derivative has bitter taste receptor activity; and
  (c) a polypeptide which is at least 95% identical to a polypeptide as defined in any one of (a) to (b) and which has bitter taste receptor activity; and
wherein said process comprises:
  (1) contacting said polypeptide, or a host cell genetically engineered with a polynucleotide encoding said polypeptide or with a vector containing a polynucleotide encoding said polypeptide, with a potential antagonist; and
  (2) determining whether the potential antagonist antagonizes the bitter taste receptor activity of said polypeptide;
wherein prior to, concomitantly and/or after step (1) said bitter taste receptor or said host cell is contacted with an agonist selected from the group consisting of strychnine, brucine, and functional derivatives thereof.

4. A process selected from the group consisting of:
  A. a process for the production of a food or any precursor material or additive employed in the production of foodstuffs comprising:
    (1) identifying an antagonist of the bitter taste receptor activity according to the process of claim 3, and
    (2) admixing the identified antagonist with foodstuffs or any precursor material or additive employed in the production of foodstuffs; and
  B. a process for the production of a nutraceutical or pharmaceutical composition, comprising:
    (1) identifying an antagonist of the bitter taste receptor activity according to the process of claim 3, and
    (2) formulating the identified antagonist with an active agent in a pharmaceutically acceptable form.

\* \* \* \* \*

UNITED STATES PATENT AND TRADEMARK OFFICE
CERTIFICATE OF CORRECTION

PATENT NO. : 8,709,737 B2
APPLICATION NO. : 13/071924
DATED : April 29, 2014
INVENTOR(S) : Bufe et al.

It is certified that error appears in the above-identified patent and that said Letters Patent is hereby corrected as shown below:

In the Specification

Column 7,
Line 9, "HTLV, or HIV;" should read --HTLV, MMTV or HIV;--.

Column 7,
Line 30, "deammase (ADA)" should read --deaminase (ADA)--.

Column 8,
Line 12, "vi ruses" should read --viruses--.

Column 9,
Line 17, "fall-length" should read --full-length--.

Column 9,
Line 23, "fall-length" should read --full-length--.

Column 9,
Lines 51-52, "Methods ell-known" should read --Methods well-known--.

Column 12,
Line 46, "hTAS2R5," should read --hTAS2Rs,--.

Column 15,
Line 64, "two three" should read --two, three--.

Column 18,
Line 18, "of" should read --of:--.

Signed and Sealed this
Twenty-first Day of October, 2014

Michelle K. Lee
*Deputy Director of the United States Patent and Trademark Office*

Column 18,
Line 39, "NO 13 and SEQ ID NO 14" should read --NO: 13 and SEQ ID NO: 14--.

Column 18,
Line 43, "NO 15 and SEQ ID NO 16" should read --NO: 15 and SEQ ID NO: 16--.

Column 18,
Line 47, "NO 19 and SEQ ID NO 20" should read --NO: 19 and SEQ ID NO: 20--.

Column 18,
Line 51, "NO 37 and SEQ ID NO 38" should read --NO: 37 and SEQ ID NO: 38--.

Column 22,
Line 2, "(C2-" should read --($C_2$- --.

Column 22,
Line 4, "particulars" should read --particular--.

Column 24,
Line 20, "binding; secondary" should read --binding, secondary--.

Column 25,
Line 25, "of" should read --of:--.

Column 27,
Line 54, "were" should read --were:--.

Column 27,
Line 60, "on pcDNAS-" should read --on pcDNA5- --.

Column 32,
Line 38, "2.5 in M" should read --2.5 mM--.

Column 32,
Line 40, "gen tly" should read --gently--.

Column 35,
Lines 35-43,

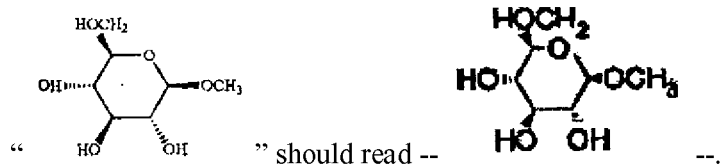

CERTIFICATE OF CORRECTION (continued)
U.S. Pat. No. 8,709,737 B2

Column 35,
Line 43-50,

" 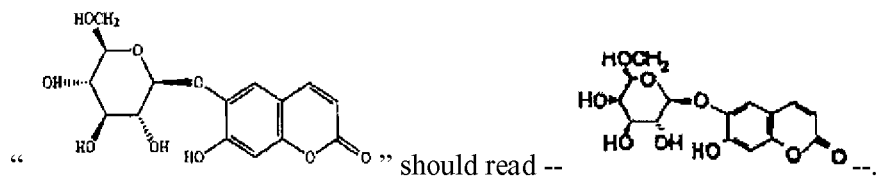 " should read -- 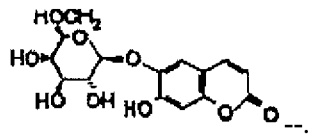 --.

Column 37,
Line 5-12,

" 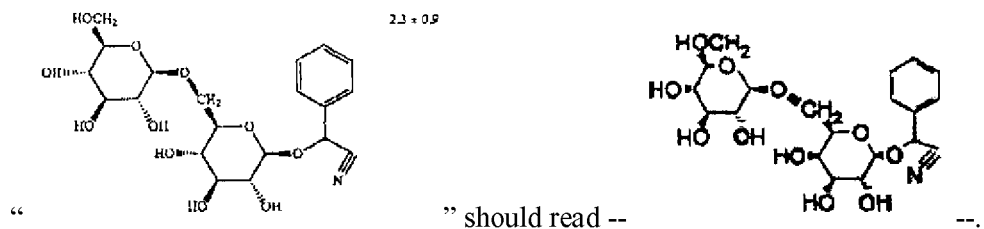 " should read -- 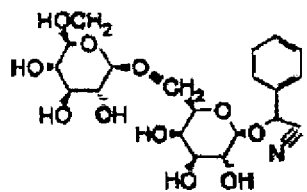 --.